(12) United States Patent
Scafaro et al.

(10) Patent No.: US 10,655,138 B2
(45) Date of Patent: May 19, 2020

(54) THERMOSTABLE RUBISCO ACTIVASE COMPLEXES

(71) Applicant: Macquarie University, Macquarie University (AU)

(72) Inventors: Andrew Scafaro, Ghent (BE); Brian Atwell, Riverview (AU)

(73) Assignee: Macquarie University (AU)

( * ) Notice: Subject to any disclaimer, the term of this patent is extended or adjusted under 35 U.S.C. 154(b) by 0 days.

(21) Appl. No.: 15/545,870

(22) PCT Filed: Jan. 22, 2016

(86) PCT No.: PCT/AU2016/000011
§ 371 (c)(1),
(2) Date: Jul. 24, 2017

(87) PCT Pub. No.: WO2016/115594
PCT Pub. Date: Jul. 28, 2016

(65) Prior Publication Data
US 2018/0037904 A1    Feb. 8, 2018

(30) Foreign Application Priority Data

Jan. 22, 2015 (AU) .............................. 2015900182

(51) Int. Cl.
C12N 15/82 (2006.01)
C12N 9/88 (2006.01)
C07K 14/415 (2006.01)

(52) U.S. Cl.
CPC ........ *C12N 15/8273* (2013.01); *C07K 14/415* (2013.01); *C12N 9/88* (2013.01); *C12N 15/8237* (2013.01); *C12N 15/8238* (2013.01); *C12N 15/8271* (2013.01); *C12Y 401/01039* (2013.01)

(58) Field of Classification Search
None
See application file for complete search history.

(56) References Cited

U.S. PATENT DOCUMENTS

| 2007/0050864 | A1 | 3/2007 | Kurek et al. |
| 2007/0294782 | A1 | 12/2007 | Abad et al. |
| 2013/0117886 | A1 | 5/2013 | Troukhan et al. |
| 2014/0130203 | A1 | 5/2014 | La Rosa et al. |
| 2014/0182015 | A1 | 6/2014 | Broekaert et al. |

OTHER PUBLICATIONS

Kurek et al. Enhanced Thermostability of *Arabidopsis* Rubisco Activase Improves Photosynthesis and Growth Rates under Moderate Heat Stress. The Plant Cell. 2007. 19: 3230-3241.*

Hong et al. Overexpression of AtDREB1A in chrysanthemum enhances tolerance to heat stress. Plant Molecular Biology. 2009. 70: 231-240.*

(Continued)

*Primary Examiner* — Ashley K Buran
(74) *Attorney, Agent, or Firm* — Mendelsohn Dunleavy, P.C.

(57) ABSTRACT

The present invention relates to Rubisco activase (RCA) and functionally equivalent polypeptides that confer thermostability to a complex comprising Rubisco activase and Ribulose-1,5-bis-phosphate carboxylase/oxygenase (Rubisco).

29 Claims, 33 Drawing Sheets
Specification includes a Sequence Listing.

(56) References Cited

OTHER PUBLICATIONS

Atwell et al. Could abiotic stress tolerance in wild relatives of rice be used to improve *Oryza sativa*? Plant Science. 2014. 215-216: 48-58.*

GenBank Accesion No. BAA97583. RuBisCO activase large isoform precursor [*Oryza sativa* Japonica Group]. Published Jul. 4, 2000. pp. 1.*

GenBank Accession No. AB034698. *Oryza sativa* OsrcaA1 mRNA for RuBisCO activase large isoform precursor, complete cds. Published Jul. 4, 2000. pp. 1-2.*

Sharma et al. Involvement of a Ca2+-Dependent Protein Kinase Component Downstream to the Gibberellin-Binding Phosphoprotein, RuBisCO Activase, in Rice. Biochemical and Biophysical Research Communications. 2002. 290(2): 690-695.*

Salvucci, M.E. et al. "Relationship between the heat tolerance of photosynthesis and the thermal stability of rubisco activase in plants from contrasting thermal environments." Plant Physiology, Apr. 2004, vol. 134, pp. 1460-1470.

Scafaro, A.P. et al. "Physiological and molecular changes in *Oryza meridionalis* Ng., a heat-tolerant species of wild rice." Journal of Experimental Botany, 2010, vol. 61, No. 1, pp. 191-202.

Cao, Y. et al. "Influence of protein expression in rice leaves under heat stress." Acta Ecologica Sinica (Shengtai Xuebao), 2010, vol. 30, No. 22, pp. 6009-6018. Abstract Only.

Scafaro, A.P. et al. "Temperature response of mesophyll conductance in cultivated and wild *Oryza* species with contrasting mesophyll cell wall thickness." Plant, Cell & Environment, 2011, vol. 34, pp. 1999-2008.

Parry, M.A.J. et al. "Rubisco activity and regulation as targets for crop improvement." Journal of Experimental Botany, 2013, vol. 64, No. 3, pp. 717-730.

Atwell, B.J. et al. "Could abiotic stress tolerance in wild relatives of rice be used to improve *Oryza sativa*?" Plant Science, 2014, vol. 215-216, pp. 48-58.

International Search Report and Written Opinion; dated May 9, 2017 for PCT Application No. PCT/AU2016/000011.

Ichikawa, H. et al., "Genetic analyses of *Oryza* species by molecular markers for chloroplast genomes." Theoretical and Applied Genetics 72.3 (1986): 353-358.

Zhou, Yanhong et al., "Inhibition of photosynthesis and energy dissipation induced by water and high light stresses in rice." Journal of Experimental Botany 58.5 (2007): 1207-1217.

Keown, Jeremy R. et al., "Characterization of spinach ribulose-1, 5-bisphosphate carboxylase/oxygenase activase isoforms reveals hexameric assemblies with increased thermal stability." Biochemical Journal 464.3 (2014): 413-423.

* cited by examiner

SEQUENCE LISTING

<160> NUMBER OF SEQ ID NOS: 60

<210> SEQ ID NO 1
<211> LENGTH: 1302
<212> TYPE: DNA
<213> ORGANISM: Oryza sativa

<400> SEQUENCE: 1

```
atggctgctg ccttctcctc caccgttgga gctccggcgt ccactccgac caacttcctg      60
gggaagaagc tgaaaaagca ggtgacatcg gcggtgaact accatggcaa gagctccaac     120
atcaacaggt tcaaggtgat ggccaaggag ctggacgagg gcaagcagac cgaccaggac     180
aggtggaagg gtctcgccta cgacatctcc gatgaccagc aggacatcac caggggaag     240 ggtttcgtcg actccctttt ccaggctccc acgggtgatg gcacccacga ggccgtcctc     300
agctcctacg agtacctcag ccagggtctc agaacgtacg acttcgacaa caccatggga     360
ggcttctaca tcgcccctgc tttcatggac aagctcgtcg tccacatctc caagaacttc     420
atgaccctcc ccaacatcaa ggtcccactc atcctgggta tctggggagg caagggtcag     480
ggaaaatcct tccagtgtga gctcgtcttc gccaagatgg ggatcaaccc catcatgatg     540
agcgccggag agctggagag cggcaacgcc ggagagccgg cgaagctgat caggcagcgg     600
taccgtgagg cggcagacat catcaagaag gggaagatgt gctgcctctt catcaacgat     660
ctggacgcgg gtgcaggtcg catgggaggc accacccagt acacggtgaa caaccagatg     720
gtgaacgcca ccctgatgaa catcgccgac aacccaacca acgtgcagct ccccgggatg     780
tacaacaagg aggacaaccc ccgtgtcccc atcatcgtca ccggcaacga cttctccacg     840
ctgtacgcgc cgctcatccg tgacgggcgt atggagaagt tctactgggc tcccacccgc     900
gacgaccgtg tcggcgtctg caagggtatc ttccgcaccg acaacgtccc cgacgaggac     960
atcgtcaaga tcgtcgacag cttcccaggc caatccatcg atttcttcgg cgctcttcgt    1020
gcccgtgttt acgacgacga ggtgcgcaag tgggtgtcgg acacgggtgt ggagaacatt    1080
ggcaagaggc tggtgaactc gagggagggc ccaccggagt cgagcagcc caagatgacg    1140 atcgaaaagc tcatggagta cggatacatg cttgtgaagg agcaggagaa cgtcaagcgt    1200
```

```
gtgcagctgg ctgagcagta cttgagcgag gctgctcttg gtgacgctaa ctccgacgcc    1260
atgaagactg gttccttcta cggttctgcg ccatccagct ga                      1302
```

<210> SEQ ID NO 2
<211> LENGTH: 9
<212> TYPE: PRT
<213> ORGANISM: Oryza australiensis
<220> FEATURE:
<221> NAME/KEY: misc_feature
<222> LOCATION: (5)..(5)
<223> OTHER INFORMATION: Xaa can be any naturally occurring amino acid

<400> SEQUENCE: 2

```
Glu Leu Asp Glu Xaa Lys Gln Thr Asp
1               5
```

<210> SEQ ID NO 3
<211> LENGTH: 9
<212> TYPE: PRT
<213> ORGANISM: Oryza australiensis

<400> SEQUENCE: 3

```
Glu Leu Asp Glu Asp Lys Gln Thr Asp
1               5
```

<210> SEQ ID NO 4
<211> LENGTH: 9
<212> TYPE: PRT
<213> ORGANISM: Oryza australiensis

<400> SEQUENCE: 4

```
Thr Asp Gln Asp Lys Trp Lys Gly Leu
1               5
```

<210> SEQ ID NO 5
<211> LENGTH: 10
<212> TYPE: PRT
<213> ORGANISM: Oryza australiensis
<220> FEATURE:
<221> NAME/KEY: misc_feature
<222> LOCATION: (2)..(2)
<223> OTHER INFORMATION: Xaa can be any naturally occurring amino acid

<400> SEQUENCE: 5

```
Glu Xaa Lys Gln Thr Asp Gln Asp Lys Trp
1               5                   10
```

<210> SEQ ID NO 6
<211> LENGTH: 10
<212> TYPE: PRT
<213> ORGANISM: Oryza australiensis

<400> SEQUENCE: 6

```
Glu Asp Lys Gln Thr Asp Gln Asp Lys Trp
1               5                   10
```

<210> SEQ ID NO 7
<211> LENGTH: 9
<212> TYPE: PRT
<213> ORGANISM: Oryza australiensis
<220> FEATURE:
<221> NAME/KEY: misc_feature
<222> LOCATION: (5)..(5)
<223> OTHER INFORMATION: Xaa can be any naturally occurring amino acid

<400> SEQUENCE: 7

-continued

Arg Gly Lys Gly Xaa Val Asp Ser Leu
1               5

<210> SEQ ID NO 8
<211> LENGTH: 9
<212> TYPE: PRT
<213> ORGANISM: Oryza australiensis

<400> SEQUENCE: 8

Arg Gly Lys Gly Leu Val Asp Ser Leu
1               5

<210> SEQ ID NO 9
<211> LENGTH: 9
<212> TYPE: PRT
<213> ORGANISM: Oryza australiensis
<220> FEATURE:
<221> NAME/KEY: misc_feature
<222> LOCATION: (5)..(5)
<223> OTHER INFORMATION: Xaa can be any naturally occurring amino acid

<400> SEQUENCE: 9

Phe Gln Ala Pro Xaa Gly Asp Gly Thr
1               5

<210> SEQ ID NO 10
<211> LENGTH: 9
<212> TYPE: PRT
<213> ORGANISM: Oryza australiensis

<400> SEQUENCE: 10

Phe Gln Ala Pro Met Gly Asp Gly Thr
1               5

<210> SEQ ID NO 11
<211> LENGTH: 11
<212> TYPE: PRT
<213> ORGANISM: Oryza australiensis
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 11

Gly Xaa Val Asp Ser Leu Phe Gln Ala Pro Xaa
1               5                   10

<210> SEQ ID NO 12
<211> LENGTH: 11
<212> TYPE: PRT
<213> ORGANISM: Oryza australiensis

<400> SEQUENCE: 12

Gly Leu Val Asp Ser Leu Phe Gln Ala Pro Met
1               5                   10

<210> SEQ ID NO 13
<211> LENGTH: 8
<212> TYPE: PRT
<213> ORGANISM: Oryza australiensis

<400> SEQUENCE: 13

```
Glu Tyr Leu Ser Gln Gly Leu Lys
1               5

<210> SEQ ID NO 14
<211> LENGTH: 8
<212> TYPE: PRT
<213> ORGANISM: Oryza australiensis
<220> FEATURE:
<221> NAME/KEY: misc_feature
<222> LOCATION: (8)..(8)
<223> OTHER INFORMATION: Xaa can be any naturally occurring amino acid

<400> SEQUENCE: 14

Tyr Leu Ser Gln Gly Leu Lys Xaa
1               5

<210> SEQ ID NO 15
<211> LENGTH: 8
<212> TYPE: PRT
<213> ORGANISM: Oryza australiensis

<400> SEQUENCE: 15

Tyr Leu Ser Gln Gly Leu Lys Met
1               5

<210> SEQ ID NO 16
<211> LENGTH: 8
<212> TYPE: PRT
<213> ORGANISM: Oryza australiensis
<220> FEATURE:
<221> NAME/KEY: misc_feature
<222> LOCATION: (7)..(8)
<223> OTHER INFORMATION: Xaa can be any naturally occurring amino acid

<400> SEQUENCE: 16

Leu Ser Gln Gly Leu Lys Xaa Xaa
1               5

<210> SEQ ID NO 17
<211> LENGTH: 8
<212> TYPE: PRT
<213> ORGANISM: Oryza australiensis

<400> SEQUENCE: 17

Leu Ser Gln Gly Leu Lys Met Leu
1               5

<210> SEQ ID NO 18
<211> LENGTH: 11
<212> TYPE: PRT
<213> ORGANISM: Oryza australiensis
<220> FEATURE:
<221> NAME/KEY: misc_feature
<222> LOCATION: (2)..(3)
<223> OTHER INFORMATION: Xaa can be any naturally occurring amino acid

<400> SEQUENCE: 18

Lys Xaa Xaa Asp Asn Thr Met Gly Gly Phe Tyr
1               5                   10

<210> SEQ ID NO 19
<211> LENGTH: 11
<212> TYPE: PRT
<213> ORGANISM: Oryza australiensis

<400> SEQUENCE: 19

Lys Met Leu Asp Asn Thr Met Gly Gly Phe Tyr
```

<210> SEQ ID NO 20
<211> LENGTH: 11
<212> TYPE: PRT
<213> ORGANISM: Oryza australiensis
<220> FEATURE:
<221> NAME/KEY: misc_feature
<222> LOCATION: (1)..(2)
<223> OTHER INFORMATION: Xaa can be any naturally occurring amino acid

<400> SEQUENCE: 20

Xaa Xaa Asp Asn Thr Met Gly Gly Phe Tyr Ile
1               5                   10

<210> SEQ ID NO 21
<211> LENGTH: 11
<212> TYPE: PRT
<213> ORGANISM: Oryza australiensis

<400> SEQUENCE: 21

Met Leu Asp Asn Thr Met Gly Gly Phe Tyr Ile
1               5                   10

<210> SEQ ID NO 22
<211> LENGTH: 11
<212> TYPE: PRT
<213> ORGANISM: Oryza australiensis
<220> FEATURE:
<221> NAME/KEY: misc_feature
<222> LOCATION: (1)..(1)
<223> OTHER INFORMATION: Xaa can be any naturally occurring amino acid

<400> SEQUENCE: 22

Xaa Asp Asn Thr Met Gly Gly Phe Tyr Ile Ala
1               5                   10

<210> SEQ ID NO 23
<211> LENGTH: 11
<212> TYPE: PRT
<213> ORGANISM: Oryza australiensis

<400> SEQUENCE: 23

Leu Asp Asn Thr Met Gly Gly Phe Tyr Ile Ala
1               5                   10

<210> SEQ ID NO 24
<211> LENGTH: 11
<212> TYPE: PRT
<213> ORGANISM: Oryza australiensis
<220> FEATURE:
<221> NAME/KEY: misc_feature
<222> LOCATION: (6)..(7)
<223> OTHER INFORMATION: Xaa can be any naturally occurring amino acid

<400> SEQUENCE: 24

Ser Gln Gly Leu Lys Xaa Xaa Asp Asn Thr Met
1               5                   10

<210> SEQ ID NO 25
<211> LENGTH: 11
<212> TYPE: PRT
<213> ORGANISM: Oryza australiensis

<400> SEQUENCE: 25

Ser Gln Gly Leu Lys Met Leu Asp Asn Thr Met
1               5                   10

```
<210> SEQ ID NO 26
<211> LENGTH: 9
<212> TYPE: PRT
<213> ORGANISM: Oryza australiensis
<220> FEATURE:
<221> NAME/KEY: misc_feature
<222> LOCATION: (5)..(5)
<223> OTHER INFORMATION: Xaa can be any naturally occurring amino acid

<400> SEQUENCE: 26

Lys Asn Phe Met Xaa Leu Pro Asn Ile
1               5

<210> SEQ ID NO 27
<211> LENGTH: 9
<212> TYPE: PRT
<213> ORGANISM: Oryza australiensis

<400> SEQUENCE: 27

Lys Asn Phe Met Ala Leu Pro Asn Ile
1               5

<210> SEQ ID NO 28
<211> LENGTH: 9
<212> TYPE: PRT
<213> ORGANISM: Oryza australiensis

<400> SEQUENCE: 28

Glu Leu Val Phe Ser Lys Met Gly Ile
1               5

<210> SEQ ID NO 29
<211> LENGTH: 9
<212> TYPE: PRT
<213> ORGANISM: Oryza australiensis

<400> SEQUENCE: 29

Asn Ile Gly Lys Lys Leu Val Asn Ser
1               5

<210> SEQ ID NO 30
<211> LENGTH: 9
<212> TYPE: PRT
<213> ORGANISM: Oryza australiensis

<400> SEQUENCE: 30

Lys Met Thr Ile Asp Lys Leu Met Glu
1               5

<210> SEQ ID NO 31
<211> LENGTH: 8
<212> TYPE: PRT
<213> ORGANISM: Oryza australiensis

<400> SEQUENCE: 31

Met Glu Tyr Gly His Met Leu Tyr
1               5

<210> SEQ ID NO 32
<211> LENGTH: 8
<212> TYPE: PRT
<213> ORGANISM: Oryza australiensis

<400> SEQUENCE: 32
```

-continued

```
Met Leu Val Arg Glu Gln Glu Asn
1               5

<210> SEQ ID NO 33
<211> LENGTH: 12
<212> TYPE: PRT
<213> ORGANISM: Oryza australiensis

<400> SEQUENCE: 33

Asp Lys Leu Met Glu Tyr Gly His Met Leu Val Arg
1               5                   10

<210> SEQ ID NO 34
<211> LENGTH: 9
<212> TYPE: PRT
<213> ORGANISM: Oryza australiensis

<400> SEQUENCE: 34

Asn Val Lys Arg Val Gln Leu Ala Asp
1               5

<210> SEQ ID NO 35
<211> LENGTH: 9
<212> TYPE: PRT
<213> ORGANISM: Oryza australiensis

<400> SEQUENCE: 35

Lys Tyr Leu Ser Glu Ala Ala Leu Gly
1               5

<210> SEQ ID NO 36
<211> LENGTH: 10
<212> TYPE: PRT
<213> ORGANISM: Oryza australiensis

<400> SEQUENCE: 36

Val Gln Leu Ala Asp Lys Tyr Leu Ser Glu
1               5                   10

<210> SEQ ID NO 37
<211> LENGTH: 9
<212> TYPE: PRT
<213> ORGANISM: Oryza australiensis

<400> SEQUENCE: 37

Gly Ala Gln Gln Gly Gly Asn Leu Pro
1               5

<210> SEQ ID NO 38
<211> LENGTH: 433
<212> TYPE: PRT
<213> ORGANISM: Oryza sativa

<400> SEQUENCE: 38

Met Ala Ala Ala Phe Ser Ser Thr Val Gly Ala Pro Ala Ser Thr Pro
1               5                   10                  15

Thr Asn Phe Leu Gly Lys Lys Leu Lys Lys Gln Val Thr Ser Ala Val
            20                  25                  30

Asn Tyr His Gly Lys Ser Ser Asn Ile Asn Arg Phe Lys Val Met Ala
        35                  40                  45

Lys Glu Leu Asp Glu Gly Lys Gln Thr Asp Gln Asp Arg Trp Lys Gly
    50                  55                  60

Leu Ala Tyr Asp Ile Ser Asp Asp Gln Gln Asp Ile Thr Arg Gly Lys
```

```
                65                   70                   75                   80
Gly Phe Val Asp Ser Leu Phe Gln Ala Pro Thr Gly Asp Gly Thr His
                    85                   90                   95
Glu Ala Val Leu Ser Ser Tyr Glu Tyr Leu Ser Gln Gly Leu Arg Thr
                    100                  105                 110
Tyr Asp Phe Asp Asn Thr Met Gly Phe Tyr Ile Ala Pro Ala Phe
                    115                  120                 125
Met Asp Lys Leu Val Val His Ile Ser Lys Asn Phe Met Thr Leu Pro
            130                 135                 140
Asn Ile Lys Val Pro Leu Ile Leu Gly Ile Trp Gly Lys Gly Gln
145                 150                 155                 160
Gly Lys Ser Phe Gln Cys Glu Leu Val Phe Ala Lys Met Gly Ile Asn
                    165                 170                 175
Pro Ile Met Met Ser Ala Gly Glu Leu Glu Ser Gly Asn Ala Gly Glu
            180                 185                 190
Pro Ala Lys Leu Ile Arg Gln Arg Tyr Arg Glu Ala Ala Asp Ile Ile
            195                 200                 205
Lys Lys Gly Lys Met Cys Cys Leu Phe Ile Asn Asp Leu Asp Ala Gly
210                 215                 220
Ala Gly Arg Met Gly Gly Thr Thr Gln Tyr Thr Val Asn Asn Gln Met
225                 230                 235                 240
Val Asn Ala Thr Leu Met Asn Ile Ala Asp Asn Pro Thr Asn Val Gln
                    245                 250                 255
Leu Pro Gly Met Tyr Asn Lys Glu Asp Asn Pro Arg Val Pro Ile Ile
            260                 265                 270
Val Thr Gly Asn Asp Phe Ser Thr Leu Tyr Ala Pro Leu Ile Arg Asp
            275                 280                 285
Gly Arg Met Glu Lys Phe Tyr Trp Ala Pro Thr Arg Asp Asp Arg Val
            290                 295                 300
Gly Val Cys Lys Gly Ile Phe Arg Thr Asp Asn Val Pro Asp Glu Asp
305                 310                 315                 320
Ile Val Lys Ile Val Asp Ser Phe Pro Gly Gln Ser Ile Asp Phe Phe
                    325                 330                 335
Gly Ala Leu Arg Ala Arg Val Tyr Asp Asp Glu Val Arg Lys Trp Val
            340                 345                 350
Ser Asp Thr Gly Val Glu Asn Ile Gly Lys Arg Leu Val Asn Ser Arg
            355                 360                 365
Glu Gly Pro Pro Glu Phe Glu Gln Pro Lys Met Thr Ile Glu Lys Leu
    370                 375                 380
Met Glu Tyr Gly Tyr Met Leu Val Lys Glu Gln Glu Asn Val Lys Arg
385                 390                 395                 400
Val Gln Leu Ala Glu Gln Tyr Leu Ser Glu Ala Leu Gly Asp Ala
            405                 410                 415
Asn Ser Asp Ala Met Lys Thr Gly Ser Phe Tyr Gly Ser Ala Pro Ser
            420                 425                 430
Ser

<210> SEQ ID NO 39
<211> LENGTH: 464
<212> TYPE: PRT
<213> ORGANISM: Oryza australiensis

<400> SEQUENCE: 39

Met Ala Ala Ala Phe Ser Ser Thr Val Gly Ala Pro Ala Ser Thr Pro
```

-continued

```
1               5                   10                  15
Thr Asn Phe Leu Gly Lys Lys Leu Lys Lys Gln Val Thr Ser Ala Val
                20                  25                  30
Asn Tyr His Gly Lys Ser Ser Asn Ile Asn Arg Phe Lys Val Met Ala
                35                  40                  45
Lys Glu Leu Asp Glu Asp Lys Gln Thr Asp Gln Asp Lys Trp Lys Gly
                50                  55                  60
Leu Ala Tyr Asp Ile Ser Asp Asp Gln Gln Asp Ile Thr Arg Gly Lys
65                  70                  75                  80
Gly Leu Val Asp Ser Leu Phe Gln Ala Pro Met Gly Asp Gly Thr His
                85                  90                  95
Glu Ala Val Leu Ser Ser Tyr Glu Tyr Leu Ser Gln Gly Leu Lys Met
                100                 105                 110
Leu Asp Asn Thr Met Gly Gly Phe Tyr Ile Ala Pro Ala Phe Met Asp
                115                 120                 125
Lys Leu Val Val His Ile Ser Lys Asn Phe Met Ala Leu Pro Asn Ile
                130                 135                 140
Lys Val Pro Leu Ile Leu Gly Ile Trp Gly Lys Gly Gln Gly Lys
145                 150                 155                 160
Ser Phe Gln Cys Glu Leu Val Phe Ser Lys Met Gly Ile Asn Pro Ile
                165                 170                 175
Met Met Ser Ala Gly Glu Leu Glu Ser Gly Asn Ala Gly Glu Pro Ala
                180                 185                 190
Lys Leu Ile Arg Gln Arg Tyr Arg Glu Ala Ala Asp Ile Ile Lys Lys
                195                 200                 205
Gly Lys Met Cys Cys Leu Phe Ile Asn Asp Leu Asp Ala Gly Ala Gly
                210                 215                 220
Arg Met Gly Gly Thr Thr Gln Tyr Thr Val Asn Asn Gln Met Val Asn
225                 230                 235                 240
Ala Thr Leu Met Asn Ile Ala Asp Asn Pro Thr Asn Val Gln Leu Pro
                245                 250                 255
Gly Met Tyr Asn Lys Glu Asp Asn Pro Arg Val Pro Ile Ile Val Thr
                260                 265                 270
Gly Asn Asp Phe Ser Thr Leu Tyr Ala Pro Leu Ile Arg Asp Gly Arg
                275                 280                 285
Met Glu Lys Phe Tyr Trp Ala Pro Thr Arg Asp Asp Arg Val Gly Val
                290                 295                 300
Cys Lys Gly Ile Phe Arg Thr Asp Asn Val Pro Asp Glu Asp Ile Val
305                 310                 315                 320
Lys Ile Val Asp Ser Phe Pro Gly Gln Ser Ile Asp Phe Phe Gly Ala
                325                 330                 335
Leu Arg Ala Arg Val Tyr Asp Asp Glu Val Arg Lys Trp Val Ser Asp
                340                 345                 350
Thr Gly Val Glu Asn Ile Gly Lys Lys Leu Val Asn Ser Arg Glu Gly
                355                 360                 365
Pro Pro Glu Phe Glu Gln Pro Lys Met Thr Ile Asp Lys Leu Met Glu
                370                 375                 380
Tyr Gly His Met Leu Val Arg Glu Gln Glu Asn Val Lys Arg Val Gln
385                 390                 395                 400
Leu Ala Asp Lys Tyr Leu Ser Glu Ala Ala Leu Gly Asp Ala Asn Ser
                405                 410                 415
Asp Ala Met Lys Thr Gly Ser Phe Tyr Gly Gln Gly Ala Gln Gln Gly
                420                 425                 430
```

```
Gly Asn Leu Pro Val Pro Glu Gly Cys Thr Asp Pro Val Ala Lys Asn
            435                 440                 445

Phe Asp Pro Thr Ala Arg Ser Asp Asp Gly Ser Cys Leu Tyr Thr Phe
450                 455                 460
```

<210> SEQ ID NO 40
<211> LENGTH: 431
<212> TYPE: PRT
<213> ORGANISM: Oryza australiensis

<400> SEQUENCE: 40

```
Met Ala Ala Ala Phe Ser Ser Thr Val Gly Pro Ala Ser Thr Pro
1               5                   10                  15

Thr Asn Phe Leu Gly Lys Lys Leu Lys Lys Gln Val Thr Ser Ala Val
                20                  25                  30

Asn Tyr His Gly Lys Ser Ser Asn Ile Asn Arg Phe Lys Val Met Ala
            35                  40                  45

Lys Glu Leu Asp Glu Asp Lys Gln Thr Asp Gln Asp Lys Trp Lys Gly
50                  55                  60

Leu Ala Tyr Asp Ile Ser Asp Asp Gln Gln Asp Ile Thr Arg Gly Lys
65                  70                  75                  80

Gly Leu Val Asp Ser Leu Phe Gln Ala Pro Met Gly Asp Gly Thr His
                85                  90                  95

Glu Ala Val Leu Ser Ser Tyr Glu Tyr Leu Ser Gln Gly Leu Lys Met
            100                 105                 110

Leu Asp Asn Thr Met Gly Gly Phe Tyr Ile Ala Pro Ala Phe Met Asp
        115                 120                 125

Lys Leu Val Val His Ile Ser Lys Asn Phe Met Ala Leu Pro Asn Ile
130                 135                 140

Lys Val Pro Leu Ile Leu Gly Ile Trp Gly Gly Lys Gly Gln Gly Lys
145                 150                 155                 160

Ser Phe Gln Cys Glu Leu Val Phe Ser Lys Met Gly Ile Asn Pro Ile
                165                 170                 175

Met Met Ser Ala Gly Glu Leu Glu Ser Gly Asn Ala Gly Glu Pro Ala
            180                 185                 190

Lys Leu Ile Arg Gln Arg Tyr Arg Glu Ala Ala Asp Ile Ile Lys Lys
        195                 200                 205

Gly Lys Met Cys Cys Leu Phe Ile Asn Asp Leu Asp Ala Gly Ala Gly
210                 215                 220

Arg Met Gly Gly Thr Thr Gln Tyr Thr Val Asn Asn Gln Met Val Asn
225                 230                 235                 240

Ala Thr Leu Met Asn Ile Ala Asp Asn Pro Thr Asn Val Gln Leu Pro
                245                 250                 255

Gly Met Tyr Asn Lys Glu Asp Asn Pro Arg Val Pro Ile Ile Val Thr
            260                 265                 270

Gly Asn Asp Phe Ser Thr Leu Tyr Ala Pro Leu Ile Arg Asp Gly Arg
        275                 280                 285

Met Glu Lys Phe Tyr Trp Ala Pro Thr Arg Asp Asp Arg Val Gly Val
290                 295                 300

Cys Lys Gly Ile Phe Arg Thr Asp Asn Val Pro Asp Glu Asp Ile Val
305                 310                 315                 320

Lys Ile Val Asp Ser Phe Pro Gly Gln Ser Ile Asp Phe Phe Gly Ala
                325                 330                 335

Leu Arg Ala Arg Val Tyr Asp Asp Glu Val Arg Lys Trp Val Ser Asp
```

```
              340             345             350
Thr Gly Val Glu Asn Ile Gly Lys Lys Leu Val Asn Ser Arg Glu Gly
            355             360             365

Pro Pro Glu Phe Glu Gln Pro Lys Met Thr Ile Asp Lys Leu Met Glu
        370             375             380

Tyr Gly His Met Leu Val Arg Glu Gln Glu Asn Val Lys Arg Val Gln
385             390             395             400

Leu Ala Asp Lys Tyr Leu Ser Glu Ala Ala Leu Gly Asp Ala Asn Ser
                405             410             415

Asp Ala Met Lys Thr Gly Ser Phe Tyr Gly Ala Ala Pro Ser Ser
            420             425             430
```

<210> SEQ ID NO 41
<211> LENGTH: 1296
<212> TYPE: DNA
<213> ORGANISM: Oryza australiensis

<400> SEQUENCE: 41

```
atggctgctg ccttctcctc caccgttgga gctccggcct ccactccgac caacttcctg     60
gggaagaagc tgaagaagca ggtgacatcg gccgtgaact accatggcaa gagctccaac    120
atcaacaggt tcaaagtgat ggccaaggag ctcgacgagg acaagcagac cgaccaggac    180
aagtggaagg gtctcgccta cgacatctcc gatgaccagc aggacatcac caggggaag     240
ggtctcgtcg actccctctt ccaggctccc atgggtgatg gcacccacga ggccgtcctc    300
agctcctacg agtacctcag ccagggtctc aaaatgttgg acaacaccat gggaggcttc    360
tacatcgccc cggctttcat ggacaagctc gtcgtccaca tctccaagaa cttcatggcc    420
ctccccaaca tcaaggtccc actcatcctg ggtatctggg gaggcaaggg tcagggaaaa    480
tccttccagt gtgagctcgt cttctccaag atggggatca ccccatcat gatgagtgcc     540
ggagagctgg agagcggcaa cgccggagag cccgcgaagc tcatcaggca gcggtatcgt    600
gaggcggcgg acatcatcaa gaaggggaag atgtgctgcc tcttcatcaa cgatctcgac    660
gccggagcag gtcgcatggg cggcaccacc cagtacacgg tgaacaacca gatggtgaac    720
gccacccctga tgaacatcgc cgacaaccca accaacgtgc agctgccggg catgtacaac    780
aaggaggaca ccccgtgt ccccatcatc gtcaccggta cgacttctc gacgctgtac         840
gcgccgctca tccgtgacgg gcgtatggag aagttctact gggctccac ccgcgatgac       900
cgtgtcggcg tctgcaaggg tatcttccgc accgacaacg tccccgacga ggacatcgtc    960
aaaatcgtgg acagcttccc aggccaatcc atcgatttct tcggtgctct gcgtgcccgt   1020
gtttacgacg acgaggtgcg caagtgggtg tcggacaccg tgtggagaa cattggcaag    1080
aagctggtga actcgaggga gggccaccg gagttcgagc agcccaagat gacgatcgac    1140
aagctgatgg agtacggaca catgcttgtg agggagcagg agaacgtcaa gcgtgtgcag    1200
ctggctgaca gtacttgag cgaggctgct cttggtgacg ctaactccga cgccatgaag    1260
actggttcct tctacggtgc tgcgccatcc agctga                              1296
```

<210> SEQ ID NO 42
<211> LENGTH: 1395
<212> TYPE: DNA
<213> ORGANISM: Oryza australiensis

<400> SEQUENCE: 42

```
atggctgctg ccttctcctc caccgttgga gctccggcct ccactccgac caacttcctg     60
```

| | | |
|---|---|---|
| gggaagaagc tgaagaagca ggtgacatcg ccgtgaact accatggcaa gagctccaac | 120 | |
| atcaacaggt tcaaagtgat ggccaaggag ctcgacgagg acaagcagac cgaccaggac | 180 | |
| aagtggaagg gtctcgccta cgacatctcc gatgaccagc aggacatcac cagggggaag | 240 | |
| ggtctcgtcg actccctctt ccaggctccc atgggtgatg cacccacga ggccgtcctc | 300 | |
| agctcctacg agtacctcag ccagggtctc aaaatgttgg acaacaccat gggaggcttc | 360 | |
| tacatcgccc cggctttcat ggacaagctc gtcgtccaca tctccaagaa cttcatggcc | 420 | |
| ctccccaaca tcaaggtccc actcatcctg ggtatctggg gaggcaaggg tcagggaaaa | 480 | |
| tccttccagt gtgagctcgt cttctccaag atggggatca accccatcat gatgagtgcc | 540 | |
| ggagagctgg agagcggcaa cgccggagag cccgcgaagc tcatcaggca gcggtatcgt | 600 | |
| gaggcggcgg acatcatcaa gaaggggaag atgtgctgcc tcttcatcaa cgatctcgac | 660 | |
| gccggagcag gtcgcatggg cggcaccacc cagtacacgg tgaacaacca gatggtgaac | 720 | |
| gccaccctga tgaacatcgc cgacaaccca accaacgtgc agctgccggg catgtacaac | 780 | |
| aaggaggaca ccccccgtgt ccccatcatc gtcaccggta cgacttctc gacgctgtac | 840 | |
| gcgccgctca tccgtgacgg gcgtatggag aagttctact gggctcccac ccgcgatgac | 900 | |
| cgtgtcggcg tctgcaaggg tatcttccgc accgacaacg tccccgacga ggacatcgtc | 960 | |
| aaaatcgtgg acagcttccc aggccaatcc atcgatttct tcggtgctct gcgtgcccgt | 1020 | |
| gtttacgacg acgaggtgcg caagtgggtg tcggacaccg tgtgtggagaa cattggcaag | 1080 | |
| aagctggtga actcgaggga gggcccaccg gagttcgagc agcccaagat gacgatcgac | 1140 | |
| aagctgatgg agtacggaca catgcttgtg agggagcagg agaacgtcaa gcgtgtgcag | 1200 | |
| ctggctgaca agtacttgag cgaggctgct cttggtgacg ctaactccga cgccatgaag | 1260 | |
| actggttcct tctacgggca aggagcacag caaggaggta acctgcctgt gccggaaggt | 1320 | |
| tgcaccgacc ctgttgccaa gaacttcgac ccaacggcga ggagcgacga cggcagctgc | 1380 | |
| ctttacacct tttaa | 1395 | |

<210> SEQ ID NO 43
<211> LENGTH: 466
<212> TYPE: PRT
<213> ORGANISM: Oryza sativa

<400> SEQUENCE: 43

```
Met Ala Ala Ala Phe Ser Ser Thr Val Gly Ala Pro Ala Ser Thr Pro
1               5                  10                  15

Thr Asn Phe Leu Gly Lys Lys Leu Lys Lys Gln Val Thr Ser Ala Val
            20                  25                  30

Asn Tyr His Gly Lys Ser Ser Asn Ile Asn Arg Phe Lys Val Met Ala
        35                  40                  45

Lys Glu Leu Asp Glu Gly Lys Gln Thr Asp Gln Asp Arg Trp Lys Gly
    50                  55                  60

Leu Ala Tyr Asp Ile Ser Asp Asp Gln Gln Asp Ile Thr Arg Gly Lys
65                  70                  75                  80

Gly Phe Val Asp Ser Leu Phe Gln Ala Pro Thr Gly Asp Gly Thr His
                85                  90                  95

Glu Ala Val Leu Ser Ser Tyr Glu Tyr Leu Ser Gln Gly Leu Arg Thr
            100                 105                 110

Tyr Asp Phe Asp Asn Thr Met Gly Gly Phe Tyr Ile Ala Pro Ala Phe
        115                 120                 125

Met Asp Lys Leu Val Val His Ile Ser Lys Asn Phe Met Thr Leu Pro
```

```
    Asn Ile Lys Val Pro Leu Ile Leu Gly Ile Trp Gly Gly Lys Gly Gln
    145                 150                 155                 160

Gly Lys Ser Phe Gln Cys Glu Leu Val Phe Ala Lys Met Gly Ile Asn
                    165                 170                 175

Pro Ile Met Met Ser Ala Gly Glu Leu Glu Ser Gly Asn Ala Gly Glu
                180                 185                 190

Pro Ala Lys Leu Ile Arg Gln Arg Tyr Arg Glu Ala Ala Asp Ile Ile
                195                 200                 205

Lys Lys Gly Lys Met Cys Cys Leu Phe Ile Asn Asp Leu Asp Ala Gly
        210                 215                 220

Ala Gly Arg Met Gly Gly Thr Thr Gln Tyr Thr Val Asn Asn Gln Met
    225                 230                 235                 240

Val Asn Ala Thr Leu Met Asn Ile Ala Asp Asn Pro Thr Asn Val Gln
                    245                 250                 255

Leu Pro Gly Met Tyr Asn Lys Glu Asp Asn Pro Arg Val Pro Ile Ile
                260                 265                 270

Val Thr Gly Asn Asp Phe Ser Thr Leu Tyr Ala Pro Leu Ile Arg Asp
                275                 280                 285

Gly Arg Met Glu Lys Phe Tyr Trp Ala Pro Thr Arg Asp Asp Arg Val
        290                 295                 300

Gly Val Cys Lys Gly Ile Phe Arg Thr Asp Asn Val Pro Asp Glu Asp
    305                 310                 315                 320

Ile Val Lys Ile Val Asp Ser Phe Pro Gly Gln Ser Ile Asp Phe Phe
                    325                 330                 335

Gly Ala Leu Arg Ala Arg Val Tyr Asp Asp Glu Val Arg Lys Trp Val
                340                 345                 350

Ser Asp Thr Gly Val Glu Asn Ile Gly Lys Arg Leu Val Asn Ser Arg
                355                 360                 365

Glu Gly Pro Pro Glu Phe Glu Gln Pro Lys Met Thr Ile Glu Lys Leu
        370                 375                 380

Met Glu Tyr Gly Tyr Met Leu Val Lys Glu Gln Glu Asn Val Lys Arg
    385                 390                 395                 400

Val Gln Leu Ala Glu Gln Tyr Leu Ser Glu Ala Leu Gly Asp Ala
                    405                 410                 415

Asn Ser Asp Ala Met Lys Thr Gly Ser Phe Tyr Gly Gln Gly Ala Gln
                420                 425                 430

Gln Ala Gly Asn Leu Pro Val Pro Glu Gly Cys Thr Asp Pro Val Ala
        435                 440                 445

Lys Asn Phe Asp Pro Thr Ala Arg Ser Asp Asp Gly Ser Cys Leu Tyr
    450                 455                 460

Thr Phe
    465

<210> SEQ ID NO 44
<211> LENGTH: 1401
<212> TYPE: DNA
<213> ORGANISM: Oryza sativa

<400> SEQUENCE: 44
atggctgctg ccttctcctc caccgttgga gctccggcgt ccactccgac caacttcctg    60
gggaagaagc tgaagaagca ggtgacatcg gcggtgaact accatggcaa gagctccaac   120
atcaacaggt tcaaggtgat ggccaaggag ctggacgagg caagcagac cgaccaggac   180
```

-continued

```
aggtggaagg gtctcgccta cgacatctcc gatgaccagc aggacatcac caggggaag       240 ggtttcgtcg actcccttt ccaggctccc acgggtgatg caccacga ggccgtcctc         300 agctcctacg agtacctcag ccagggtctc agaacgtacg acttcgacaa caccatggga     360
ggcttctaca tcgcccctgc tttcatggac aagctcgtcg tccacatctc caagaacttc     420
atgaccctcc ccaacatcaa ggtcccactc atcctgggta tctggggagg caagggtcag     480
ggaaaatcct tccagtgtga gctcgtcttc gccaagatgg ggatcaaccc catcatgatg     540
agcgccggag agctggagag cggcaacgcc ggagagccgg cgaagctgat caggcagcgg     600
taccgtgagg cggcagacat catcaagaag gggaagatgt gctgcctctt catcaacgat     660
ctggacgcgg gtgcaggtcg catgggaggc accacccagt acacggtgaa caaccagatg     720
gtgaacgcca ccctgatgaa catcgccgac aacccaacca acgtgcagct ccccgggatg     780
tacaacaagg aggacaaccc ccgtgtcccc atcatcgtca ccggcaacga cttctccacg     840
ctgtacgcgc cgctcatccg tgacgggcgt atggagaagt tctactgggc tcccacccgc     900
gacgaccgtg tcggcgtctg caagggtatc ttccgcaccg acaacgtccc cgacgaggac     960
atcgtcaaga tcgtcgacag cttcccaggc caatccatcg atttcttcgg cgctcttcgt    1020
gcccgtgttt acgacgacga ggtgcgcaag tgggtgtcgg acacgggtgt ggagaacatt    1080
ggcaagaggc tggtgaactc gagggagggc ccaccggagt tcgagcagcc aagatgacg     1140 atcgaaaagc tcatggagta cggatacatg cttgtgaagg agcaggagaa cgtcaagcgt    1200
gtgcagctgg ctgagcagta cttgagcgag gctgctcttg gtgacgctaa ctccgacgcc    1260
atgaagactg gttccttcta cgggcaagga gcacagcaag caggtaacct gcctgtgccg    1320
gaaggttgca ccgaccctgt tgccaagaac ttcgacccaa cggcgaggag cgacgacggc    1380
agctgccttt acaccttta a                                                1401
```

<210> SEQ ID NO 45
<211> LENGTH: 9
<212> TYPE: PRT
<213> ORGANISM: Oryza australiensis

<400> SEQUENCE: 45

Ser Phe Tyr Gly Ala Ala Pro Ser Ser
1               5

<210> SEQ ID NO 46
<211> LENGTH: 1263
<212> TYPE: DNA
<213> ORGANISM: Oryza sativa

<400> SEQUENCE: 46

```
atggctaaag aactggacga aggcaaacag actgatcagg accgctggaa aggtctggcc        60
tacgatattt ccgatgacca gcaggatatc cccgcggta aaggcttcgt agattctctg       120
ttccaggcgc caactggtga tggtactcat gaagcggttc tgagctccta cgaatatctg       180
agccagggtc tgcgtaccta tgacttcgac aacactatgg gcggttttta catcgctccg       240
gctttcatgg acaaactggt cgtccacatc tccaaaaact tcatgaccct gccgaacatc       300
aaagtgccac tgattctcgg catctggggt ggcaaaggtc aggcaaatc cttccagtgt       360 gaactggtct tcgcgaaaat gggcattaac ccgatcatga tgagcgcagg tgaactggaa       420
tctggtaacg ccggtgaacc ggcgaaactg attcgtcagc gttaccgtga agcggccgac       480
atcatcaaaa aaggcaaaat gtgctgcctg ttcatcaacg atctggatgc tggtgcaggt       540
```

| | |
|---|---|
| cgtatgggtg gcactaccca gtataccgtg aacaaccaga tggttaacgc caccctgatg | 600 |
| aacattgccg ataacccgac taacgtacag ctgccgggca tgtataacaa agaagacaac | 660 |
| ccgcgcgttc cgatcattgt taccggcaac gacttctcta cgctgtatgc tccgctgatt | 720 |
| cgtgatggcc gtatggagaa attctactgg gcaccaaccc gtgacgaccg tgttggtgta | 780 |
| tgcaaaggta tcttccgcac cgataacgtt ccggacgaag acatcgtcaa atcgtggac | 840 |
| agctttccgg ccagtctat cgatttcttt ggcgctctgc gtgctcgtgt ttacgacgac | 900 |
| gaagttcgca atgggtgtc tgatacgggt gtggaaaaca tcggcaaacg tctggttaac | 960 |
| tctcgtgaag gtccaccgga gttcgaacag ccgaaaatga cgatcgagaa actgatggag | 1020 |
| tacggctaca tgctggtgaa agagcaggag aacgtgaaac gtgtacagct ggcagaacag | 1080 |
| tacctgagcg aagctgcact gggtgatgcg aactctgacg cgatgaaaac tggctccttt | 1140 |
| tatggtcagg gtgcacagca ggcaggtaac ctcccagtac cagaaggttg taccgaccca | 1200 |
| gttgcgaaaa actttgaccc aaccgctcgc tctgatgacg gttcttgcct gtacaccttc | 1260 |
| taa | 1263 |

<210> SEQ ID NO 47
<211> LENGTH: 1266
<212> TYPE: DNA
<213> ORGANISM: Oryza australiensis

<400> SEQUENCE: 47

| | |
|---|---|
| atggccaaag aactggacga agacaaacag accgaccagg acaaatggaa aggtctggcg | 60 |
| tacgacatct ctgatgacca gcaggatatc acccgtggca aaggcctggt agattctctg | 120 |
| ttccaggctc cgatgggtga tggtactcat gaggcggttc tgtcttccta tgagtacctg | 180 |
| agccagggcc tgaaaatgct ggataacact atgggtggct tctacattgc accggccttt | 240 |
| atggacaaac tggtcgtcca catctccaaa aacttcatgg ccctgccgaa catcaaagtc | 300 |
| ccgctgattc tgggtatttg gggtggcaaa ggtcagggca atccttcca gtgcgaactg | 360 |
| gtcttcagca aaatgggcat caacccgatc atgatgagcg ctggtgaact ggaatctggt | 420 |
| aacgctggcg aaccggctaa actgattcgt cagcgttacc gcgaagcggc cgacatcatc | 480 |
| aaaaaaggca aaatgtgctg cctgttcatc aacgatctgg atgcaggtgc aggtcgtatg | 540 |
| ggtggcacta cccagtatac cgtgaacaac cagatggtga acgcgaccct gatgaacatc | 600 |
| gcggataacc caaccaacgt tcagctgccg ggcatgtaca caaagaaga caacccgcgt | 660 |
| gtcccgatta cgttaccgg caacgacttc tccactctct atgctccgct gatccgtgac | 720 |
| ggccgtatgg aaaaattcta ctgggcaccg actcgcgacg atcgtgtagg cgtgtgtaaa | 780 |
| ggtatcttcc gtaccgacaa cgtcccgac gaggacattg tgaaaatcgt ggacagcttt | 840 |
| ccgggccagt ctattgattt ctttggcgct ctgcgtgcac gtgtatacga cgatgaagtc | 900 |
| cgcaaatggg ttagcgacac gggtgttgag aacatcggca aaaactggt gaactcccgt | 960 |
| gaaggtccac cggaatttga gcagccgaaa atgacgatca caaactgat ggagtacggt | 1020 |
| cacatgctgg tacgcgaaca ggaaaacgtg aaacgtgtgc agctggcgga taaatacctg | 1080 |
| agcgaagcag ctctgggtga tgctaactcc gatgcgatga aaaccggctc tttctatggt | 1140 |
| cagggtgcac agcagggcgg taacctgcca gtaccggaag gttgtactga tccggttgcg | 1200 |
| aaaaacttcg atccaacggc tcgctctgat gacggttctt gcctctatac ctttgcgggt | 1260 |
| cgctaa | 1266 |

<210> SEQ ID NO 48
<211> LENGTH: 1164
<212> TYPE: DNA
<213> ORGANISM: Oryza sativa

<400> SEQUENCE: 48

| | | | | | |
|---|---|---|---|---|---|
| atggctaaag | aactggacga | aggcaaacag | actgatcagg | accgctggaa | aggtctggcc | 60 |
| tacgatattt | ccgatgacca | gcaggatatc | acccgcggta | aaggcttcgt | agattctctg | 120 |
| ttccaggcgc | caactggtga | tggtactcat | gaagcggttc | tgagctccta | cgaatatctg | 180 |
| agccagggtc | tgcgtaccta | tgacttcgac | aacactatgg | gcggttttta | catcgctccg | 240 |
| gctttcatgg | acaaactggt | cgtccacatc | tccaaaaact | tcatgaccct | gccgaacatc | 300 |
| aaagtgccac | tgattctcgg | catctggggt | ggcaaaggtc | agggcaaatc | cttccagtgt | 360 |
| gaactggtct | tcgcgaaaat | ggcattaacc | ccgatcatga | tgagcgcagg | tgaactggaa | 420 |
| tctggtaacg | ccggtgaacc | ggcgaaactg | attcgtcagc | gttaccgtga | agcggccgac | 480 |
| atcatcaaaa | aagcaaaat | gtgctgcctg | ttcatcaacg | atctggatgc | tggtgcaggt | 540 |
| cgtatgggtg | gcactaccca | gtataccgtg | aacaaccaga | tggttaacgc | caccctgatg | 600 |
| aacattgccg | ataacccgac | taacgtacag | ctgccgggca | tgtataacaa | agaagacaac | 660 |
| ccgcgcgttc | cgatcattgt | taccggcaac | gacttctcta | cgctgtatgc | tccgctgatt | 720 |
| cgtgatggcc | gtatggagaa | attctactgg | gcaccaaccc | gtgacgaccg | tgttggtgta | 780 |
| tgcaaaggta | tcttccgcac | cgataacgtt | ccggacgaag | acatcgtcaa | aatcgtggac | 840 |
| agctttccgg | ccagtctat | cgatttcttt | ggcgctctgc | gtgctcgtgt | ttacgacgac | 900 |
| gaagttcgca | atgggtgtc | tgatacgggt | gtggaaaaca | tcggcaaacg | tctggttaac | 960 |
| tctcgtgaag | gtccaccgga | gttcgaacag | ccgaaaatga | cgatcgagaa | actgatggag | 1020 |
| tacggctaca | tgctggtgaa | agagcaggag | aacgtgaaac | gtgtacagct | ggcagaacag | 1080 |
| tacctgagcg | aagctgcact | gggtgatgcg | aactctgacg | cgatgaaaac | tggctccttt | 1140 |
| tatggttccg | cgccgtcttc | ctaa | | | | 1164 |

<210> SEQ ID NO 49
<211> LENGTH: 1158
<212> TYPE: DNA
<213> ORGANISM: Oryza australiensis

<400> SEQUENCE: 49

| | | | | | |
|---|---|---|---|---|---|
| atggccaaag | aactggacga | agacaaacag | accgaccagg | acaaatggaa | aggtctggcg | 60 |
| tacgacatct | ctgatgacca | gcaggatatc | acccgtggca | aaggcctggt | agattctctg | 120 |
| ttccaggctc | cgatgggtga | tggtactcat | gaggcggttc | tgtcttccta | tgagtacctg | 180 |
| agccagggcc | tgaaaatgct | ggataacact | atgggtggct | tctacattgc | accggccttt | 240 |
| atggacaaac | tggtcgtcca | catctccaaa | aacttcatgg | ccctgccgaa | catcaaagtc | 300 |
| ccgctgattc | tgggtatttg | gggtggcaaa | ggtcagggca | atccttcca | gtgcgaactg | 360 |
| gtcttcagca | aaatgggcat | caacccgatc | atgatgagcg | ctggtgaact | ggaatctggt | 420 |
| aacgctggcg | aaccggctaa | actgattcgt | cagcgttacc | gcgaagcggc | cgacatcatc | 480 |
| aaaaaaggca | aatgtgctg | cctgttcatc | aacgatctgg | atgcaggtgc | aggtcgtatg | 540 |
| ggtggcacta | cccagtatac | cgtgaacaac | cagatggtga | acgcgaccct | gatgaacatc | 600 |
| gcggataacc | caaccaacgt | tcagctgccg | ggcatgtaca | caaagaaga | caacccgcgt | 660 |
| gtcccgatta | tcgttaccgg | caacgacttc | tccactctct | atgctccgct | gatccgtgac | 720 |

| | |
|---|---|
| ggccgtatgg aaaaattcta ctgggcaccg actcgcgacg atcgtgtagg cgtgtgtaaa | 780 |
| ggtatcttcc gtaccgacaa cgtcccagac gaggacattg tgaaaatcgt ggacagcttt | 840 |
| ccgggccagt ctattgattt cttttggcgct ctgcgtgcac gtgtatacga cgatgaagtc | 900 |
| cgcaaatggg ttagcgacac gggtgttgag aacatcggca aaaaactggt gaactcccgt | 960 |
| gaaggtccac cggaatttga gcagccgaaa atgacgatcg acaaactgat ggagtacggt | 1020 |
| cacatgctgg tacgcgaaca ggaaaacgtg aaacgtgtgc agctggcgga taaatacctg | 1080 |
| agcgaagcag ctctgggtga tgctaactcc gatgcgatga aaaccggctc tttctatggt | 1140 |
| gcagcgccgt cttcctaa | 1158 |

<210> SEQ ID NO 50
<211> LENGTH: 1395
<212> TYPE: DNA
<213> ORGANISM: Oryza australiensis

<400> SEQUENCE: 50

| | |
|---|---|
| atggctgctg ccttctcctc gacagttgga gcacctgcct ctacaccgac aaacttcctg | 60 |
| ggcaagaagc tgaagaagca agtgacatcc gccgtgaact accacggcaa gagctccaac | 120 |
| ataaaccgct tcaaagtcat ggcgaaggag ctcgatgagg acaagcagac cgatcaggac | 180 |
| aagtggaagg gacttgccta cgacatctcc gatgaccagc aggacattac gaggggcaaa | 240 |
| ggtttggtcg actccctttt ccaagcacca atgggagatg gcacgcacga agcagtcctt | 300 |
| agctcctacg agtacctctc ccagggcttg aagatgttgg acaacactat ggggggcttc | 360 |
| tacatcgcac ctgctttcat ggacaagctc gtcgtccaca tctcgaagaa cttcatggcg | 420 |
| ctcccgaaca taaaggtgcc actgattctc gggatctggg aggcaagggg tcaggggaaa | 480 |
| tccttccagt gtgagctcgt cttctccaag atggggatca cccccatcat gatgagcgcc | 540 |
| ggagaactgg aaagcggaaa tgccggagaa ccagcgaaac tgatccgaca gagataccga | 600 |
| gaggcggctg acatcatcaa gaaggggaag atgtgctgcc tcttcatcaa cgatctggat | 660 |
| gcgggagctg gccgaatggg agggactact caatacaccg tcaacaacca gatggtgaac | 720 |
| gcgacccctga tgaacatcgc ggataatccc accaacgtgc aactccctgg gatgtacaac | 780 |
| aaggaggaca atccgcgagt cccccatcatc gtcacgggca atgatttctc gacactctac | 840 |
| gccccgctta tccgagatgg gaggatggag aagttctact gggcacctac cagagacgat | 900 |
| cgcgtaggtg tctgcaaagg catctttcgc actgacaacg tcccggatga ggacatcgtc | 960 |
| aagatcgtcg acagcttccc tggccaatct atcgactttt tcggcgctct acgagcccgt | 1020 |
| gtttacgatg acgaagtgcg gaaatggggtt tcggatacgg gcgtggagaa cattggcaag | 1080 |
| aaactggtga actctaggga agggccacct gagttcgaac agccgaagat gacgatcgac | 1140 |
| aagctcatgg agtacggcca tatgctcgtg agggagcagg agaacgttaa gcgtgttcaa | 1200 |
| ctggccgaca gtacctaagg cgaggcagct ttgggtgacg ctaactccga cgccatgaaa | 1260 |
| actggttcct tctacgggca aggagcacag caaggcggaa acttacctgt gccggaaggt | 1320 |
| tgcactgacc ccgttgcgaa gaactttgac ccaacggcga gatctgacga tgggagctgc | 1380 |
| ctttatacct tttaa | 1395 |

<210> SEQ ID NO 51
<211> LENGTH: 1281
<212> TYPE: DNA
<213> ORGANISM: Oryza australiensis

<400> SEQUENCE: 51

```
atggctgctg ccttctcctc gacagttgga gcacctgcct ctacaccgac aaacttcctg    60
ggcaagaagc tgaagaagca agtgacatcc gccgtgaact accacggcaa gagctccaac   120
ataaaccgct tcaaagtcat ggcgaaggag ctcgatgagg acaagcagac cgatcaggac   180
aagtggaagg gacttgccta cgacatctcc gatgaccagc aggacattac gaggggcaaa   240
ggtttggtcg actcccttt ccaagcacca atgggagatg gcacgcacga agcagtcctt   300
agctcctacg agtacctctc ccagggcttg aagatgttgg acaacactat gggggcttc   360 tacatcgcac ctgctttcat ggacaagctc gtcgtccaca tctcgaagaa cttcatggcg   420
ctcccgaaca taaggtgcc actgattctc gggatctggg gaggcaaggg tcaggggaaa   480
tccttccagt gtgagctcgt cttctccaag atggggatca accccatcat gatgagcgcc   540
ggagaactgg aaagcggaaa tgccggagaa ccagcgaaac tgatccgaca gagataccga   600
gaggcggctg acatcatcaa gaaggggaag atgtgctgcc tcttcatcaa cgatctggat   660
gcgggagctg gccgaatggg agggactact caatacaccg tcaacaacca gatggtgaac   720
gcgaccctga tgaacatcgc ggataatccc accaacgtgc aactccctgg gatgtacaac   780
aaggaggaca atccgcgagt ccccatcatc gtcacgggca atgatttctc gacactctac   840
gccccgctta tccgagatgg gaggatggag aagttctact gggcacctac cagagacgat   900
cgcgtaggtg tctgcaaagg catctttcgc actgacaacg tcccggatga ggacatcgtc   960
aagatcgtcg acagcttccc tggccaatct atcgactttt tcggcgctct acgagcccgt  1020
gtttacgatg acgaagtgcg gaaatgggtt tcggatacgg gcgtggagaa cattggcaag  1080
aaactggtga actctaggga agggccacct gagttcgaac agccgaagat gacgatcgac  1140
aagctcatgg agtacggcca tatgctcgtg agggagcagg agaacgttaa gcgtgttcaa  1200
ctggccgaca agtacctaag cgaggcagct ttgggtgacg ctaactccga cgccatgaaa  1260
actggttcct tctacgggta a                                            1281
```

<210> SEQ ID NO 52
<211> LENGTH: 1296
<212> TYPE: DNA
<213> ORGANISM: Oryza australiensis

<400> SEQUENCE: 52

```
atggctgctg ccttctcctc gacagttgga gcacctgcct ctacaccgac aaacttcctg    60
ggcaagaagc tgaagaagca agtgacatcc gccgtgaact accacggcaa gagctccaac   120
ataaaccgct tcaaagtcat ggcgaaggag ctcgatgagg acaagcagac cgatcaggac   180
aagtggaagg gacttgccta cgacatctcc gatgaccagc aggacattac gaggggcaaa   240
ggtttggtcg actcccttt ccaagcacca atgggagatg gcacgcacga agcagtcctt   300
agctcctacg agtacctctc ccagggcttg aagatgttgg acaacactat gggggcttc   360 tacatcgcac ctgctttcat ggacaagctc gtcgtccaca tctcgaagaa cttcatggcg   420
ctcccgaaca taaggtgcc actgattctc gggatctggg gaggcaaggg tcaggggaaa   480
tccttccagt gtgagctcgt cttctccaag atggggatca accccatcat gatgagcgcc   540
ggagaactgg aaagcggaaa tgccggagaa ccagcgaaac tgatccgaca gagataccga   600
gaggcggctg acatcatcaa gaaggggaag atgtgctgcc tcttcatcaa cgatctggat   660
gcgggagctg gccgaatggg agggactact caatacaccg tcaacaacca gatggtgaac   720
gcgaccctga tgaacatcgc ggataatccc accaacgtgc aactccctgg gatgtacaac   780
```

| | |
|---|---|
| aaggaggaca atccgcgagt ccccatcatc gtcacgggca atgatttctc gacactctac | 840 |
| gccccgctta tccgagatgg gaggatggag aagttctact gggcacctac cagagacgat | 900 |
| cgcgtaggtg tctgcaaagg catctttcgc actgacaacg tcccggatga ggacatcgtc | 960 |
| aagatcgtcg acagcttccc tggccaatct atcgactttt tcggcgctct acgagcccgt | 1020 |
| gtttacgatg acgaagtgcg gaaatgggtt tcggatacgg gcgtggagaa cattggcaag | 1080 |
| aaactggtga actctaggga agggccacct gagttcgaac agccgaagat gacgatcgac | 1140 |
| aagctcatgg agtacggcca tatgctcgtg agggagcagg agaacgttaa gcgtgttcaa | 1200 |
| ctggccgaca agtacctaag cgaggcagct ttgggtgacg ctaactccga cgccatgaaa | 1260 |
| actggttcct tctacggggc cgcgccgagc tcctga | 1296 |

<210> SEQ ID NO 53
<211> LENGTH: 800
<212> TYPE: DNA
<213> ORGANISM: Oryza meridionalis

<400> SEQUENCE: 53

| | |
|---|---|
| gcctccgatt gatgcttcac caaaaaacaa tatcaacagc agtgcaaaat tagaattttt | 60 |
| gtattttttgt ggtaacgcaa accggccatc aaaggggaaa aacgtacaat gcttatgttg | 120 |
| tatgttaaga gaagtttgtg tggtgccaaa tgacagtcct agcctgacgg ttatcgagaa | 180 |
| agcagaatat gtgcaggtgg cagagcaaaa tatttgtggt agtccaacta gaatacaatt | 240 |
| tgcatgccat gcctcatcca agaagccggg caacgagagg cagcaaaagg cttttctgtg | 300 |
| gtgatgcaaa atgaagaggt tatgtagtag ctgagctgat gaagcaactg gtcgctagct | 360 |
| gccggccggg agacgaatgt gaggcaagga aagaaaagaa aaaacagaga gaaagagttg | 420 |
| atcagaaatg ggtgaattct gtggtgagga aaggtcaagg aactgaagcc aagagatcct | 480 |
| tcctacctac actaatacaa tactcctaac tcgctcacag actccgatcc aggtccaagt | 540 |
| catgctatgc tgtggatcgg ccggccgaga ttgcgccacg tgtgcagaac ccaatcttca | 600 |
| gcgtgtggcc tgtggggat ctggaagctg atccacaggg agggaggagt gtgtgcctct | 660 |
| cacagcttcc aacttccatg cgacgtcca atgctattgt attatttaag gcctaccgca | 720 |
| gctcggcctc tacactttga gcagcagcgg ctggccatca tcagtgatcc tctacaatca | 780 |
| tcgactttca gcaaattaag | 800 |

<210> SEQ ID NO 54
<211> LENGTH: 1401
<212> TYPE: DNA
<213> ORGANISM: Oryza meridionalis

<400> SEQUENCE: 54

| | |
|---|---|
| atggctgctg ccttctcctc caccgttgga gctccggcgt ccactccgac caacttcctg | 60 |
| gggaagaagc tgaagaagca ggtgacatcg gcggtgaact accatggcaa gagctccaac | 120 |
| atcaacaggt tcaaggtgat ggccaaggag ctggacgagg caagcagac cgaccaggac | 180 |
| aggtggaagg gtctcgccta cgacatctcc gatgaccagc aggacatcac caggggaag | 240 |
| ggtttcgtcg actccctgtt ccaggctccc acggtgatg caccacga ggccgtcctc | 300 |
| agctcctacg agtacctcag ccagggtctc agaacgtacg acttcgacaa caccatggga | 360 |
| ggcttctaca tcgcccctgc tttcatggac aagctcgtcg tccacatctc caagaacttc | 420 |
| atgacccctcc ccaacatcaa ggtcccactc atcctgggta tctggggagg caagggtcag | 480 |
| ggaaaatcct tccagtgtga gctcgtcttc gccaagatgg ggatcaaccc catcatgatg | 540 |

```
agcgccggag agctggagag cggcaacgcc ggagagccgg cgaagctgat caggcagcgg     600
taccgtgagg cggcagacat catcaagaag gggaagatgt gctgcctctt catcaacgat     660
ctggatgccg gtgcaggtcg catgggaggc accacccagt acacggtgaa caaccagatg     720
gtgaacgcca ccctgatgaa catcgccgac aacccaacca acgtgcagct cccagggatg     780
tacaacaagg aggacaaccc ccgtgtcccc atcatcgtca ccggcaacga cttctccacg     840
ctgtacgcgc cgctcatccg tgacgggcgt atggagaagt ctactgggc tcccacccgc     900 gacgaccgtg tcggcgtctg caagggtatc ttccgcaccg acaacgtccc cgacgaggac     960
atcgtcaaga tcgtcgacag cttcccaggc caatccatcg atttcttcgg cgctctgcgt    1020
gcccgtgttt acgacgacga ggtgcgcaag tgggtgtcgg acaccggtgt ggagaacatt    1080 ggcaagagc tggtgaactc gagggagggc ccaccggagt tcgagcagcc caagatgacg     1140
atcgaaaagc tcatggagta cggatacatg cttgtgaagg agcaggagaa cgtcaagcgt    1200
gtgcagctgg ctgagcagta cttgagcgag ctgctcttg gtgacgctaa ctccgacgcc     1260
atgaagactg gttccttcta cgggcaagga gcacagcaag caggtaacct gcctgtgccg    1320
gaaggttgca ccgacccgt tgccaagaac ttcgacccaa cggcgaggag cgacgacggc     1380
agctgccttt acacctttta a                                              1401
```

<210> SEQ ID NO 55
<211> LENGTH: 466
<212> TYPE: PRT
<213> ORGANISM: Oryza meridionalis

<400> SEQUENCE: 55

```
Met Ala Ala Ala Phe Ser Ser Thr Val Gly Ala Pro Ala Ser Thr Pro
1               5                   10                  15

Thr Asn Phe Leu Gly Lys Lys Leu Lys Lys Gln Val Thr Ser Ala Val
            20                  25                  30

Asn Tyr His Gly Lys Ser Ser Asn Ile Asn Arg Phe Lys Val Met Ala
        35                  40                  45

Lys Glu Leu Asp Glu Gly Lys Gln Thr Asp Gln Asp Arg Trp Lys Gly
    50                  55                  60

Leu Ala Tyr Asp Ile Ser Asp Asp Gln Gln Asp Ile Thr Arg Gly Lys
65                  70                  75                  80

Gly Phe Val Asp Ser Leu Phe Gln Ala Pro Thr Gly Asp Gly Thr His
                85                  90                  95

Glu Ala Val Leu Ser Ser Tyr Glu Tyr Leu Ser Gln Gly Leu Arg Thr
            100                 105                 110

Tyr Asp Phe Asp Asn Thr Met Gly Gly Phe Tyr Ile Ala Pro Ala Phe
        115                 120                 125

Met Asp Lys Leu Val Val His Ile Ser Lys Asn Phe Met Thr Leu Pro
    130                 135                 140

Asn Ile Lys Val Pro Leu Ile Leu Gly Ile Trp Gly Gly Lys Gly Gln
145                 150                 155                 160

Gly Lys Ser Phe Gln Cys Glu Leu Val Phe Ala Lys Met Gly Ile Asn
                165                 170                 175

Pro Ile Met Met Ser Ala Gly Glu Leu Glu Ser Gly Asn Ala Gly Glu
            180                 185                 190

Pro Ala Lys Leu Ile Arg Gln Arg Tyr Arg Glu Ala Ala Asp Ile Ile
        195                 200                 205

Lys Lys Gly Lys Met Cys Cys Leu Phe Ile Asn Asp Leu Asp Ala Gly
```

```
                210                 215                 220
Ala Gly Arg Met Gly Gly Thr Thr Gln Tyr Thr Val Asn Asn Gln Met
225                 230                 235                 240

Val Asn Ala Thr Leu Met Asn Ile Ala Asp Asn Pro Thr Asn Val Gln
                245                 250                 255

Leu Pro Gly Met Tyr Asn Lys Glu Asp Asn Pro Arg Val Pro Ile Ile
                260                 265                 270

Val Thr Gly Asn Asp Phe Ser Thr Leu Tyr Ala Pro Leu Ile Arg Asp
                275                 280                 285

Gly Arg Met Glu Lys Phe Tyr Trp Ala Pro Thr Arg Asp Asp Arg Val
                290                 295                 300

Gly Val Cys Lys Gly Ile Phe Arg Thr Asp Asn Val Pro Asp Glu Asp
305                 310                 315                 320

Ile Val Lys Ile Val Asp Ser Phe Pro Gly Gln Ser Ile Asp Phe Phe
                325                 330                 335

Gly Ala Leu Arg Ala Arg Val Tyr Asp Asp Glu Val Arg Lys Trp Val
                340                 345                 350

Ser Asp Thr Gly Val Glu Asn Ile Gly Lys Arg Leu Val Asn Ser Arg
                355                 360                 365

Glu Gly Pro Pro Glu Phe Glu Gln Pro Lys Met Thr Ile Glu Lys Leu
                370                 375                 380

Met Glu Tyr Gly Tyr Met Leu Val Lys Glu Gln Glu Asn Val Lys Arg
385                 390                 395                 400

Val Gln Leu Ala Glu Gln Tyr Leu Ser Glu Ala Leu Gly Asp Ala
                405                 410                 415

Asn Ser Asp Ala Met Lys Thr Gly Ser Phe Tyr Gly Gln Gly Ala Gln
                420                 425                 430

Gln Ala Gly Asn Leu Pro Val Pro Glu Gly Cys Thr Asp Pro Val Ala
                435                 440                 445

Lys Asn Phe Asp Pro Thr Ala Arg Ser Asp Asp Gly Ser Cys Leu Tyr
                450                 455                 460

Thr Phe
465

<210> SEQ ID NO 56
<211> LENGTH: 433
<212> TYPE: PRT
<213> ORGANISM: Oryza meridionalis

<400> SEQUENCE: 56

Met Ala Ala Ala Phe Ser Ser Thr Val Gly Ala Pro Ala Ser Thr Pro
1               5                   10                  15

Thr Asn Phe Leu Gly Lys Lys Leu Lys Lys Gln Val Thr Ser Ala Val
                20                  25                  30

Asn Tyr His Gly Lys Ser Ser Asn Ile Asn Arg Phe Lys Val Met Ala
                35                  40                  45

Lys Glu Leu Asp Glu Gly Lys Gln Thr Asp Gln Asp Arg Trp Lys Gly
                50                  55                  60

Leu Ala Tyr Asp Ile Ser Asp Asp Gln Gln Asp Ile Thr Arg Gly Lys
65                  70                  75                  80

Gly Phe Val Asp Ser Leu Phe Gln Ala Pro Thr Gly Asp Gly Thr His
                85                  90                  95

Glu Ala Val Leu Ser Ser Tyr Glu Tyr Leu Ser Gln Gly Leu Arg Thr
                100                 105                 110
```

Tyr Asp Phe Asp Asn Thr Met Gly Gly Phe Tyr Ile Ala Pro Ala Phe
            115                 120                 125

Met Asp Lys Leu Val Val His Ile Ser Lys Asn Phe Met Thr Leu Pro
130                 135                 140

Asn Ile Lys Val Pro Leu Ile Leu Gly Ile Trp Gly Gly Lys Gly Gln
145                 150                 155                 160

Gly Lys Ser Phe Gln Cys Glu Leu Val Phe Ala Lys Met Gly Ile Asn
                165                 170                 175

Pro Ile Met Met Ser Ala Gly Glu Leu Glu Ser Gly Asn Ala Gly Glu
            180                 185                 190

Pro Ala Lys Leu Ile Arg Gln Arg Tyr Arg Glu Ala Ala Asp Ile Ile
            195                 200                 205

Lys Lys Gly Lys Met Cys Cys Leu Phe Ile Asn Asp Leu Asp Ala Gly
            210                 215                 220

Ala Gly Arg Met Gly Gly Thr Thr Gln Tyr Thr Val Asn Asn Gln Met
225                 230                 235                 240

Val Asn Ala Thr Leu Met Asn Ile Ala Asp Asn Pro Thr Asn Val Gln
                245                 250                 255

Leu Pro Gly Met Tyr Asn Lys Glu Asp Asn Pro Arg Val Pro Ile Ile
            260                 265                 270

Val Thr Gly Asn Asp Phe Ser Thr Leu Tyr Ala Pro Leu Ile Arg Asp
            275                 280                 285

Gly Arg Met Glu Lys Phe Tyr Trp Ala Pro Thr Arg Asp Asp Arg Val
            290                 295                 300

Gly Val Cys Lys Gly Ile Phe Arg Thr Asp Asn Val Pro Asp Glu Asp
305                 310                 315                 320

Ile Val Lys Ile Val Asp Ser Phe Pro Gly Gln Ser Ile Asp Phe Phe
                325                 330                 335

Gly Ala Leu Arg Ala Arg Val Tyr Asp Asp Glu Val Arg Lys Trp Val
            340                 345                 350

Ser Asp Thr Gly Val Glu Asn Ile Gly Lys Arg Leu Val Asn Ser Arg
            355                 360                 365

Glu Gly Pro Pro Glu Phe Glu Gln Pro Lys Met Thr Ile Glu Lys Leu
            370                 375                 380

Met Glu Tyr Gly Tyr Met Leu Val Lys Glu Gln Glu Asn Val Lys Arg
385                 390                 395                 400

Val Gln Leu Ala Glu Gln Tyr Leu Ser Glu Ala Leu Gly Asp Ala
                405                 410                 415

Asn Ser Asp Ala Met Lys Thr Gly Ser Phe Tyr Gly Ser Ala Pro Ser
            420                 425                 430

Ser

<210> SEQ ID NO 57
<211> LENGTH: 428
<212> TYPE: PRT
<213> ORGANISM: Deschampsia caespitosa

<400> SEQUENCE: 57

Met Ala Ala Ala Phe Ser Ser Thr Val Gly Ala Pro Ala Ser Thr Pro
1               5                   10                  15

Thr Ser Phe Leu Gly Asn Lys Leu Lys Lys Gln Val Thr Ser Ala Val
                20                  25                  30

Asn Tyr His Gly Lys Ser Phe Lys Ala Asn Arg Phe Thr Val Met Ala
            35                  40                  45

```
Lys Asp Ile Asp Glu Gly Lys Gln Thr Asp Gly Asp Lys Trp Lys Gly
 50                  55                  60

Leu Ala Tyr Asp Ile Ser Asp Gln Gln Asp Ile Thr Arg Gly Lys
 65                  70                  75                  80

Gly Ile Val Asp Ser Leu Phe Gln Ala Pro Met Gly Asp Gly Thr His
                 85                  90                  95

Glu Ala Val Leu Ser Ser Tyr Glu Tyr Val Ser Gln Gly Leu Lys Lys
            100                 105                 110

Tyr Asp Phe Asp Asn Thr Met Gly Gly Phe Tyr Ile Ala Pro Ala Phe
        115                 120                 125

Met Asp Lys Leu Val Val His Leu Ser Lys Asn Phe Met Thr Leu Pro
130                 135                 140

Asn Ile Lys Ile Pro Leu Ile Leu Gly Ile Trp Gly Gly Lys Gly Gln
145                 150                 155                 160

Gly Lys Ser Phe Gln Cys Glu Leu Val Phe Ala Lys Met Gly Ile Asn
                165                 170                 175

Pro Ile Met Met Ser Ala Gly Glu Leu Glu Ser Gly Asn Ala Gly Glu
            180                 185                 190

Pro Ala Lys Leu Ile Arg Gln Arg Tyr Arg Glu Ala Ala Asp Met Ile
        195                 200                 205

Lys Lys Gly Lys Met Cys Cys Leu Phe Ile Asn Asp Leu Asp Ala Gly
210                 215                 220

Ala Gly Arg Met Gly Gly Thr Thr Gln Tyr Thr Val Asn Asn Gln Met
225                 230                 235                 240

Val Asn Ala Thr Leu Met Asn Ile Ala Asp Ala Pro Thr Asn Val Gln
                245                 250                 255

Leu Pro Gly Met Tyr Asn Lys Glu Glu Asn Pro Arg Val Pro Ile Ile
            260                 265                 270

Val Thr Gly Asn Asp Phe Ser Thr Leu Tyr Ala Pro Leu Ile Arg Asp
        275                 280                 285

Gly Arg Met Glu Lys Phe Tyr Trp Ala Pro Thr Arg Glu Asp Arg Ile
290                 295                 300

Gly Val Cys Lys Gly Ile Phe Gln Thr Asp Asn Val Ser Asp Glu Ser
305                 310                 315                 320

Val Val Lys Ile Val Asp Thr Phe Pro Gly Gln Ser Ile Asp Phe Phe
                325                 330                 335

Gly Ala Leu Arg Ala Arg Val Tyr Asp Val Glu Val Arg Lys Trp Val
            340                 345                 350

Ser Ser Thr Gly Ile Glu Asn Ile Gly Lys Arg Leu Val Asn Ser Arg
        355                 360                 365

Asp Gly Pro Val Thr Phe Glu Gln Pro Lys Met Thr Val Glu Lys Leu
370                 375                 380

Leu Glu Tyr Gly His Met Leu Val Gln Glu Gln Asp Asn Val Lys Arg
385                 390                 395                 400

Val Gln Leu Ala Asp Thr Tyr Met Ser Gln Ala Ala Leu Gly Asp Ala
                405                 410                 415

Asn Lys Asp Ala Met Lys Thr Gly Ser Phe Tyr Gly
            420                 425

<210> SEQ ID NO 58
<211> LENGTH: 421
<212> TYPE: PRT
<213> ORGANISM: Gossypium hirsutum

<400> SEQUENCE: 58
```

```
Met Ala Ala Glu Lys Glu Ile Asp Glu Thr Gln Thr Lys Asp
1               5                   10                  15

Arg Trp Lys Gly Leu Ala Tyr Asp Ile Ser Asp Gln Gln Asp Ile
            20                  25                  30

Thr Arg Gly Lys Gly Met Val Asp Ser Leu Phe Gln Ala Pro Met Asn
        35                  40                  45

Asp Gly Thr His Tyr Ala Val Met Ser Ser Tyr Glu Tyr Ile Ser Gln
    50                  55                  60

Gly Leu Lys Thr Tyr Asn Leu Asp Asn Asn Met Asp Gly Phe Tyr Ile
65                  70                  75                  80

Ala Pro Ala Phe Met Asp Lys Leu Val Val His Ile Ser Lys Asn Phe
                85                  90                  95

Met Ser Leu Pro Asn Ile Lys Val Pro Leu Ile Leu Gly Ile Trp Gly
                100                 105                 110

Gly Lys Gly Gln Gly Lys Ser Phe Gln Cys Glu Leu Val Phe Ala Lys
        115                 120                 125

Met Gly Ile Asn Pro Ile Met Met Ser Ala Gly Glu Leu Glu Ser Gly
130                 135                 140

Asn Ala Gly Glu Pro Ala Lys Leu Ile Arg Gln Arg Tyr Arg Glu Ala
145                 150                 155                 160

Ala Asp Ile Ile Lys Lys Gly Lys Met Cys Ala Leu Phe Ile Asn Asp
                165                 170                 175

Leu Asp Ala Gly Ala Gly Arg Met Gly Gly Thr Thr Gln Tyr Thr Val
                180                 185                 190

Asn Asn Gln Met Val Asn Ala Thr Leu Met Asn Ile Ala Asp Asn Pro
                195                 200                 205

Thr Asn Val Gln Leu Pro Gly Met Tyr Asn Lys Glu Glu Asn Pro Arg
210                 215                 220

Val Pro Ile Ile Val Thr Gly Asn Asp Phe Ser Thr Leu Tyr Ala Pro
225                 230                 235                 240

Leu Ile Arg Asp Gly Arg Met Glu Lys Phe Tyr Trp Ala Pro Thr Arg
                245                 250                 255

Asp Asp Arg Ile Gly Val Cys Lys Gly Ile Phe Arg Thr Asp Gly Val
                260                 265                 270

Arg Asp Glu Asp Ile Val Lys Leu Val Asp Thr Phe Pro Gly Gln Ser
        275                 280                 285

Ile Asp Phe Phe Gly Ala Leu Arg Ala Arg Val Tyr Asp Asp Glu Val
290                 295                 300

Arg Lys Trp Ile Ser Glu Val Gly Val Ala Ser Val Gly Lys Lys Leu
305                 310                 315                 320

Val Asn Ser Arg Glu Gly Pro Pro Thr Phe Glu Gln Pro Lys Met Thr
            325                 330                 335

Ile Glu Lys Leu Leu Glu Tyr Gly Asn Met Leu Val Ala Glu Gln Glu
                340                 345                 350

Asn Val Lys Arg Val Gln Leu Ala Asp Lys Tyr Leu Ser Glu Ala Ala
            355                 360                 365

Leu Gly Glu Ala Asn Glu Asp Ser Ile Asn Arg Gly Thr Phe Tyr Gly
    370                 375                 380

Lys Ala Ala Gln Gln Val Gly Val Pro Val Pro Glu Gly Cys Thr Asp
385                 390                 395                 400

Pro Asn Ala Asp Asn Phe Asp Pro Thr Ala Arg Ser Asp Asp Gly Thr
            405                 410                 415
```

Cys Thr Tyr Gln Phe
            420

<210> SEQ ID NO 59
<211> LENGTH: 435
<212> TYPE: PRT
<213> ORGANISM: Larrea tridentata

<400> SEQUENCE: 59

```
Met Ala Ala Tyr Ser Thr Val Gly Ala Val Asn Arg Ala Pro Leu
1               5                   10                  15

Ser Leu Asn Gly Ser Gly Ala Arg Ala Ser Leu Val Pro Ser Thr Ala
            20                  25                  30

Phe Phe Gly Ser Ser Leu Lys Lys Ser Ala Ala Lys Phe Pro Lys Ala
            35                  40                  45

Ser Ser Gly Asn Phe Lys Ile Val Ala Gln Glu Ile Ser Glu Asp Gln
        50                  55                  60

Gln Thr Asp Lys Asp Lys Trp Lys Gly Leu Ala Tyr Asp Ile Ser Asp
65                  70                  75                  80

Asp Gln Gln Asp Ile Thr Arg Gly Lys Gly Met Val Asp Thr Leu Phe
                85                  90                  95

Gln Ala Pro Met Gln Ser Gly Thr His Tyr Ala Val Met Ser Ser Tyr
            100                 105                 110

Asp Tyr Ile Ser Gln Gly Leu Arg Gln Tyr Asn Leu Asp Asn Asn Met
        115                 120                 125

Asp Gly Phe Tyr Ile Ala Pro Ala Phe Met Asp Lys Leu Val Val His
    130                 135                 140

Ile Thr Lys Asn Phe Leu Ser Leu Pro Asn Ile Lys Ile Pro Leu Ile
145                 150                 155                 160

Leu Gly Ile Trp Gly Gly Lys Gly Gln Gly Lys Ser Phe Gln Cys Glu
                165                 170                 175

Leu Val Phe Ala Lys Met Gly Ile Asn Pro Ile Met Met Ser Ala Gly
            180                 185                 190

Glu Leu Glu Ser Gly Asn Ala Gly Glu Pro Ala Lys Leu Ile Arg Gln
        195                 200                 205

Arg Tyr Arg Glu Ala Ala Asp Ile Ile Lys Lys Gly Lys Met Cys Cys
    210                 215                 220

Leu Phe Ile Asn Asp Leu Asp Ala Gly Ala Gly Arg Met Gly Gly Thr
225                 230                 235                 240

Thr Gln Tyr Thr Val Asn Asn Gln Met Val Asn Ala Thr Leu Met Asn
                245                 250                 255

Ile Ala Asp Asn Pro Thr Asn Val Gln Leu Pro Gly Met Tyr Asn Lys
            260                 265                 270

Glu Glu Asn Pro Arg Val Pro Ile Ile Val Thr Gly Asn Asp Phe Ser
        275                 280                 285

Thr Leu Tyr Ala Pro Leu Ile Arg Asp Gly Arg Met Glu Lys Phe Tyr
    290                 295                 300

Trp Ala Pro Thr Arg Glu Asp Arg Ile Gly Val Cys Lys Gly Ile Phe
305                 310                 315                 320

Arg Thr Asp Asn Val Pro Glu Glu Asp Ile Val Lys Val Val Asp Gln
                325                 330                 335

Phe Pro Gly Gln Ser Ile Asp Phe Phe Gly Ala Leu Arg Ala Arg Val
            340                 345                 350

Tyr Asp Asp Glu Val Arg Lys Trp Val Ser Glu Val Gly Val Asp Thr
        355                 360                 365
```

Ile Gly Lys Lys Leu Val Asn Ser Lys Glu Gly Pro Pro Thr Phe Glu
                370                 375                 380

Gln Pro Lys Met Thr Ile Asp Lys Leu Leu Gln Tyr Gly Asn Met Leu
385                 390                 395                 400

Val Glu Glu Gln Glu Asn Val Lys Arg Val Gln Leu Ala Asp Lys Tyr
                405                 410                 415

Met Ser Glu Ala Ala Leu Gly Asp Ala Asn Gln Asp Ala Ile Lys Arg
                420                 425                 430

Gly Thr Phe
        435

<210> SEQ ID NO 60
<211> LENGTH: 472
<212> TYPE: PRT
<213> ORGANISM: Spiacia oleracia

<400> SEQUENCE: 60

Met Ala Thr Ala Val Ser Thr Val Gly Ala Ala Thr Arg Ala Pro Leu
1               5                   10                  15

Asn Leu Asn Gly Ser Ser Ala Gly Ala Ser Val Pro Thr Ser Gly Phe
                20                  25                  30

Leu Gly Ser Ser Leu Lys Lys His Thr Asn Val Arg Phe Pro Ser Ser
            35                  40                  45

Ser Arg Thr Thr Ser Met Thr Val Lys Ala Ala Glu Asn Glu Glu Lys
50                  55                  60

Asn Thr Asp Lys Trp Ala His Leu Ala Lys Asp Phe Ser Asp Asp Gln
65                  70                  75                  80

Leu Asp Ile Arg Arg Gly Lys Gly Met Val Asp Ser Leu Phe Gln Ala
                85                  90                  95

Pro Ala Asp Ala Gly Thr His Val Pro Ile Gln Ser Ser Phe Glu Tyr
            100                 105                 110

Glu Ser Gln Gly Leu Arg Lys Tyr Asp Ile Asp Asn Met Leu Gly Asp
            115                 120                 125

Phe Tyr Ile Ala Pro Ala Phe Met Asp Lys Leu Val Val His Ile Thr
130                 135                 140

Lys Asn Phe Leu Asn Leu Pro Asn Ile Lys Ile Pro Leu Ile Leu Gly
145                 150                 155                 160

Val Trp Gly Gly Lys Gly Gln Gly Lys Ser Phe Gln Cys Glu Leu Val
                165                 170                 175

Phe Ala Lys Leu Gly Ile Asn Pro Ile Met Met Ser Ala Gly Glu Leu
            180                 185                 190

Glu Ser Gly Asn Ala Gly Glu Pro Ala Lys Leu Ile Arg Gln Arg Tyr
            195                 200                 205

Arg Glu Ala Ala Asp Leu Ile Ala Lys Gly Lys Met Cys Ala Leu Phe
210                 215                 220

Ile Asn Asp Leu Glu Pro Gly Ala Gly Arg Met Gly Gly Thr Thr Gln
225                 230                 235                 240

Tyr Thr Val Asn Asn Gln Met Val Asn Ala Thr Leu Met Asn Ile Ala
                245                 250                 255

Asp Asn Pro Thr Asn Val Gln Leu Pro Gly Met Tyr Asn Lys Gln Asp
            260                 265                 270

Asn Ala Arg Val Pro Ile Ile Val Thr Gly Asn Asp Phe Ser Thr Leu
            275                 280                 285

Tyr Ala Pro Leu Ile Arg Asp Gly Arg Met Glu Lys Phe Tyr Trp Ala

-continued

```
            290                 295                 300
Pro Thr Arg Glu Asp Arg Ile Gly Val Cys Thr Gly Ile Phe Lys Thr
305                 310                 315                 320

Asp Lys Val Pro Ala Glu His Val Val Lys Leu Val Asp Ala Phe Pro
                325                 330                 335

Gly Gln Ser Ile Asp Phe Phe Gly Ala Leu Arg Ala Arg Val Tyr His
            340                 345                 350

Asp Glu Val Arg Lys Trp Val Asn Ser Val Gly Val Asp Asn Val Gly
            355                 360                 365

Lys Lys Leu Val Asn Ser Lys Asp Gly Pro Pro Val Phe Glu Gln Pro
        370                 375                 380

Glu Met Thr Leu Gln Lys Leu Met Glu Tyr Gly Asn Met Leu Val Gln
385                 390                 395                 400

Glu Gln Glu Asn Val Lys Arg Val Gln Leu Ala Asp Gln Tyr Met Ser
                405                 410                 415

Ser Ala Ala Leu Gly Asp Ala Asn Lys Asp Ala Ile Asp Arg Gly Thr
            420                 425                 430

Phe Phe Gly Lys Ala Ala Gln Gln Val Ser Leu Pro Val Ala Gln Gly
        435                 440                 445

Cys Thr Asp Pro Glu Ala Lys Asn Tyr Asp Pro Thr Ala Arg Ser Asp
        450                 455                 460

Asp Gly Ser Cys Thr Tyr Asn Leu
465                 470
```

THERMOSTABLE RUBISCO ACTIVASE COMPLEXES

TECHNICAL FIELD

The present invention relates to thermostable complexes comprising Rubisco activase. In particular the invention relates to thermostable complexes comprising Rubisco activase and Ribulose-1,5-bis-phosphate carboxylase/oxygenase and their uses for heat-tolerant plants.

BACKGROUND

During photosynthesis plants generate biomass by converting inorganic carbon in the form of $CO_2$ to carbohydrates using light energy. Accordingly, increasing the efficiency of photosynthesis is a target for improving crop productivity via conventional breeding practices and transgenic approaches.

Ribulose-1,5-bis-phosphate carboxylase/oxygenase (Rubisco) catalyzes the incorporation (fixation) of $CO_2$ into ribulose-1,5-bisphosphate to yield two molecules of 3-phosphoglycerate. Rubisco can be present in either an active or inactive state and the conversion of the inactive state to the active state by rubisco activase is required for $CO_2$ fixation. This process entails the carbamylation of a specific lysine residue of Rubisco. When ribulose-1,5-bisphosphate from the stroma attaches to Rubisco it causes conformational changes, allowing the enzyme to catalyse the reaction of $CO_2$ with the newly sequestered sugar bisphosphate and starting a catalytic cycle. However, in the absence of Rubisco activase (RCA), the tight binding of ribulose-1,5-bisphosphate to the uncarbamylated Rubisco inactivates Rubisco so the rate of $CO_2$ fixation declines. RCA uncouples ribulose-1,5-bisphosphate from decarbamylated active sites and thus promotes the access of $CO_2$ for the carbamylation (activation) of the enzyme. That is, the activation of Rubisco enhances its catalytic capacity and thus facilitates photosynthesis.

RCA is generally present in two forms, termed alpha (long form) and beta (short form), with the latter being a truncated form of the alpha protein.

Photosynthesis is reduced when the temperature exceeds the optimum range for a particular plant and the reduction in photosynthesis at elevated temperatures is linked to Rubisco deactivation due to the inhibition of RCA.

The present invention is based on the finding that complexes comprising *Oryza australiensis* RCA and Rubisco are active at elevated temperatures.

DISCLOSURE OF INVENTION

The present inventors have found that the Rubisco activase (RCA) from *Oryza australiensis* confers thermostability to a complex of RCA with endogenous Ribulose-1,5-bis-phosphate carboxylase/oxygenase (Rubisco). It has also been found that the isolated RCA from *Oryza australiensis* confers thermostability to a complex formed with Rubisco from other plants. Accordingly, the isolated RCA from *Oryza australiensis* can be used to enhance heat tolerance in a plant.

In a first aspect there is provided a complex comprising RCA from *Oryza australiensis*, or functional variants thereof, and a Rubisco that is not from *O. australiensis* wherein the RCA confers thermostability to the complex.

The RCA may comprise at least one of SEQ ID NOs: 2 to 37, 39 or 40.

In a second aspect, there is provided a RCA from *Oryza australiensis*, and functional variants thereof, capable of forming a complex with a Rubisco from a plant other than *O. australiensis* and conferring thermostability to the complex.

In some embodiments the RCA comprises at least one of SEQ ID NOs: 2 to 37, 39 or 40. In some embodiments the RCA has at least 90%, at least 95%, at least 99% or 100% sequence identity to SEQ ID NO: 39 or 40.

In a third aspect there is provided an isolated nucleic acid encoding the thermostable RCA of the second aspect of the present invention.

In some embodiments the isolated nucleic acid encoding thermostable RCA comprises at least one of SEQ ID NOs: 41, 42, 50, 51 and 52. In some embodiments the isolated nucleic acid has at least 90%, at least 95%, at least 99% or 100% sequence identity to SEQ ID NOs: 41, 42, 50, 51 and 52.

In an embodiment the isolated nucleic acid comprises SEQ ID NO: 51.

In a fourth aspect, there is provided a chimeric gene or vector comprising the nucleic acid of the third aspect of the present invention.

The nucleic acid is operably linked to a promoter, typically a plant expressible promoter. The promoter may be a heat-inducible promoter, green-tissue promoter or a chemical-inducible promoter.

In a fifth aspect there is provided a host cell comprising the complex of the first aspect of the present invention, the RCA of the second aspect of the present invention, the nucleic acid of the third aspect of the present invention, or the vector of the fourth aspect of the present invention.

In an embodiment the host cell is a plant cell. In an embodiment the plant cell is a rice plant cell.

In a sixth aspect, there is provided a thermostable complex of the first aspect of the present invention in a plant species other than *O. australiensis* to enhance heat tolerance in the plant.

In one embodiment, the plant species is of the genus *Oryza*. In some embodiments the plant or plant cell is not *O. australiensis*.

In some embodiments the plants are selected from barley, maize, tomato, potato, rice, soybean, cotton, sunflower, alfalfa, lettuce, canola (oilseed rape), sorghum, and wheat.

In an embodiment the plant is rice. In another embodiment, the plant is wheat.

In a seventh aspect there is provided a method of enhancing heat tolerance in a plant by expressing the RCA of the second aspect of the present invention in the plant.

The method may further comprise providing the plant with a nucleic acid of the third aspect of the present invention or a chimeric gene or vector of the fourth aspect of the present invention.

In one embodiment the plant is capable of fixing carbon dioxide in heat stress conditions.

In one embodiment the RCA is expressed in the one or more plastids of the plant.

In another embodiment the expression of the RCA results in an increase in the rate of photosynthesis in the plant under heat stress conditions.

In an eighth aspect there is provided use of a complex comprising a Rubisco activase (RCA) from *Oryza australiensis* and a Rubisco from a plant other than *O. australiensis* to confer thermostability to the complex in a plant by the RCA.

Throughout this specification, unless the context requires otherwise, the word 'comprise', or variations such as 'comprises' or 'comprising', will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this specification.

Some *Oryza* species are identified herein using the postscript cy, Cy, or CY which refers to Cape York, Australia which is the origin of the accession. Similarly other *Oryza* species are identified with using the post script; kr, or KR which refers to Keep River, Australia, the origin of the accession.

In order that the present invention may be more clearly understood, embodiments will be described with reference to the following drawings and examples.

BRIEF DESCRIPTION OF THE DRAWINGS

FIG. 7(A) rcaIOs-2Pb containing RCA long isoform from *Oryza sativa* SEQ ID NO: 46; FIG. 7(B) rcaIOau-2Pb containing RCA long isoform from *Oryza australiensis* SEQ ID NO: 47; FIG. 7(C) rcaIIOs-3Pb containing RCA short isoform from *Oryza sativa* SEQ ID NO: 48; FIG. 7(D) rcaIIOau-3Pb containing RCA short isoform from *Oryza australiensis* SEQ ID NO: 49; FIG. 7(E) rcaIIOau-2Pb containing RCA long form of Rubisco activase nucleic acid from *O. australiensis* (adapted to rice codon usage) SEQ ID NO: 50; FIG. 7(F) rcaIIOau-3Pb containing RCA short form of Rubisco activase nucleic acid from *O. australiensis* with a 5AA truncation at the end of the gene SEQ ID NO: 51; FIG. 7(G) rcaIIOau-3Pb containing RCA short form of Rubisco activase nucleic acid from *O. australiensis* (adapted to rice codon usage) SEQ ID NO: 52.

*australiensis*). The data show a significant correlation between NAR and RGR ($r^2$=0.76; *O. sativa;* 0.95 *O. australiensis*), indicating assimilation (vis-à-vis leaf morphology) to be the driving variable for growth of these young rice seedlings. Data points are shown with standard error of the mean.

Figure 27:
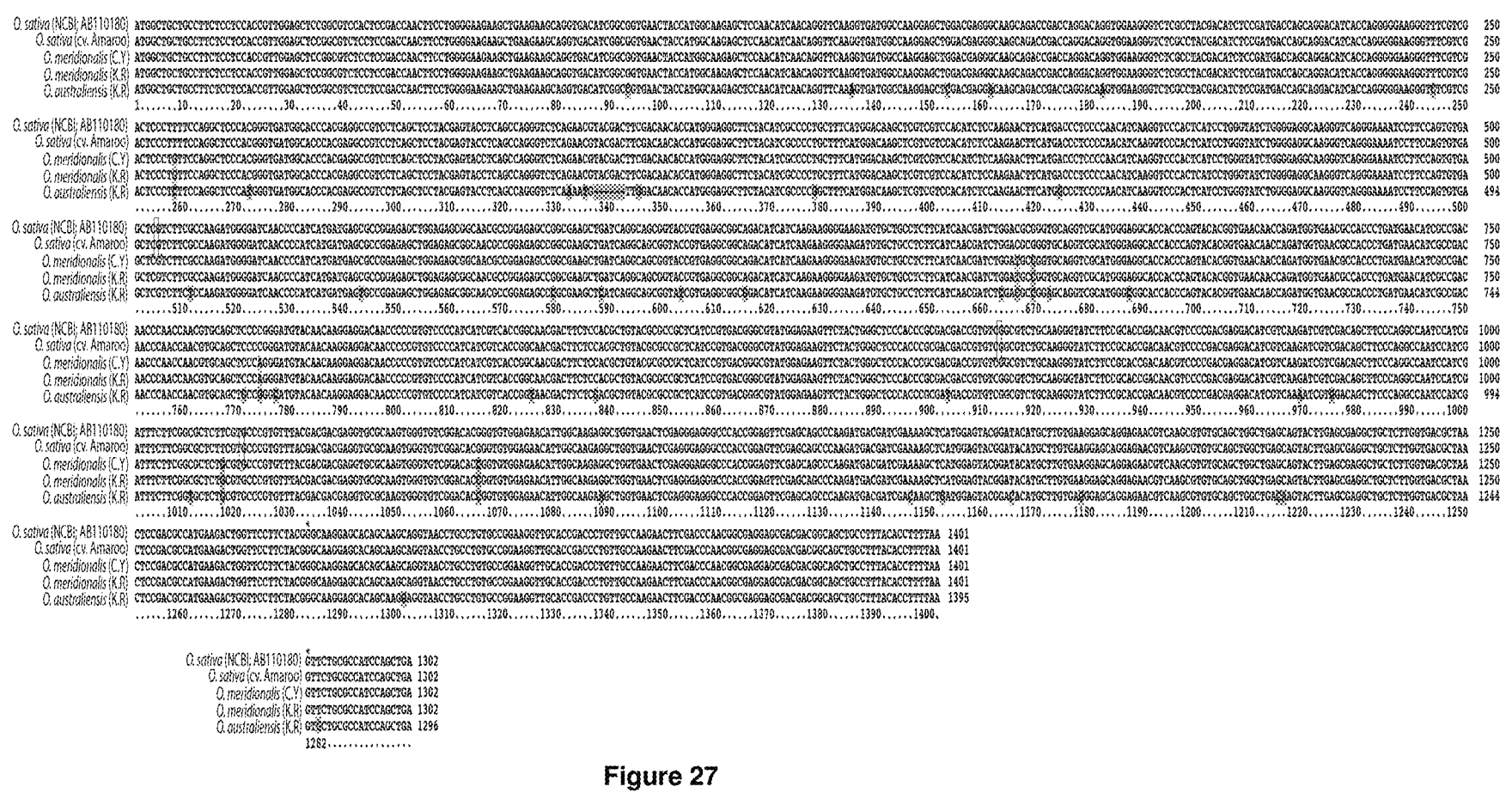

FIG. 27. DNA sequence alignment of Rubisco activase for *O. sativa* ssp. *japonica* cv. Nipponbare (NCBI accession number; AB 110180, SEQ ID NO: 44) with *O. sativa* cv. Amaroo (SEQ ID NO: 44), *O. meridionalis* cy (SEQ ID NO: 54), *O. meridionalis* kr (SEQ ID NO: 54) and *O. australiensis* (SEQ ID NO: 42). Shaded residues represent nucleotide differences. Positions 258, 666 and 774 are differences between *O. sativa* (SEQ ID NO: 44, and *O. meridionalis* (SEQ ID NO: 54). Sequence differences between *O. sativa* (SEQ ID NO: 44, and both *O. meridionalis* (SEQ ID NO: 54) and *O. australiensis* (SEQ ID NO: 42) are also seen at positions 669, 1017 and 1065. Remaining shaded residues in the *O. australiensis* sequence (SEQ ID NO: 42) represent differences between *O. sativa* (SEQ ID NO: 44) and *O. australiensis* (SEQ ID NO: 54).

FIG. 28. Amino acid alignment between the short form (NCBI accession number; BAA97584.1, SEQ ID NO: 38) and long form (NCBI accession number; BAC78572.1, SEQ ID NO: 43) of Rubisco activase from *O. sativa* ssp. *japonica* cv. Nipponbare and the long form of *O. sativa* cv. Amaroo (SEQ ID NO: 43), *O. meridionalis* cy (SEQ ID NO: 55), *O. meridionalis* kr (SEQ ID NO: 55) and *O. australiensis* (SEQ ID NO: 39). Note that the only difference between the two forms is the extra 40 residues at the carboxyl terminal of the long form of activase. Shading shows residues that differ between the protein sequences.

Figure 29:
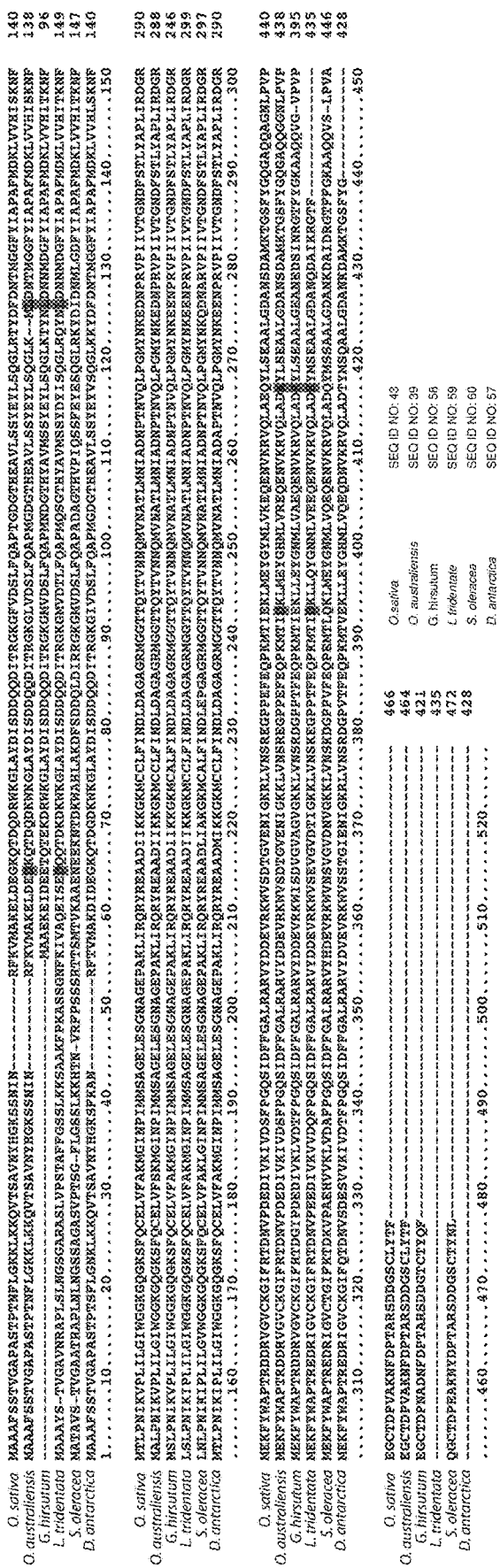

FIG. 29. Amino acid alignment of *O. sativa* cv. Amaroo (SEQ ID NO: 43) and *O. australiensis* (SEQ ID NO: 39) with the warm-adapted species *Gossypium hirsutum* (cotton, SEQ ID NO: 58) and *Larrea tridentata* (creosote bush, SEQ ID NO: 59) and the cold-adapted species *Spinacia oleracea* (spinach, SEQ ID NO: 60) and *Deschampsia antarctica* (Antarctic hairgrass, SEQ ID NO: 57). Shading shows residues that *O. australiensis* has in common with the warm-adapted species that are not present in *O. sativa* or the two cold-adapted species.

Figure 24:
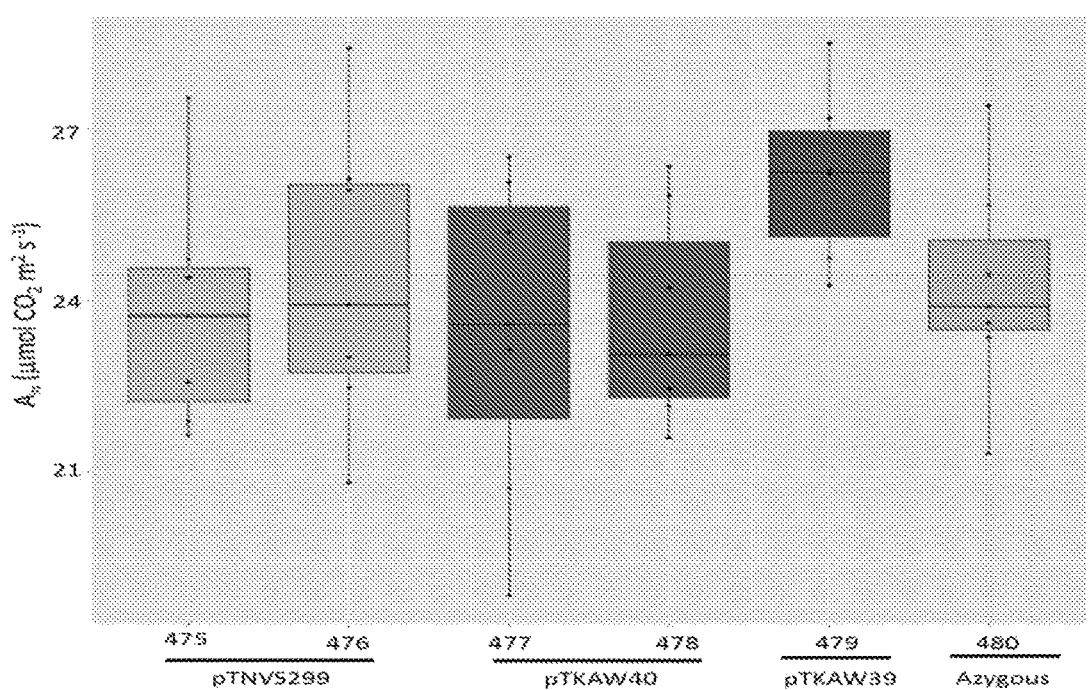
FIG. 24. Shows the net photosynthetic rates (A$_n$) (panel A), the maximum carboxylation rates of rubisco (V$_{cmax}$) (panel B) and the induction kinetics for rubisco after dark-light transition (A$_n$/min) (panel C) of corresponding transgenic and azygous rice lines (rcaIIOa). Boxplots with means and standard deviations are shown for all parameters (n≥6). Asterisks indicate significant difference between homozygous rcaIIOa single copy line and its corresponding null (p≤0.05).
Figure 24:
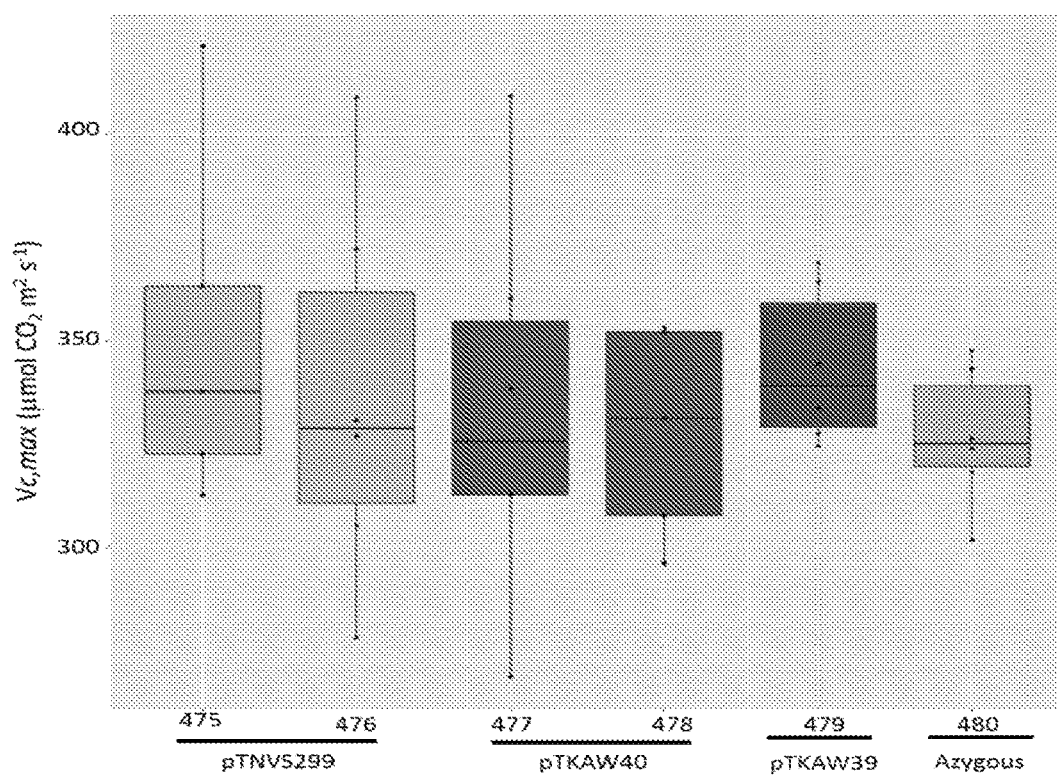
Figure 24:
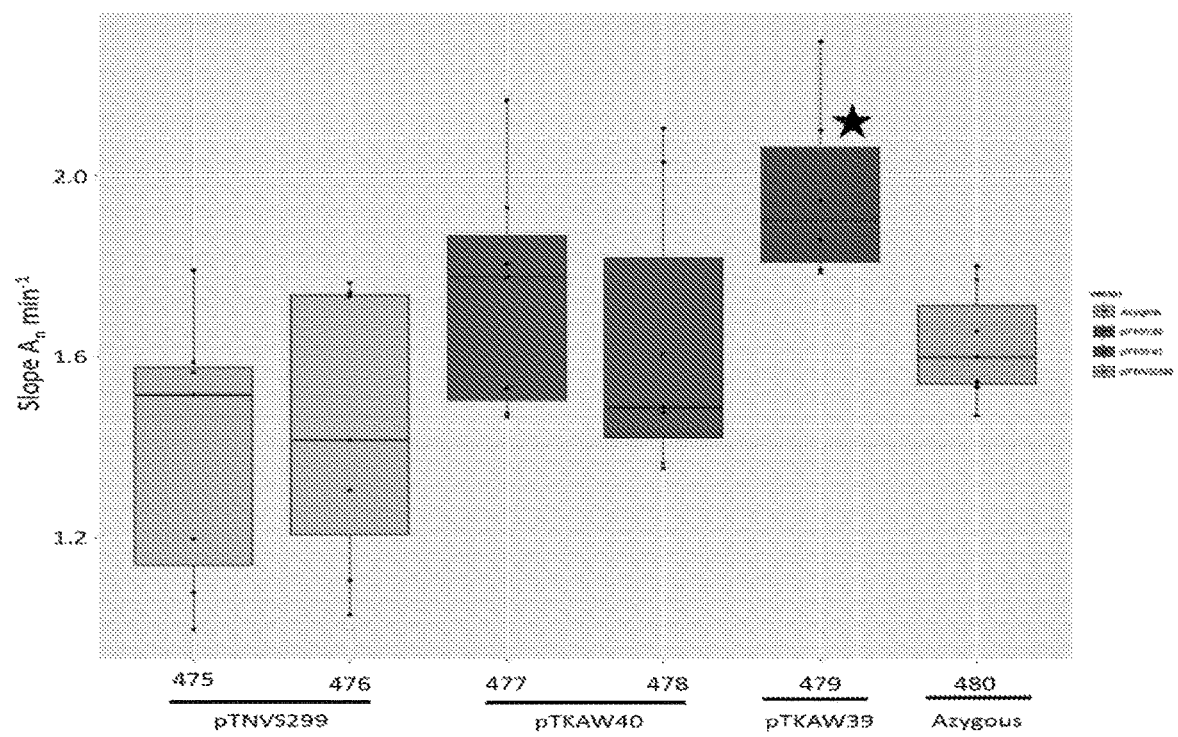
Figure 30:
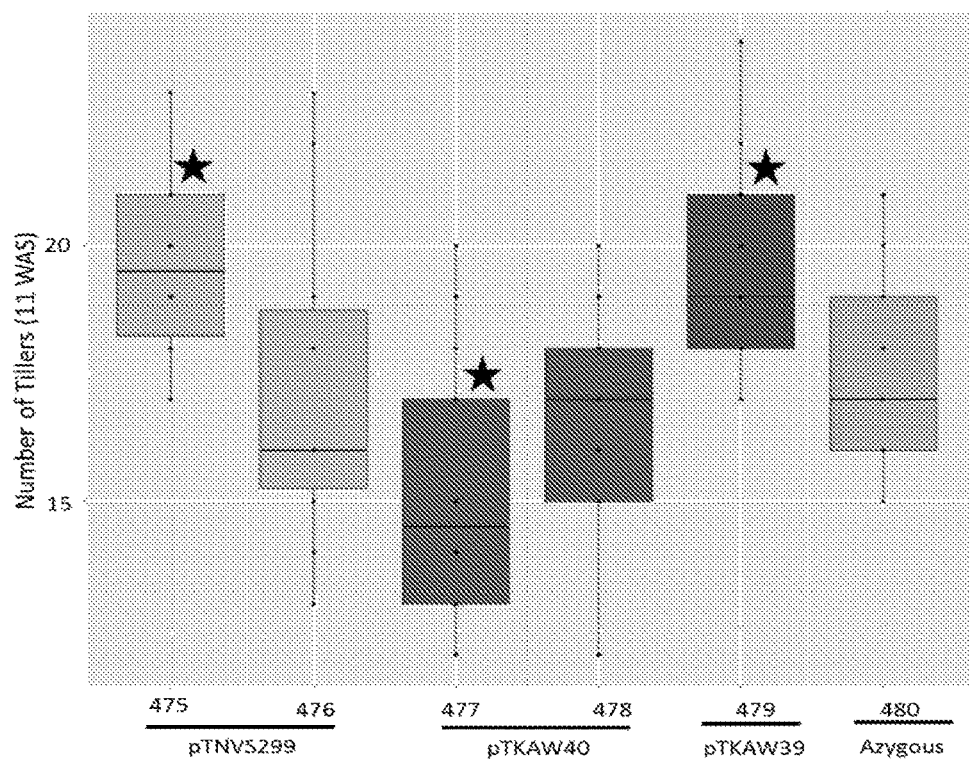

FIG. 30. Tiller numbers measured for each genotype across all 14 blocks after seven weeks of treatment at 45° C. daily. Boxplots are given, as described in FIG. 24.

Figure 31:
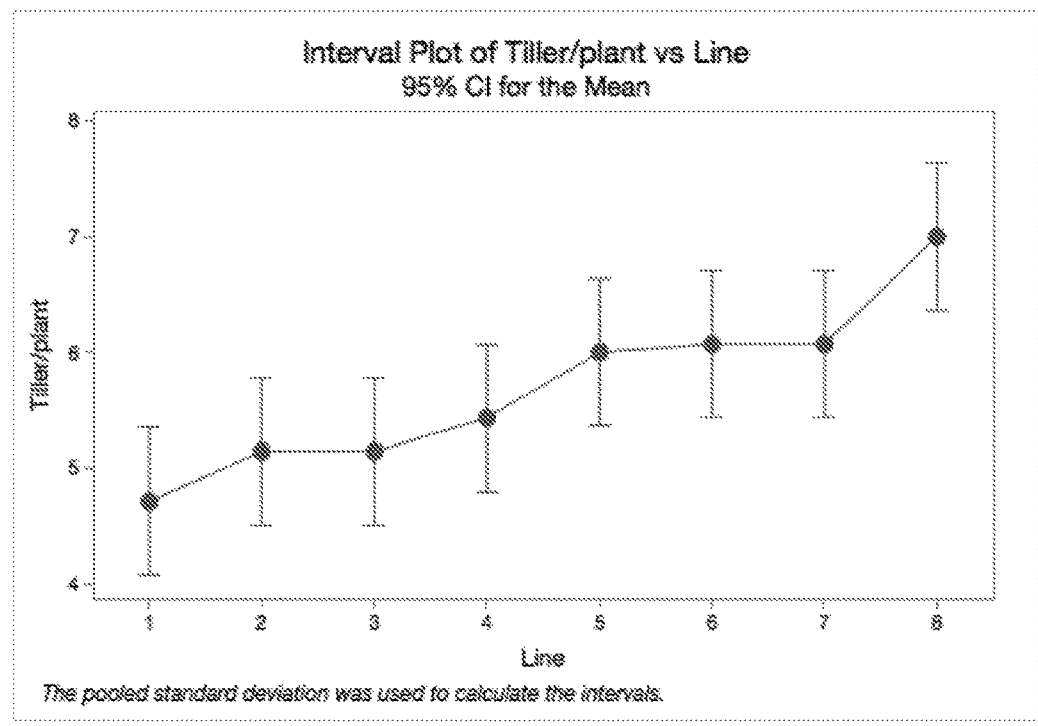

FIG. 31. Results of tillers per plant for eight lines counted in six-week-old plants that had been exposed to one week at 45° C. day temperatures as described in FIG. 23. Lines 1-8 are listed in the order, 474, 472, 478, 476, 473, 475, 480 (control) and 479, respectively.

MODE(S) FOR CARRYING OUT THE INVENTION

The present invention relates to RCA (Rubisco activase) and functionally equivalent polypeptides that confer thermostability to a complex comprising RCA (or a functionally equivalent polypeptide) and Rubisco.

Rubisco Activase (RCA) Polypeptides and Nucleic Acids

In some embodiments, the complexes comprise *O. australiensis* RCA or an RCA comprising at least one of SEQ ID NOs: 2-37, 39, 40 and 50 to 52 in Table 1, Table 2 and Table 6.

TABLE 1

Sequence identification

| SEQ ID NO | Sequence | Relative position* | change in Oa occurs at the following corresponding position in the Os seq | High heat stress[a] | High heat stress[b] |
|---|---|---|---|---|---|
| 1 | See Table 3 | NA | | | |
| 2 | ELDEX$_1$KQTD | E$^{50}$DEX$_1$KQTD | 54 | + | + |
| 3 | ELDEDKQTD | E$^{50}$LDEDKQTD | 54 | + | + |
| 4 | TDQDKWKGL | T$^{57}$DQDKWKGL | 61 | + | |
| 5 | EX$_1$KQTDQDKW | E$^{53}$X$_1$KQTDQDKW | 54, 61 | + | |
| 6 | EDKQTDQDKW | E$^{53}$DKQTDQDKW | 54, 61 | + | |
| 7 | RGKGX$_2$VDSL | R$^{78}$GKGX$_2$VDSL | 82 | + | |
| 8 | RGKGLVDSL | R$^{78}$GKGLVDSL | 82 | + | |
| 9 | FQAPX$_3$GDGT | F$^{87}$QAPX$_3$GDGT | 91 | + | |
| 10 | FQAPMGDGT | F$^{87}$QAPMGDGT | 91 | + | |
| 11 | GX$_2$VDSLFQAPX$_3$ | G$^{81}$X$_2$VDSLFQAPX$_3$ | 82, 91 | + | |
| 12 | GLVDSLFQAPM | G$^{81}$LVDSLFQAPM | 82, 91 | + | |
| 13 | EYLSQGLK | E$^{104}$YLSQGLK | 111 | + | |
| 14 | YLSQGLKX$_1$ | Y$^{105}$LSQGLKX$_1$ | 111, 112 | + | |
| 15 | YLSQGLKM | Y$^{105}$LSQGLKM | 111, 112 | + | |

TABLE 1-continued

Sequence identification

| SEQ ID NO | Sequence | Relative position* | change in Oa occurs at the following corresponding position in the Os seq | High heat stress[a] | High heat stress[b] |
|---|---|---|---|---|---|
| 16 | LSQGLKX$_1$X$_2$ | L$^{106}$SQGLKX$_1$X$_2$ | 111-113 | + | |
| 17 | LSQGLKML | L$^{106}$SQGLKML | 111-113 | + | |
| 18 | KX$_1$X$_2$DNTMGGFY | K$^{111}$X$_1$X$_2$DNTMGGFY | 111-113 | + | |
| 19 | KMLDNTMGGFY | K$^{111}$MLDNTMGGFY | 111-113 | + | |
| 20 | X$_1$X$_2$DNTMGGFYI | X$_1$$^{112}$X$_2$DNTMGGFYI | 112-113 | + | + |
| 21 | MLDNTMGGFYI | M$^{112}$X$_2$DNTMGGFYI | 112-113 | + | + |
| 22 | X$_2$DNTMGGFYIA | X$_2$$^{113}$DNTMGGFYIA | 113 | + | + |
| 23 | LDNTMGGFYIA | L$^{113}$DNTMGGFYIA | 113 | + | + |
| 24 | SQGLKX$_1$X$_2$DNTM | S$^{107}$QGLKX$_1$X$_2$DNTM | 111-113 | + | + |
| 25 | SQGLKMLDNTM | S$^{107}$QGLKMLDNTM | 111-113 | + | + |
| 26 | KNFMX$_4$LPNI | K$^{138}$NFMX$_4$LPNI | 142 | + | |
| 27 | KNFMALPNI | K$^{138}$NFMALPNI | 142 | + | |
| 28 | ELVFSKMGI | E$^{167}$LVFSKMGI | 171 | + | |
| 29 | NIGKKLVNS | N$^{359}$IGKKLVNS | 363 | + | |
| 30 | KMTIDKLME | K$^{378}$MTIDKLME | 382 | + | + |
| 31 | MEYGHMLY | M$^{385}$EYGHMLY | 389 | + | |
| 32 | MLVREQEN | M$^{391}$VREQEN | 393 | + | |
| 33 | DKLMEYGHMLVR | D$^{382}$KLMEYGHMLVR | 382, 389, 393 | + | |
| 34 | NVKRVQLAD | N$^{397}$VKRVQLAD | 405 | + | |
| 35 | KYLSEAALG | K$^{406}$YLSEAALG | 406 | + | + |
| 36 | VQLADKYLSE | V$^{401}$QLADKYLSE | 405, 406 | + | + |
| 37 | GAQQGGNLP | G$^{439}$AQQGGNLP | 434 | + | |
| 38 | See Table 2 | NA | | | |
| 39 | See Table 2 | NA | | | |
| 40 | See Table 2 | NA | | | |
| 41 | See Table 3 | NA | | | |
| 42 | See Table 3 | NA | | | |
| 43 | See Table 2 | NA | | | |
| 44 | See Table 3 | NA | | | |
| 45 | SFYGAAPSS | S$^{425}$FYGAAPSS | 429 | | |
| 46 | See Table 5 | NA | | | |
| 47 | See Table 5 | NA | | | |
| 48 | See Table 5 | NA | | | |
| 49 | See Table 5 | NA | | | |
| 50 | See Table 6 | NA | | | |
| 51 | See Table 6 | NA | | | |

TABLE 1-continued

Sequence identification

| SEQ ID NO | Sequence | Relative position* | change in Oa occurs at the following corresponding position in the Os seq | High heat stress[a] | High heat stress[b] |
|---|---|---|---|---|---|
| 52 | See Table 6 | NA | | | |
| 53 | See Table 7 | NA | | | |

$X_1$ = charged (K, R, N, M, Q, H, D, E)
$X_2$ = aliphatic (L, I, V)
$X_3$ = positive charged (K, R, N, M, Q, H)
$X_4$ = small (A, G)
[a] = residue found in relevant position in O. *australiensis* Rubisco activase
[b] = residue found in analogous position in Rubisco activase of warm-adapted species *Gossypium hirsutum* (cotton) and *Larrea tridentate* (creosote bush).
* = Position relative to SEQ ID No: 38 (BAC78572.1)

TABLE 2

Rubisco Activase RCA (RCA) polypeptide Sequences

| SEQ ID NO: | Sequence |
|---|---|
| 38 | MAAAFSSTVGAPASTPTNFLGKKLKKQVTSAVNYHGKSSNINRFKVMAK ELDEGKQTDQDRWKGLAYDISDDQQDITRGKGFVDSLFQAPTGDGTHEA VLSSYEYLSQGLRTYDFDNTMGGFYIAPAFMDKLVVHISKNFMTLPNIK VPLILGIWGGKGQGKSFQCELVFAKMGINPIMMSAGELESGNAGEPAKL IRQRYREAADIIKKGKMCCLFINDLDAGAGRMGGTTQYTVNNQMVNATL MNIADNPTNVQLPGMYNKEDNPRVPIIVTGNDFSTLYAPLIRDGRMEKF YWAPTRDDRVGVCKGIFRTDNVPDEDIVKIVDSFPGQSIDFFGALRARV YDDEVRKWVSDTGVENIGKRLVNSREGPPEFEQPKMTIEKLMEYGYMLV KEQENVKRVQLAEQYLSEAALGDANSDAMKTGSFYGSAPSS |
| 39 | MAAAFSSTVGAPASTPTNFLGKKLKKQVTSAVNYHGKSSNINRFKVMAK ELDEDKQTDQDKWKGLAYDISDDQQDITRGKGLVDSLFQAPMGDGTHEA VLSSYEYLSQGLKMLDNTMGGFYIAPAFMDKLVVHISKNFMALPNIKVP LILGIWGGKGQGKSFQCELVFSKMGINPIMMSAGELESGNAGEPAKLIR QRYREAADIIKKGKMCCLFINDLDAGAGRMGGTTQYTVNNQMVNATLMN IADNPTNVQLPGMYNKEDNPRVPIIVTGNDFSTLYAPLIRDGRMEKFYW APTRDDRVGVCKGIFRTDNVPDEDIVKIVDSFPGQSIDFFGALRARVYD DEVRKWVSDTGVENIGKKLVNSREGPPEFEQPKMTIDKLMEYGHMLVRE QENVKRVQLADKYLSEAALGDANSDAMKTGSFYGQGAQQGGNLPVPEGC TDPVAKNFDPTARSDDGSCLYTF |
| 40 | MAAAFSSTVGAPASTPTNFLGKKLKKQVTSAVNYHGKSSNINRFKVMAK ELDEDKQTDQDKWKGLAYDISDDQQDITRGKGLVDSLFQAPMGDGTHEA VLSSYEYLSQGLKMLDNTMGGFYIAPAFMDKLVVHISKNFMALPNIKVP LILGIWGGKGQGKSFQCELVFSKMGINPIMMSAGELESGNAGEPAKLIR QRYREAADIIKKGKMCCLFINDLDAGAGRMGGTTQYTVNNQMVNATLMN IADNPTNVQLPGMYNKEDNPRVPIIVTGNDFSTLYAPLIRDGRMEKFYW APTRDDRVGVCKGIFRTDNVPDEDIVKIVDSFPGQSIDFFGALRARVYD DEVRKWVSDTGVENIGKKLVNSREGPPEFEQPKMTIDKLMEYGHMLVRE QENVKRVQLADKYLSEAALGDANSDAMKTGSFYGAAPSS |
| 43 | MAAAFSSTVGAPASTPTNFLGKKLKKQVTSAVNYHGKSSNINRFKVMAK ELDEGKQTDQDRWKGLAYDISDDQQDITRGKGFVDSLFQAPTGDGTHEA VLSSYEYLSQGLRTYDFDNTMGGFYIAPAFMDKLVVHISKNFMTLPNIK VPLILGIWGGKGQGKSFQCELVFAKMGINPIMMSAGELESGNAGEPAKL IRQRYREAADIIKKGKMCCLFINDLDAGAGRMGGTTQYTVNNQMVNATL MNIADNPTNVQLPGMYNKEDNPRVPIIVTGNDFSTLYAPLIRDGRMEKF YWAPTRDDRVGVCKGIFRTDNVPDEDIVKIVDSFPGQSIDFFGALRARV YDDEVRKWVSDTGVENIGKRLVNSREGPPEFEQPKMTIEKLMEYGYMLV KEQENVKRVQLAEQYLSEAALGDANSDAMKTGSFYGQGAQQAGNLPVPE GCTDPVAKNFDPTARSDDGSCLYTF |

TABLE 3

Rubisco Activase (RCA) nucleotide sequences

| SEQ ID NO: | Sequence |
|---|---|
| 1 | ATGGCTGCTGCCTTCTCCTCCACCGTTGGAGCTCCGGCGTCCACTCCGA<br>CCAACTTCCTGGGGAAGAAGCTGAAAAAGCAGGTGACATCGGCGGTGAA<br>CTACCATGGCAAGAGCTCCAACATCAACAGGTTCAAGGTGATGGCCAAG<br>GAGCTGGACGAGGGCAAGCAGACCGACCAGGACAGGTGGAAGGGTCTCG<br>CCTACGACATCTCCGATGACCAGCAGGACATCACCAGGGGGAAGGGTTT<br>CGTCGACTCCCTTTTCCAGGCTCCCACGGGTGATGGCACCCACGAGGCC<br>GTCCTCAGCTCCTACGAGTACCTCAGCCAGGGTCTCAGAACGTACGACT<br>TCGACAACACCATGGGAGGCTTCTACATCGCCCCTGCTTTCATGGACAA<br>GCTCGTCGTCCACATCTCCAAGAACTTCATGACCCTCCCCAACATCAAG<br>GTCCCACTCATCCTGGGTATCTGGGGAGGCAAGGGTCAGGGAAAATCCT<br>TCCAGTGTGAGCTCGTCTTCGCCAAGATGGGGATCAACCCCATCATGAT<br>GAGCGCCGGAGAGCTGGAGAGCGGCAACGCCGGAGAGCCGGCGAAGCTG<br>ATCAGGCAGCGGTACCGTGAGGCGGCAGACATCATCAAGAAGGGGAAGA<br>TGTGCTGCCTCTTCATCAACGATCTGGACGCGGGTGCAGGTCGCATGGG<br>AGGCACCCACCCAGTACACGGTGAACAACCAGATGGTGAACGCCACCCTG<br>ATGAACATCGCCGACAACCCAACCAACGTGCAGCTCCCCGGGATGTACA<br>ACAAGGAGGACAACCCCCGTGTCCCCATCATCGTCACCGGCAACGACTT<br>CTCCACGCTGTACGCGCCGCTCATCCGTGACGGGCGTATGGAGAAGTTC<br>TACTGGGCTCCCACCCGCGACGACCGTGTCGGCGTCTGCAAGGGTATCT<br>TCCGCACCGACAACGTCCCCGACGAGGACATCGTCAAGATCGTCGACAG<br>CTTCCCAGGCCAATCCATCGATTTCTTCGGCGCTCTTCGTGCCCGTGTT<br>TACGACGACGAGGTGCGCAAGTGGGTGTCGGACACGGGTGTGGAGAACA<br>TTGGCAAGAGGCTGGTGAACTCGAGGGAGGGCCCACCGGAGTTCGAGCA<br>GCCCAAGATGACGATCGAAAAGCTCATGGAGTACGGATACATGCTTGTG<br>AAGGAGCAGGAGAACGTCAAGCGTGTGCAGCTGGCTGAGCAGTACTTGA<br>GCGAGGCTGCTCTTGGTGACGCTAACTCCGACGCCATGAAGACTGGTTC<br>CTTCTACGGTTCTGCGCCATCCAGCTGA |
| 41 | ATGGCTGCTGCCTTCTCCTCCACCGTTGGAGCTCCGGCCTCCACTCCGA<br>CCAACTTCCTGGGGAAGAAGCTGAAGAAGCAGGTGACATCGGCCGTGAA<br>CTACCATGGCAAGAGCTCCAACATCAACAGGTTCAAAGTGATGGCCAAG<br>GAGCTCGACGAGGACAAGCAGACCGACCAGGACAAGTGGAAGGGTCTCG<br>CCTACGACATCTCCGATGACCAGCAGGACATCACCAGGGGGAAGGGTCT<br>CGTCGACTCCCTCTTCCAGGCTCCCATGGGTGATGGCACCCACGAGGCC<br>GTCCTCAGCTCCTACGAGTACCTCAGCCAGGGTCTCAAAATGTTGGACA<br>ACACCATGGGAGGCTTCTACATCGCCCCGGCTTTCATGGACAAGCTCGT<br>CGTCCACATCTCCAAGAACTTCATGGCCCTCCCCAACATCAAGGTCCCA<br>CTCATCCTGGGTATCTGGGGAGGCAAGGGTCAGGGAAAATCCTTCCAGT<br>GTGAGCTCGTCTTCTCCAAGATGGGGATCAACCCCATCATGATGAGTGC<br>CGGAGAGCTGGAGAGCGGCAACGCCGGAGAGCCCGCGAAGCTCATCAGG<br>CAGCGGTATCGTGAGGCGGCGGACATCATCAAGAAGGGGAAGATGTGCT<br>GCCTCTTCATCAACGATCTCGACGCCGGAGCAGGTCGCATGGGCGGCAC<br>CACCCAGTACACGGTGAACAACCAGATGGTGAACGCCACCCTGATGAAC<br>ATCGCCGACAACCCAACCAACGTGCAGCTGCCGGGCATGTACAACAAGG<br>AGGACAACCCCCGTGTCCCCATCATCGTCACCGGTAACGACTTCTCGAC<br>GCTGTACGCGCCGCTCATCCGTGACGGGCGTATGGAGAAGTTCTACTGG<br>GCTCCCACCCGCGATGACCGTGTCGGCGTCTGCAAGGGTATCTTCCGCA<br>CCGACAACGTCCCCGACGAGGACATCGTCAAAATCGTGGACAGCTTCCC<br>AGGCCAATCCATCGATTTCTTCGGTGCTCTGCGTGCCCGTGTTTACGAC<br>GACGAGGTGCGCAAGTGGGTGTCGGACACCGGTGTGGAGAACATTGGCA<br>AGAAGCTGGTGAACTCGAGGGAGGGCCCACCGGAGTTCGAGCAGCCCAA<br>GATGACGATCGACAAGCTGATGGAGTACGGACACATGCTTGTGAGGGAG<br>CAGGAGAACGTCAAGCGTGTGCAGCTGGCTGACAAGTACTTGAGCGAGG<br>CTGCTCTTGGTGACGCTAACTCCGACGCCATGAAGACTGGTTCCTTCTA<br>CGGT<u>G</u>CTGCGCCATCCAGCTGA |
| 42 | ATGGCTGCTGCCTTCTCCTCCACCGTTGGAGCTCCGGCCTCCACTCCGA<br>CCAACTTCCTGGGGAAGAAGCTGAAGAAGCAGGTGACATCGGCCGTGAA<br>CTACCATGGCAAGAGCTCCAACATCAACAGGTTCAAAGTGATGGCCAAG<br>GAGCTCGACGAGGACAAGCAGACCGACCAGGACAAGTGGAAGGGTCTCG<br>CCTACGACATCTCCGATGACCAGCAGGACATCACCAGGGGGAAGGGTCT<br>CGTCGACTCCCTCTTCCAGGCTCCCATGGGTGATGGCACCCACGAGGCC<br>GTCCTCAGCTCCTACGAGTACCTCAGCCAGGGTCTCAAAATGTTGGACA<br>ACACCATGGGAGGCTTCTACATCGCCCCGGCTTTCATGGACAAGCTCGT<br>CGTCCACATCTCCAAGAACTTCATGGCCCTCCCCAACATCAAGGTCCCA<br>CTCATCCTGGGTATCTGGGGAGGCAAGGGTCAGGGAAAATCCTTCCAGT<br>GTGAGCTCGTCTTCTCCAAGATGGGGATCAACCCCATCATGATGAGTGC<br>CGGAGAGCTGGAGAGCGGCAACGCCGGAGAGCCCGCGAAGCTCATCAGG<br>CAGCGGTATCGTGAGGCGGCGGACATCATCAAGAAGGGGAAGATGTGCT<br>GCCTCTTCATCAACGATCTCGACGCCGGAGCAGGTCGCATGGGCGGCAC<br>CACCCAGTACACGGTGAACAACCAGATGGTGAACGCCACCCTGATGAAC<br>ATCGCCGACAACCCAACCAACGTGCAGCTGCCGGGCATGTACAACAAGG<br>AGGACAACCCCCGTGTCCCCATCATCGTCACCGGTAACGACTTCTCGAC<br>GCTGTACGCGCCGCTCATCCGTGACGGGCGTATGGAGAAGTTCTACTGG<br>GCTCCCACCCGCGATGACCGTGTCGGCGTCTGCAAGGGTATCTTCCGCA<br>CCGACAACGTCCCCGACGAGGACATCGTCAAAATCGTGGACAGCTTCCC |

TABLE 3-continued

Rubisco Activase (RCA) nucleotide sequences

| SEQ ID NO: | Sequence |
|---|---|
|  | AGGCCAATCCATCGATTTCTTCGGTGCTCTGCGTGCCCGTGTTTACGAC<br>GACGAGGTGCGCAAGTGGGTGTCGGACACCGGTGTGGAGAACATTGGCA<br>AGAAGCTGGTGAACTCGAGGGAGGGCCCACCGGAGTTCGAGCAGCCCAA<br>GATGACGATCGACAAGCTGATGGAGTACGGACACATGCTTGTGAGGGAG<br>CAGGAGAACGTCAAGCGTGTGCAGCTGGCTGACAAGTACTTGAGCGAGG<br>CTGCTCTTGGTGACGCTAACTCCGACGCCATGAAGACTGGTTCCTTCTA<br>CGGGCAAGGAGCACAGCAAGGAGGTAACCTGCCTGTGCCGGAAGGTTGC<br>ACCGACCCTGTTGCCAAGAACTTCGACCCAACGGCGAGGAGCGACGACG<br>GCAGCTGCCTTTACACCTTTTAA |
| 44 | ATGGCTGCTGCCTTCTCCTCCACCGTTGGAGCTCCGGCGTCCACTCCGA<br>CCAACTTCCTGGGGAAGAAGCTGAAGAAGCAGGTGACATCGGCGGTGAA<br>CTACCATGGCAAGAGCTCCAACATCAACAGGTTCAAGGTGATGGCCAAG<br>GAGCTGGACGAGGGCAAGCAGACCGACCAGGACAGGTGGAAGGGTCTCG<br>CCTACGACATCTCCGATGACCAGCAGGACATCACCAGGGGGAAGGGTTT<br>CGTCGACTCCCTTTTCCAGGCTCCCACGGGTGATGGCACCCACGAGGCC<br>GTCCTCAGCTCCTACGAGTACCTCAGCCAGGGTCTCAGAACGTACGACT<br>TCGACAACACCATGGGAGGCTTCTACATCGCCCCTGCTTTCATGGACAA<br>GCTCGTCGTCCACATCTCCAAGAACTTCATGACCCTCCCCAACATCAAG<br>GTCCCACTCATCCTGGGTATCTGGGGAGGCAAGGGTCAGGGAAAATCCT<br>TCCAGTGTGAGCTCGTCTTCGCCAAGATGGGGATCAACCCCATCATGAT<br>GAGCGCCGAGAGCTGGAGAGCGGCAACGCCGGAGAGCCGGCGAAGCTG<br>ATCAGGCAGCGGTACCGTGAGGCGGCAGACATCATCAAGAAGGGGAAGA<br>TGTGCTGCCTCTTCATCAACGATCTGGACGCGGGTGCAGGTCGCATGGG<br>AGGCACCACCCAGTACACGGTGAACAACCAGATGGTGAACGCCACCCTG<br>ATGAACATCGCCGACAACCCAACCAACGTGCAGCTCCCCGGGATGTACA<br>ACAAGGAGGACAACCCCCGTGTCCCCATCATCGTCACCGGCAACGACTT<br>CTCCACGCTGTACGCGCCGCTCATCCGTGACGGGCGTATGGAGAAGTTC<br>TACTGGGCTCCCACCCGCGACGACCGTGTCGGCGTCTGCAAGGGTATCT<br>TCCGCACCGACAACGTCCCCGACGAGGACATCGTCAAGATCGTCGACAG<br>CTTCCCAGGCCAATCCATCGATTTCTTCGGCGCTCTTCGTGCCCGTGTT<br>TACGACGACGAGGTGCGCAAGTGGGTGTCGGACACGGGTGTGGAGAACA<br>TTGGCAAGAGGCTGGTGAACTCGAGGGAGGGCCCACCGGAGTTCGAGCA<br>GCCCAAGATGACGATCGAAAAGCTCATGGAGTACGGATACATGCTTGTG<br>AAGGAGCAGGAGAACGTCAAGCGTGTGCAGCTGGCTGAGCAGTACTTGA<br>GCGAGGCTGCTCTTGGTGACGCTAACTCCGACGCCATGAAGACTGGTTC<br>CTTCTACGGGCAAGGAGCACAGCAAGCAGGTAACCTGCCTGTGCCGGAA<br>GGTTGCACCGACCCTGTTGCCAAGAACTTCGACCCAACGGCGAGGAGCG<br>ACGACGGCAGCTGCCTTTACACCTTTTAA |

TABLE 4

Sequence information

| SEQ ID NO: | Information |
|---|---|
| 1 | Nucleotide sequence of short form of Rubisco activase from O. sativa ssp. japonica cv. Nipponbare |
| 38 | Amino acid sequence Rubisco activase from O. sativa ssp. japonica cv. Nipponbare (>gi \|891836l\| dbj \| BAA97584.1\| ribulose-bisphosphate carboxylase activase small isoform precursor protein [Oryza sativa japonica subspecies]) |
| 39 | Amino acid sequence of long form of Rubisco activase from O. australiensis |
| 40 | Amino acid sequence of short form of Rubisco activase from O. australiensis |
| 41 | Nucleotide sequence of short form of Rubisco activase nucleic acid from O. australiensis |
| 42 | Nucleotide sequence of long form of Rubisco activase nucleic acid from O. australiensis |
| 43 | Amino acid sequence of Rubisco activase from O. sativa ssp. japonica cv. Nipponbare (>gi \|323521581\| dbj \| BAC78572.1) Rubisco activase long isoform precursor protein [Oryza sativa japonica subspecies]) |
| 44 | Nucleotide sequence of long form of Rubisco activase from O. sativa ssp. japonica cv. Nipponbare |
| 50 | Nucleotide sequence of long form of Rubisco activase nucleic acid from O. australiensis (adapted to rice codon usage), used for vector pTNVS299 |
| 51 | Nucleotide sequence of short form of Rubisco activase nucleic acid from O. australiensis (adapted to rice codon usage) with a 5AA truncation at the end of the gene, used for vector pTKAW39 |
| 52 | Nucleotide sequence of short form of Rubisco activase nucleic acid from O. australiensis (adapted to rice codon usage), used for vector pTKAW40 |
| 53 | Nucleotide sequence of the promoter of Rubisco activase from O. meridionalis, used for vectors pTNVS299, pTKAW39, pTKAW40 |
| 54 | Nucleotide sequence of Rubisco activase from O. meridionalis |
| 55 | Amino acid sequence of O. meridionalis alpha protein |

TABLE 4-continued

Sequence information

| SEQ ID NO: | Information |
|---|---|
| 56 | Amino acid sequence of *O. meridionalis* beta protein |
| 57 | Amino acid sequence of *Descampsia antarctica* protein |
| 58 | Amino acid sequence of *Gossypium hirsutum* protein |
| 59 | Amino acid sequence of *Larrea tridentata* protein |
| 60 | Amino acid sequence of *Spinacia oleracea* protein |

TABLE 5

RCA genes adapted to *E. coli* usage

| SEQ ID NO: | Sequence |
|---|---|
| 46 | ATGGCTAAAGAACTGGACGAAGGCAAACAGACTGATCAGGACCGCTGGA<br>AAGGTCTGGCCTACGATATTTCCGATGACCAGCAGGATATCACCCGCGG<br>TAAAGGCTTCGTAGATTCTCTGTTCCAGGCGCCAACTGGTGATGGTACT<br>CATGAAGCGGTTCTGAGCTCCTACGAATATCTGAGCCAGGGTCTGCGTA<br>CCTATGACTTCGACAACACTATGGGCGGTTTTTACATCGCTCCGGCTTT<br>CATGGACAAACTGGTCGTCCACATCTCCAAAAACTTCATGACCCTGCCG<br>AACATCAAAGTGCCACTGATTCTCGGCATCTGGGGTGGCAAAGGTCAGG<br>GCAAATCCTTCCAGTGTGAACTGGTCTTCGCGAAAATGGGCATTAACCC<br>GATCATGATGAGCGCAGGTGAACTGGAATCTGGTAACGCCGGTGAACCG<br>GCGAAACTGATTCGTCAGCGTTACCGTGAAGCGGCCGACATCATCAAAA<br>AAGGCAAAATGTGCTGCCTGTTCATCAACGATCTGGATGCTGGTGCAGG<br>TCGTATGGGTGGCACTACCCAGTATACCGTGAACAACCAGATGGTTAAC<br>GCCACCCTGATGAACATTGCCGATAACCCGACTAACGTACAGCTGCCGG<br>GCATGTATAACAAAGAAGACAACCCGCGCGTTCCGATCATTGTTACCGG<br>CAACGACTTCTCTACGCTGTATGCTCCGCTGATTCGTGATGGCCGTATG<br>GAGAAATTCTACTGGGCACCAACCCGTGACGACCGTGTTGGTGTATGCA<br>AAGGTATCTTCCGCACCGATAACGTTCCGGACGAAGACATCGTCAAAAT<br>CGTGGACAGCTTTCCGGGCCAGTCTATCGATTTCTTTGGCGCTCTGCGT<br>GCTCGTGTTTACGACGACGAAGTTCGCAAATGGGTGTCTGATACGGGTG<br>TGGAAAACATCGGCAAACGTCTGGTTAACTCTCGTGAAGGTCCACCGGA<br>GTTCGAACAGCCGAAAATGACGATCGAGAAACTGATGGAGTACGGCTAC<br>ATGCTGGTGAAAGAGCAGGAGAACGTGAAACGTGTACAGCTGGCAGAAC<br>AGTACCTGAGCGAAGCTGCACTGGGTGATGCGAACTCTGACGCGATGAA<br>AACTGGCTCCTTTTATGGTCAGGGTGCACAGCAGGCAGGTAACCTCCCA<br>GTACCAGAAGGTTGTACCGACCCAGTTGCGAAAAACTTTGACCCAACCG<br>CTCGCTCTGATGACGGTTCTTGCCTGTACACCTTCTAA |
| 47 | ATGGCCAAAGAACTGGACGAAGACAAACAGACCGACCAGGACAAATGGA<br>AAGGTCTGGCCTACGACATCTCTGATGACCAGCAGGATATCACCCGTGG<br>CAAAGGCCTGGTAGATTCTCTGTTCCAGGCTCCGATGGGTGATGGTACT<br>CATGAGGCGGTTCTGTCTTCCTATGAGTACCTGAGCCAGGGCCTGAAAA<br>TGCTGGATAACACTATGGGTGGCTTCTACATTGCACCGGCCTTTATGGA<br>CAAACTGGTCGTCCACATCTCCAAAAACTTCATGGCCCTGCCGAACATC<br>AAAGTCCCGCTGATTCTGGGTATTTGGGGTGGCAAAGGTCAGGGCAAAT<br>CCTTCCAGTGCGAACTGGTCTTCAGCAAAATGGGCATCAACCCGATCAT<br>GATGAGCGCTGGTGAACTGGAATCTGGTAACGCTGGCGAACCGGCTAAA<br>CTGATTCGTCAGCGTTACCGCGAAGCGGCCGACATCATCAAAAAAGGCA<br>AAATGTGCTGCCTGTTCATCAACGATCTGGATGCAGGTGCAGGTCGTAT<br>GGGTGGCACTACCCAGTATACCGTGAACAACCAGATGGTGAACGCGACC<br>CTGATGAACATCGCGGATAACCCAACCAACGTTCAGCTGCCGGGCATGT<br>ACAACAAAGAAGACAACCCGCGTGTCCCGATTATCGTTACCGGCAACGA<br>CTTCTCCACTCTCTATGCTCCGCTGATCCGTGACGGCCGTATGGAAAAA<br>TTCTACTGGGCACCGACTCGCGACGATCGTGTAGGCGTGTGTAAAGGTA<br>TCTTCCGTACCGACAACGTCCCAGACGAGGACATTGTGAAAATCGTGGA<br>CAGCTTTCCGGGCCAGTCTATTGATTTCTTTGGCGCTCTGCGTGCACGT<br>GTATACGACGATGAAGTCCGCAAATGGGTTAGCGACACGGGTGTTGAGA<br>ACATCGGCAAAAAACTGGTGAACTCCCGTGAAGGTCCACCGGAATTTGA<br>GCAGCCGAAAATGACGATCGACAAACTGATGGAGTACGGTCACATGCTG<br>GTACGCGAACAGGAAAACGTGAAACGTGTGCAGCTGGCGGATAAATACC<br>TGAGCGAAGCAGCTCTGGGTGATGCTAACTCCGATGCGATGAAAACCGG<br>CTCTTTCTATGGTCAGGGTGCACAGCAGGGCGGTAACCTGCCAGTACCG<br>GAAGGTTGTACTGATCCGGTTGCGAAAAACTTCGATCCAACGGCTCGCT<br>CTGATGACGGTTCTTGCCTCTATACCTTTGCGGGTCGCTAA |
| 48 | ATGGCTAAAGAACTGGACGAAGGCAAACAGACTGATCAGGACCGCTGGA<br>AAGGTCTGGCCTACGATATTTCCGATGACCAGCAGGATATCACCCGCGG<br>TAAAGGCTTCGTAGATTCTCTGTTCCAGGCGCCAACTGGTGATGGTACT<br>CATGAAGCGGTTCTGAGCTCCTACGAATATCTGAGCCAGGGTCTGCGTA<br>CCTATGACTTCGACAACACTATGGGCGGTTTTTACATCGCTCCGGCTTT<br>CATGGACAAACTGGTCGTCCACATCTCCAAAAACTTCATGACCCTGCCG<br>AACATCAAAGTGCCACTGATTCTCGGCATCTGGGGTGGCAAAGGTCAGG |

TABLE 5-continued

RCA genes adapted to E. coli usage

| SEQ ID NO: | Sequence |
|---|---|
| | GCAAATCCTTCCAGTGTGAACTGGTCTTCGCGAAAATGGGCATTAACCC<br>GATCATGATGAGCGCAGGTGAACTGGAATCTGGTAACGCCGGTGAACCG<br>GCGAAACTGATTCGTCAGCGTTACCGTGAAGCGGCCGACATCATCAAAA<br>AAGGCAAAATGTGCTGCCTGTTCATCAACGATCTGGATGCTGGTGCAGG<br>TCGTATGGGTGGCACTACCCAGTATACCGTGAACAACCAGATGGTTAAC<br>GCCACCCTGATGAACATTGCCGATAACCCGACTAACGTACAGCTGCCGG<br>GCATGTATAACAAAGAAGACAACCCGCGCGTTCCGATCATTGTTACCGG<br>CAACGACTTCTCTACGCTGTATGCTCCGCTGATTCGTGATGGCCGTATG<br>GAGAAATTCTACTGGGCACCAACCCGTGACGACCGTGTTGGTGTATGCA<br>AAGGTATCTTCCGCACCGATAACGTTCCGGACGAAGACATCGTCAAAAT<br>CGTGGACAGCTTTCCGGGCCAGTCTATCGATTTCTTTGGCGCTCTGCGT<br>GCTCGTGTTTACGACGACGAAGTTCGCAAATGGGTGTCTGATACGGGTG<br>TGGAAAACATCGGCAAACGTCTGGTTAACTCTCGTGAAGGTCCACCGGA<br>GTTCGAACAGCCGAAAATGACGATCGAGAAACTGATGGAGTACGGCTAC<br>ATGCTGGTGAAAGAGCAGGAGAACGTGAAACGTGTACAGCTGGCAGAAC<br>AGTACCTGAGCGAAGCTGCACTGGGTGATGCGAACTCTGACGCGATGAA<br>AACTGGCTCCTTTTATGGTTCCGCGCCGTCTTCCTAA |
| 49 | ATGGCCAAAGAACTGGACGAAGACAAACAGACCGACCAGGACAAATGGA<br>AAGGTCTGGCGTACGACATCTCTGATGACCAGCAGGATATCACCCGTGG<br>CAAAGGCCTGGTAGATTCTCTGTTCCAGGCTCCGGATGGGTGATGGTACT<br>CATGAGGCGGTTCTGTCTTCCTATGAGTACCTGAGCCAGGGCCTGAAAA<br>TGCTGGATAACACTATGGGTGGCTTCTACATTGCACCGGCCTTTATGGA<br>CAAACTGGTCGTCCACATCTCCAAAAACTTCATGGCCCTGCCGAACATC<br>AAAGTCCCGCTGATTCTGGGTATTTGGGGTGGCAAAGGTCAGGGCAAAT<br>CCTTCCAGTGCGAACTGGTCTTCAGCAAAATGGGCATCAACCCGATCAT<br>GATGAGCGCTGGTGAACTGGAATCTGGTAACGCTGGCGAACCGGCTAAA<br>CTGATTCGTCAGCGTTACCGCGAAGCGGCCGACATCATCAAAAAAGGCA<br>AAATGTGCTGCCTGTTCATCAACGATCTGGATGCAGGTGCAGGTCGTAT<br>GGGTGGCACTACCCAGTATACCGTGAACAACCAGATGGTGAACGCGACC<br>CTGATGAACATCGCGGATAACCCAACCAACGTTCAGCTGCCGGGCATGT<br>ACAACAAAGAAGACAACCCGCGTGTCCCGATTATCGTTACCGGCAACGA<br>CTTCTCCACTCTCTATGCTCCGCTGATCCGTGACGGCCGTATGGAAAAA<br>TTCTACTGGGCACCGACTCGCGACGATCGTGTAGGCGTGTGTAAAGGTA<br>TCTTCCGTACCGACAACGTCCCAGACGAGGACATTGTGAAAATCGTGGA<br>CAGCTTTCCGGGCCAGTCTATTGATTTCTTTGGCGCTCTGCGTGCACGT<br>GTATACGACGATGAAGTCCGCAAATGGGTTAGCGACACGGGTGTTGAGA<br>ACATCGGCAAAAAACTGGTGAACTCCCGTGAAGGTCCACCGGAATTTGA<br>GCAGCCGAAAATGACGATCGACAAACTGATGGAGTACGGTCACATGCTG<br>GTACGCGAACAGGAAAACGTGAAACGTGTGCAGCTGGCGGATAAATACC<br>TGAGCGAAGCAGCTCTGGGTGATGCTAACTCCGATGCGATGAAAACCGG<br>CTCTTTCTATGGTGCAGCGCCGTCTTCCTAA |

TABLE 6

RCA genes adapted to rice codon usage

| SEQ ID NO: | Sequence |
|---|---|
| 50 | ATGGCTGCTGCCTTCTCCTCGACAGTTGGAGCACCTGCCTCTACACCGA<br>CAAACTTCCTGGGCAAGAAGCTGAAGAAGCAAGTGACATCCGCCGTGAA<br>CTACCACGGCAAGCTCCAACATAAACCGCTTCAAAGTCATGGCGAAG<br>GAGCTCGATGAGGACAAGCAGACCGATCAGGACAAGTGGAAGGGACTTG<br>CCTACGACATCTCCGATGACCAGCAGGACATTACGAGGGGCAAAGGTTT<br>GGTCGACTCCCTTTTCCAAGCACCAATGGGAGATGGCACGCACGAAGCA<br>GTCCTTAGCTCCTACGAGTACCTCTCCCAGGGCTTGAAGATGTTGACA<br>ACACTATGGGGGGCTTCTACATCGCACCTGCTTTCATGGACAAGCTCGT<br>CGTCCACATCTCGAAGAACTTCATGGCGCTCCCGAACATAAAGGTGCCA<br>CTGATTCTCGGGATCTGGGGAGGCAAGGGTCAGGGGAAATCCTTCCAGT<br>GTGAGCTCGTCTTCTCCAAGATGGGGATCAACCCCATCATGATGAGCGC<br>CGGAGAACTGGAAAGCGGAAATGCCGGAGAACCAGCGAAACTGATCCGA<br>CAGAGATACCGAGAGGCGGCTGACATCATCAAGAAGGGGAAGATGTGCT<br>GCCTCTTCATCAACGATCTGGATGCGGGAGCTGGCCGAATGGGAGGGAC<br>TACTCAATACACCGTCAACAACCAGATGGTGAACGCGACCCTGATGAAC<br>ATCGCGGATAATCCCACCAACGTGCAACTCCCTGGGATGTACAACAAGG<br>AGGACAATCCGCGAGTCCCCATCATCGTCACGGGCAATGATTTCTCGAC<br>ACTCTACGCCCCGCTTATCCGAGATGGGAGGATGGAGAAGTTCTACTGG<br>GCACCTACCAGAGACGATCGCGTAGGTGTCTGCAAAGGCATCTTTCGCA<br>CTGACAACGTCCCGGATGAGGACATCGTCAAGATCGTCGACAGCTTCCC<br>TGGCCAATCTATCGACTTTTTCGGCGCTCTACGAGCCCGTGTTTACGAT<br>GACGAAGTGCGGAAATGGGTTTCGGATACGGGCGTGGAGAACATTGGCA<br>AGAAACTGGTGAACTCTAGGGAAGGGCCACCTGAGTTCGAACAGCCGAA<br>GATGACGATCGACAAGCTCATGGAGTACGGCCATATGCTCGTGAGGGAG |

TABLE 6-continued

| RCA genes adapted to rice codon usage |
|---|

| SEQ ID NO: | Sequence |
|---|---|
|  | CAGGAGAACGTTAAGCGTGTTCAACTGGCCGACAAGTACCTAAGCGAGG |
|  | CAGCTTTGGGTGACGCTAACTCCGACGCCATGAAAACTGGTTCCTTCTA |
|  | CGGGCAAGGAGCACAGCAAGGCGGAAACTTACCTGTGCCGGAAGGTTGC |
|  | ACTGACCCCGTTGCGAAGAACTTTGACCCAACGGCGAGATCTGACGATG |
|  | GGAGCTGCCTTTATACCTTTTAA |
|  |  |
| 51 | ATGGCTGCTGCCTTCTCCTCGACAGTTGGAGCACCTGCCTCTACACCGA |
|  | CAAACTTCCTGGGCAAGAAGCTGAAGAAGCAAGTGACATCCGCCGTGAA |
|  | CTACCACGGCAAGAGCTCCAACATAAACCGCTTCAAAGTCATGGCGAAG |
|  | GAGCTCGATGAGGACAAGCAGACCGATCAGGACAAGTGGAAGGGACTTG |
|  | CCTACGACATCTCCGATGACCAGCAGGACATTACGAGGGGCAAAGGTTT |
|  | GGTCGACTCCCTTTTCCAAGCACCAATGGGAGATGGCACGCACGAAGCA |
|  | GTCCTTAGCTCCTACGAGTACCTCTCCCAGGGCTTGAAGATGTTGGACA |
|  | ACACTATGGGGGCTTCTACATCGCACCTGCTTTCATGGACAAGCTCGT |
|  | CGTCCACATCTCGAAGAACTTCATGGCGCTCCCGAACATAAAGGTGCCA |
|  | CTGATTCTCGGGATCTGGGGAGGCAAGGGTCAGGGGAAATCCTTCCAGT |
|  | GTGAGCTCGTCTTCTCCAAGATGGGGATCAACCCCATCATGATGAGCGC |
|  | CGGAGAACTGGAAAGCGGAAATGCCGGAGAACCAGCGAAACTGATCCGA |
|  | CAGAGATACCGAGAGGCGGCTGACATCATCAAGAAGGGGAAGATGTGCT |
|  | GCCTCTTCATCAACGATCTGGATGCGGGAGCTGGCCGAATGGGAGGGAC |
|  | TACTCAATACACCGTCAACAACCAGATGGTGAACGCGACCCTGATGAAC |
|  | ATCGCGGATAATCCCACCAACGTGCAACTCCCTGGGATGTACAACAAGG |
|  | AGGACAATCCGCGAGTCCCCATCATCGTCACGGGCAATGATTTCTCGAC |
|  | ACTCTACGCCCCGCTTATCCGAGATGGGAGGATGGAGAAGTTCTACTGG |
|  | GCACCTACCAGAGACGATCGCGTAGGTGTCTGCAAAGGCATCTTTCGCA |
|  | CTGACAACGTCCCGGATGAGGACATCGTCAAGATCGTCGACAGCTTCCC |
|  | TGGCCAATCTATCGACTTTTTCGGCGCTCTACGAGCCCGTGTTTACGAT |
|  | GACGAAGTGCGGAAATGGGTTTCGGATACGGGCGTGGAGAACATTGGCA |
|  | AGAAACTGGTGAACTCTAGGGAAGGGCCACCTGAGTTCGAACAGCCGAA |
|  | GATGACGATCGACAAGCTCATGGAGTACGGCCATATGCTCGTGAGGGAG |
|  | CAGGAGAACGTTAAGCGTGTTCAACTGGCCGACAAGTACCTAAGCGAGG |
|  | CAGCTTTGGGTGACGCTAACTCCGACGCCATGAAAACTGGTTCCTTCTA |
|  | CGGGTAA |
|  |  |
| 52 | ATGGCTGCTGCCTTCTCCTCGACAGTTGGAGCACCTGCCTCTACACCGA |
|  | CAAACTTCCTGGGCAAGAAGCTGAAGAAGCAAGTGACATCCGCCGTGAA |
|  | CTACCACGGCAAGAGCTCCAACATAAACCGCTTCAAAGTCATGGCGAAG |
|  | GAGCTCGATGAGGACAAGCAGACCGATCAGGACAAGTGGAAGGGACTTG |
|  | CCTACGACATCTCCGATGACCAGCAGGACATTACGAGGGGCAAAGGTTT |
|  | GGTCGACTCCCTTTTCCAAGCACCAATGGGAGATGGCACGCACGAAGCA |
|  | GTCCTTAGCTCCTACGAGTACCTCTCCCAGGGCTTGAAGATGTTGGACA |
|  | ACACTATGGGGGCTTCTACATCGCACCTGCTTTCATGGACAAGCTCGT |
|  | CGTCCACATCTCGAAGAACTTCATGGCGCTCCCGAACATAAAGGTGCCA |
|  | CTGATTCTCGGGATCTGGGGAGGCAAGGGTCAGGGGAAATCCTTCCAGT |
|  | GTGAGCTCGTCTTCTCCAAGATGGGGATCAACCCCATCATGATGAGCGC |
|  | CGGAGAACTGGAAAGCGGAAATGCCGGAGAACCAGCGAAACTGATCCGA |
|  | CAGAGATACCGAGAGGCGGCTGACATCATCAAGAAGGGGAAGATGTGCT |
|  | GCCTCTTCATCAACGATCTGGATGCGGGAGCTGGCCGAATGGGAGGGAC |
|  | TACTCAATACACCGTCAACAACCAGATGGTGAACGCGACCCTGATGAAC |
|  | ATCGCGGATAATCCCACCAACGTGCAACTCCCTGGGATGTACAACAAGG |
|  | AGGACAATCCGCGAGTCCCCATCATCGTCACGGGCAATGATTTCTCGAC |
|  | ACTCTACGCCCCGCTTATCCGAGATGGGAGGATGGAGAAGTTCTACTGG |
|  | GCACCTACCAGAGACGATCGCGTAGGTGTCTGCAAAGGCATCTTTCGCA |
|  | CTGACAACGTCCCGGATGAGGACATCGTCAAGATCGTCGACAGCTTCCC |
|  | TGGCCAATCTATCGACTTTTTCGGCGCTCTACGAGCCCGTGTTTACGAT |
|  | GACGAAGTGCGGAAATGGGTTTCGGATACGGGCGTGGAGAACATTGGCA |
|  | AGAAACTGGTGAACTCTAGGGAAGGGCCACCTGAGTTCGAACAGCCGAA |
|  | GATGACGATCGACAAGCTCATGGAGTACGGCCATATGCTCGTGAGGGAG |
|  | CAGGAGAACGTTAAGCGTGTTCAACTGGCCGACAAGTACCTAAGCGAGG |
|  | CAGCTTTGGGTGACGCTAACTCCGACGCCATGAAAACTGGTTCCTTCTA |
|  | CGGGGCCGCGCCGAGCTCCTGA |

TABLE 7

Promotor Sequence of Rubisco activase from *O. meridionalis*

| SEQ ID NO: | Sequence |
|---|---|
| 53 | GCCTCCGATTGATGCTTCACCAAAAAACAATATCAACAGCAGTGCAAAA<br>TTAGAATTTTTGTATTTTTGTGGTAACGCAAACCGGCCATCAAAGGGGA<br>AAAACGTACAATGCTTATGTTGTATGTTAAGAGAAGTTTGTGTGGTGCC<br>AAATGACAGTCCTAGCCTGACGGTTATCGAGAAAGCAGAATATGTGCAG<br>GTGGCAGAGCAAAATATTTGTGGTAGTCCAACTAGAATACAATTTGCAT<br>GCCATGCCTCATCCAAGAAGCCGGGCAACGAGAGGCAGCAAAAGGCTTT<br>TCTGTGGTGATGCAAAATGAAGAGGTTATGTAGTAGCTGAGCTGATGAA<br>GCAACTGGTCGCTAGCTGCCGGCCGGGAGACGAATGTGAGGCAAGGAAA<br>GAAAAGAAAAAACAGAGAGAAAGAGTTGATCAGAAATGGGTGAATTCTG<br>TGGTGAGGAAAGGTCAAGGAACTGAAGCCAAGAGATCCTTCCTACCTAC<br>ACTAATACAATACTCCTAACTCGCTCACAGACTCCGATCCAGGTCCAAG<br>TCATGCTATGCTGTGGATCGGCCGGCCGAGATTGCGCCACGTGTGCAGA<br>ACCCAATCTTCAGCGTGTGGCCTGTGGGGGATCTGGAAGCTGATCCACA<br>GGGAGGGAGGAGTGTGTGCCTCTCACAGCTTCCAACTTCCATGGCGACG<br>TCCAATGCTATTGTATTATTTAAGGCCTACCGCAGCTCGGCCTCTACAC<br>TTTGAGCAGCAGCGGCTGGCCATCATCAGTGATCCTCTACAATCATCGA<br>CTTTCAGCAAATTAAG |

It will be understood that the invention also encompasses complexes comprising Rubisco and RCA, e.g. as represented by SEQ ID NOs: 39 and 40, modified RCA or RCA-derived polypeptides which confer thermostability to the complex. The RCA, modified RCA or RCA-derived polypeptides include variants thereof, including substantially similar sequences, fragments, analogs, homologs, or mutants. The modified RCAs retain at least one function of RCA. These functions include, for example biological activities, such as activation of Rubisco or the ability to form a complex comprising Rubisco. In one embodiment, the polypeptides of the invention are at least 85%, 90%, 95%, 97%, 98% or 99% identical to the polypeptide sequence of any of SEQ ID NOs: 39 and 40. In some embodiments, the polypeptides of the invention are altered at 1, 2, 3, 4, 5, 6, 7, 8, 9, 10, 11, 12, 13, 14, 15, 16, 17, 18, positions corresponding to residues 54, 61, 82, 91, 111, 112, 113, 114, 115, 142, 171, 363, 382, 389, 393, 405, 406, 429 of SEQ ID NO: 38 *O. sativa* RCA. (i.e. the short RCA form) or corresponding to residues 54, 61, 82, 91, 111, 112, 113, 114, 115, 142, 171, 363, 382, 389, 393, 405, 406, 434 of the long form *O. sativa* RCA (SEQ ID NO: 43).

It will be understood that the invention also encompasses nucleic acids encoding polypeptides that can form complexes comprising Rubisco and RCA, e.g. as encoded by SEQ ID NOs: 50 to 52, or encoding modified RCA or RCA-derived polypeptides which confer thermostability to the complex. In one embodiment, the nucleic acids encoding polypeptides of the invention are at least 85%, 90%, 95%, 97%, 98% or 99% identical to the nucleic acid sequence of any of SEQ ID NOs: 50 to 52.

In another embodiment, polypeptides of the invention include fragments of RCA optionally having one or more of the above alterations. These fragments retain at least one function of RCA and are at least 25, 50, 75, 100, 125, 150, 175, 200, 225, 250, 275, 300, 325, 350, 375, 400 or 425 contiguous amino acids in length.

In another embodiment the RCA polypeptide of the invention comprises SEQ ID NO: 39 or 40.

In one embodiment, RCA polypeptide of the invention is a fragment that corresponds to a functional domain of RCA including, but not limited to, the ATP binding domain and the domain(s) that interacts with Rubisco. In some embodiments, polypeptides of the invention include domains of RCA such as the central ATPase domain (the AAA+ module), or at least one of the N-terminal P-loop NTPase alpha-beta-alpha subdomain or the C-terminal all-alpha subdomain. In some embodiments polypeptides of the invention include the C-terminal domain and/or the N-terminal domain of RCA. In the *O. australiensis* alpha RCA sequence, the delineations of the domains are as follows: N-terminal=1-55 residues; AAA+ motif=56-344; ATPase core=181-281; C-terminal=345-464. These delineations are based on the 3D structure of tobacco RCA (Stotz, M. et al. (2011) Nat. Struct. Mol. Biol. 18, 1366-1370) and the amino acid sequence alignment between Oa alpha RCA and tobacco RCA.

One or more residue substitutions, additions and/or deletions may be introduced into a wild-type RCA. For example 1, 2, 3, or between 4-10 or between 10-20 substitutions can be introduced and/or for example 1, 2, 3, or between 4-10 or between 10-20 additions can be introduced and/or for example 1, 2, 3, or between 4-10 or between 10-20 deletions can be introduced. For example, RCA polypeptides are generated to enhance a desirable characteristic (e.g. thermostability or the ability to form a complex with Rubisco). Alternatively RCA polypeptides may be generated to reduce an undesirable characteristic (e.g. a tendency to aggregate). In one embodiment, RCA polypeptides have improved thermostability over wild-type RCA. In another embodiment, RCA polypeptides of the invention have enzymatic activity under heat stress conditions (up to 40° C.) that is similar to or higher than the enzyme activity of same RCA under normal conditions (e.g. 30° C.).

Sequence alterations can be introduced by standard techniques such as directed molecular evolution techniques (e.g. DNA shuffling methods), oligonucleotide-directed mutagenesis, chemical mutagenesis, cassette mutagenesis, saturation mutagenesis and gene editing. In some embodiments sequence alterations may lead to one or more conservative or non-conservative amino acid substitutions at targeted sites. In other embodiments random mutagenesis is used to generate RCA nucleic acid molecules.

A 'non-conservative amino acid substitution' is a substitution in which the amino acid residue is substituted for an amino acid residue with a dissimilar side chain. Amino acid residues with similar side chains are known in the art. For example there are amino acids with basic side chains (e.g., lysine, arginine, histidine), acidic side chains (e.g., aspartic acid, glutamic acid, asparagine, glutamine), uncharged polar side chains (e.g., glycine, serine, threonine, tyrosine, cysteine), nonpolar side chains (e.g., alanine, valine, leucine, isoleucine, proline, phenylalanine, methionine, tryptophan), branched side chains (e.g., threonine, valine, isoleucine) and aromatic side chains (e.g., tyrosine, phenylalanine, tryptophan, histidine).

Alternatively or in addition to non-conservative amino acid residue substitutions, sequence alterations may lead to conservative amino acid substitutions. A 'conservative amino acid substitution' is one in which the amino acid residue is substituted for an amino acid residue having a similar side chain. Following mutagenesis, the encoded protein can be expressed and the activity of the protein can be determined as described below.

In one embodiment, the nucleic acid molecules are at least 70%, 75%, 80%, 85%, 90%, 95%, 97%, 98%, or 99% identical to any of the nucleic acid molecules of SEQ ID NOs: 41, 42, 50, 51 or 52.

In one embodiment, the nucleic acid molecules are the nucleic acid molecules of SEQ ID NOs: 41, 42, 50, 51 or 52.

In one embodiment the nucleic acid molecule comprises SEQ ID NO: 51.

In another embodiment, the nucleic acid molecules encode a polypeptide that has at least one function of RCA (e.g., Rubisco activation) and are at least 100, 250, 500, 750, 1000 or 1250 contiguous nucleotides in length.

In one embodiment, a nucleic acid molecule of the invention corresponds to a nucleic acid molecule that encodes a functional domain of RCA for example the ATP binding domain and the Rubisco binding domain.

The invention also provides nucleic acid molecules, chimeric genes and vectors comprising nucleic acid molecules of the invention.

The invention further provides cells, preferably plant cells, comprising a nucleic acid of the present invention.

Thermostable Complexes Comprising RCA

The present invention provides thermostable complexes comprising RCA and Rubisco. As used herein, the term 'improved thermostability' refers to the increased ability of a complex comprising RCA of the invention and Rubisco to function under heat stress conditions as compared to a complex comprising O. sativa RCA and Rubisco. In one embodiment complexes comprising RCA polypeptides of the invention have enzymatic activity under heat stress conditions (e.g. 35° C. or higher) that is greater than the enzymatic activity of complexes comprising O. sativa under the same conditions. In another embodiment, complexes comprising RCA polypeptides of the invention have enzymatic activity under heat stress conditions (about 28° C. to about 30° C., or about 30° C. to about 32° C., or about 32° C. to about 34° C., or about 34° C. or about 36° C., or about 34° C. to about 36° C., or about 36° C. to about 38° C., or to about 38° C. to about 40° C., or about 40° C. or higher) that is substantially similar to or higher than the activity of complexes comprising O. sativa RCA under the same conditions.

In one embodiment the invention provides a thermostable complex comprising an isolated RCA from a first plant species and an isolated Rubisco from a second plant species. For example the complex may comprise an isolated RCA from O. australiensis and an isolated Rubisco from O. sativa. For example the complex may comprise an isolated RCA from one Oryza sp. and an isolated Rubisco from another Oryza sp. It is envisaged that the RCA polypeptides of the invention can be used to form complexes with Rubisco from any plant species, such as other monocot species. In some embodiments the Rubisco in the complex is from barley, maize, tomato, potato, rice, soybean, cotton, sunflower, alfalfa, lettuce, oilseed rape, sorghum, or wheat plants. In particular embodiments the Rubisco in the complex is from barley, sorghum, rice or wheat.

The complexes may be formed in vitro or in vivo. For example the complexes may be formed in vitro by contacting recombinant O. australiensis RCA with Rubisco from O. sativa present in a leaf extract or Rubisco that has been purified from O. sativa. Alternatively, the complexes may be formed in vivo by expression of an RCA polypeptide of the invention in a plant such that it forms a complex with the endogenous Rubisco of the plant.

Any method known in the art can be used to assay the activity of complexes comprising RCA polypeptides (including, but not limited to, Rubisco activation and ATP hydrolysis).

In some embodiments, complexes comprising RCA polypeptides are assayed in vitro. In one embodiment, the complexes, either assembled from isolated components (e.g. those generated by recombinant expression) or complexes purified or extracted from for example, leaf tissue, can be assayed for activation of Rubisco when incubated in a solution comprising deactivated Rubisco, RuBP, ATP, and a source of labeled carbon (e.g., [$^{14}$C]NaHCO$_3$). In this embodiment incorporation of $^{14}$C into 3-phosphoglyceric acid can be monitored to assess Rubisco activation. In another embodiment, RCA polypeptides can be assayed for ATP hydrolysis when incubated in a solution comprising ATP. The assays are typically conducted at various temperatures ranging from normal conditions to heat stress conditions.

In other embodiments, complexes comprising RCA polypeptides are assayed in vivo. Plants which express one or more RCA polypeptides of the invention can be assayed for photosynthesis rate, rate of biomass increase, growth rates, and seed yield under heat stress conditions and compared with plants that express a wild type RCA. The plants may be grown entirely under heat stress conditions or for periods of time under heat stress conditions. In some embodiment heat stress conditions are determined at the leaf surface. Assays for photosynthesis rate, rate of biomass increase, growth rates, and seed yield are known in the art. For example, photosynthesis rates can be measured by analyzing CO$_2$ fixation. Growth rates may be assessed by measuring the increase in leaf area over time. Seed yield may be assessed by determining seed number and/or seed weight.

Methods of Enhancing Heat Tolerance in Plants

RCA activates Rubisco in plants and is the rate limiting step especially in heat stress conditions of the photosynthetic process (Salvucci, M. E. & Crafts-Brandner, S. J. (2004) Physiol. Plant. 120, 179-186). In the absence of RCA activity, Rubisco remains inactive and photosynthesis slows or stops. The present inventors have shown that complexes comprising RCA and Rubisco lose activity at high temperatures thereby suggesting that increased temperatures destabilize and/or denature complexes comprising RCA and Rubisco thereby rendering RCA less able or unable to activate Rubisco. Thus the heat tolerance of plants can be increased by the use of complexes comprising RCA polypeptides of the present invention. In particular RCA polypeptides of the invention can be expressed in plants.

Any method known in the art can be used to express at least one RCA polypeptide in a plant. For example, transgenic plants can be made to express one or more RCA polypeptides in all tissues or in a subset of tissues, preferably those tissues or organelles involved in photosynthesis. An RCA polypeptide may be expressed constitutively or be under the control of an inducible promoter, such as a heat inducible or chemical inducible promoter. In some embodiments, the expression and/or activity of the endogenous RCA of the plant may be reduced or eliminated.

Recombinant Expression

Nucleic acid molecules and polypeptides of the invention can be expressed recombinantly using standard recombinant DNA and molecular cloning techniques that are well known in the art (e.g., Sambrook, Fritsch, and Maniatis, Molecular Cloning: A Laboratory Manual; Cold Spring Harbor Laboratory Press: Cold Spring Harbor, (1989)). Additionally, recombinant DNA techniques known in the art may be used to create nucleic acid constructs suitable for use in making transgenic plants.

The invention also provides chimeric genes or nucleic acids expressing chimeric proteins or polypeptides, comprising a nucleic acid molecule of the invention, or a variant thereof. The term 'chimeric gene' refers to a nucleic acid molecule formed through the combination of portions of one or more nucleic acids of different origin. A chimeric gene is an artificial gene constructed by operably linking fragments of unrelated genes or other nucleic acid sequences. In other words "chimeric gene" denotes a gene which is not normally found in a plant species, i.e. it is heterologous with respect to the plant in which it is introduced, or refers to any gene in which the promoter or one or more other regulatory regions of the gene are not associated in nature with a part or all of the transcribed nucleic acid, i.e. are heterologous with respect to the transcribed nucleic acid. More particularly, a chimeric gene is an artificial, i.e. non-naturally occurring, gene produced by an operable linkage of a nucleic acid sequence to be transcribed.

The invention also provides vectors, preferably expression vectors, comprising a nucleic acid molecule of the invention, or a variant thereof. The term 'vector' refers to a polynucleotide capable of being used to maintain another nucleic acid to which it has been linked. For example a typical vector is a plasmid or a virus.

The invention provides recombinant expression vectors and chimeric genes or nucleic acid molecules that comprise a nucleic acid molecule encoding an RCA polypeptide of the invention in a form suitable for expression in a host cell. It will be understood by a skilled person that the choice of components of the chimeric gene and expression vector will depend on such factors as the host cell to be transformed, the level of expression of polypeptide desired, the tissue within the organism in which expression is desired, etc. Typically, recombinant expression vectors or chimeric genes can be introduced into host cells to produce proteins or peptides, including fusion proteins or peptides.

The recombinant expression vectors or chimeric genes or nucleic acid molecules can be for expression of an RCA polypeptide in prokaryotic (e.g. bacteria or yeast) or eukaryotic cells (e.g. insect, mammalian or plant cells). Alternatively, the recombinant expression vectors can be transcribed and translated in vitro, for example using T7 promoter regulatory sequences and T7 polymerase.

In some embodiments, a nucleic acid molecule of the invention can be expressed in plant cells using a recombinant expression vector or chimeric gene or nucleic acid molecule designed for use in plants, for example, tobacco mosaic virus and potato virus expression vectors or any other plant expression vector known in the art.

A number of promoters known in the art can be used to express the nucleic acids of the invention for example the promoters may be constitutive, tissue-specific or inducible.

A 'tissue-specific promoter' may direct expression of nucleic acids of the present invention in a specific tissue, organ or cell type. A tissue-specific promoter may also be an inducible promoter. Alternatively a 'constitutive promoter' is defined as a promoter which will direct expression of a gene in all tissues and are active under most environmental conditions and states of development or cell differentiation.

The term 'inducible promoter' refers to a promoter that is under precise environmental or developmental control. In particular embodiments the inducible promoter may be a chemically-inducible promoter or a heat-inducible promoter or a light-inducible promoter. Examples of chemically-inducible promoters in plants include promoters which are inducible upon exposure to chemical reagents which can be applied to the plant, such as herbicides or antibiotics. For example, the maize In2-2 promoter, activated by benzenesulfonamide herbicide safeners, can be used (De Veylder (1997) Plant Cell Physiol. 38:568-577); application of different herbicide safeners induces distinct gene expression patterns, including expression in the root, hydathodes, and the shoot apical meristem. Coding sequence can be under the control of, e.g., a tetracycline-inducible promoter, e.g., as described with transgenic tobacco plants containing the *Avena sativa* L. (oat) arginine decarboxylase gene (Masgrau (1997) Plant J. 11:465-473); or, a salicylic acid-responsive element (Stange (1997) Plant J. 11:1315-1324). Using chemically (e.g. hormone or pesticide)-induced promoters, i.e., promoters responsive to a chemical which can be applied to the transgenic plant in the field, expression of a polypeptide of the invention can be induced at a particular stage of development of the plant. Use may also be made of the estrogen-inducible expression system as described in U.S. Pat. No. 6,784,340 and Zuo et al. (2000, Plant J. 24: 265-273) to drive the expression of the nucleic acids used to practice the invention.

Examples of heat-inducible promoters in plants include the heat shock promoters for example the promoter of Hsp90p or other heat-inducible promoters such as those for genes OsHsfB2cp and PM19p.

Examples of light-inducible promoters include e.g. green-tissue promoters like the pea rbcS-3A promoter (Kuhlemeier et al. (1989) Plant Cell 1: 471-478), and the maize rbcS promoter (Schaffher and Sheen (1991) Plant Cell 3: 997-1012).

One aspect of the invention pertains to host cells into which a nucleic acid encoding an RCA polypeptide of the invention has been introduced. Introduction of the nucleic acid into the cell can be by any means known in the art, for example using microinjection; *Agrobacterium*-mediated transformation; direct gene transfer; ballistic particle acceleration; virus-mediated transformation; chloroplast transformation or electroporation. The term 'host cell' refers to the particular subject cell and to the progeny or potential progeny of such a cell. Modifications may occur in subsequent generations of a host cell for example due to either mutation or environmental influences, and thus the subsequent generations may not, in fact, be identical to the original host cell, but are still included within the scope of the term as used herein.

In other embodiments a nucleic acid of the invention may be introduced into a plant or plant cell by crossing a plant containing the nucleic acid with another plant that doesn't contain the nucleic acid so that at least some of the progeny of the crossing contain the nucleic acid.

Accordingly, the invention provides plants and plant cells comprising a nucleic acid of the invention.

Production of Plants

The RCA polypeptides and nucleic acids of the invention may be useful for producing transgenic plants. Any method known in the art can be used for transforming a plant or plant cell with a nucleic acid molecule of the present invention. Nucleic acid molecules can be incorporated into plant DNA (e.g., genomic DNA or chloroplast DNA) or be maintained without insertion into the plant DNA (e.g., through the use of artificial chromosomes). Suitable methods of introducing nucleic acid molecules into plant cells include microinjection; *Agrobacterium*-mediated transformation; direct gene transfer; ballistic particle acceleration; virus-mediated transformation; chloroplast transformation; and electroporation. The choice of transformation method used will vary depending on the type of plant or plant cell (e.g. monocot or dicot) to be transformed.

Transformed plant cells which are derived by any of the above transformation techniques can be cultured to regenerate a whole plant which possesses the transformed genotype and thus the desired phenotype. Such regeneration techniques rely on manipulation of certain phytohormones in a tissue culture growth medium, typically relying on a biocide and/or herbicide marker that has been introduced together with the desired nucleotide sequences. Plant regeneration from cultured protoplasts is described in the art. Regeneration can also be achieved from plant callus, explants, organs, or parts thereof. Regeneration techniques are also known in the art.

In some embodiments the plant cells of the invention are non-propagating plant cells.

Plants comprising RCA polypeptides and nucleic acids of the invention may be produced by crossing a plant containing the nucleic acid with another plant that doesn't contain the nucleic acid so that at least some of the progeny of the crossing contain the nucleic acid.

As used herein the term 'plant' refers to whole plants, shoot vegetative organs/structures (e.g. leaves and stems), roots, flowers and floral organs/structures (e.g. bracts, sepals, petals, stamens, carpels, anthers and ovules), seed (including embryo, endosperm, and seed coat) and fruit (the mature ovary), plant tissue (e.g. vascular tissue, ground tissue, and the like) and cells (e.g. guard cells). The term 'plant' also refers to higher and lower plants amenable to transformation techniques, including angiosperms (monocotyledonous and dicotyledonous plants), gymnosperms, ferns, and multicellular algae. Plants of a variety of ploidy levels, including aneuploid, polyploid, diploid, haploid and hemizygous plants are also included.

The nucleic acid molecules of the invention can be used to express an RCA polypeptides of the invention in any plant, including species from the genera *Agrotis, Allium, Ananas, Anacardium, Apium, Arachis, Asparagus, Athamantha, Atropa, Avena, Bambusa, Beta, Brassica, Bromus, Browaalia, Camellia, Cannabis, Carica, Ceratonia. Cicer, Chenopodium, Chicorium, Citrus, Citrullus, Capsicum, Carthamus, Cocos, Coffea, Coix, Cucumis, Cucurbita, Cynodon, Dactylis, Datura, Daucus, Dianthus, Digitalis, Dioscorea, Elaeis, Eliusine, Euphorbia, Festuca, Ficus, Fragaria, Geranium, Glycine, Graminae, Gossypium, Helianthus, Heterocallis, Hevea, Hibiscus, Hordeum, Hyoscyamus, Ipomoea, Lactuca, Lathyrus, Lens, Lilium, Linum, Lolium, Lotus, Lupinus, Lycopersicon, Macadamia, Macrophylla, Malus, Mangifera, Manihot, Majorana, Medicago, Musa, Narcissus, Nemesia, Nicotiana, Onobrychis, Olea, Olyreae, Oryza, Panicum, Panicum, Panieum, Pannisetum, Pennisetum, Petunia, Pelargonium, Persea, Pharoideae, Phaseolus, Phleum, Picea, Poa, Pinus, Pistachia, Pisum, Populus, Pseudotsuga, Pyrus, Prunus, Pseudotsuga, Psidium, Quercus, Ranunculus, Raphanus, Ribes, Ricinus, Rhododendron, Rosa, Saccharum, Salpiglossis, Secale, Senecio, Setaria, Sequoia, Sinapis, Solanum, Sorghum, Stenotaphrum, Theobromus, Trigonella, Trifolium, Trigonella, Triticum, Tsuga, Tulipa, Vicia, Vitis, Vigna,* and *Zea.*

In some embodiments the transgenic plants are barley, maize, tomato, potato, rice, soybean, cotton, sunflower, alfalfa, lettuce, oilseed rape, sorghum, or wheat plants. In particular embodiments the transgenic plants are monocots plants or cereal plants such as barley, sorghum, rice, corn or wheat. A skilled person will recognize that after production of a transgenic plant, the nucleic acid molecule of the invention in that transgenic plant can be introduced into other plants by sexual crossing. Any standard breeding technique known in the art can be used to achieve this.

Determination of Expression in Plants

Any method known in the art can be used for determining the presence or level of expression in a plant of a nucleic acid molecule of the invention or an RCA polypeptide of the invention. For example, the expression level in a plant of a RCA polypeptide can be assessed using molecular techniques including, for example, immunoassay, immunoprecipitation, gel electrophoresis, and mass spectrometry.

Additionally, the expression of an RCA polypeptide in a plant can be assessed by a change in the plant phenotype (for example photosynthesis rate, growth rate or seed yield) under heat stress conditions compared with plants expressing wild type RCA.

Furthermore, extracts or polypeptides isolated from transgenic plants, their tissues cells or seeds can be used in in vitro assays.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

EXAMPLES

Example 1: DNA Sequencing and Sequence Alignment

Initially total RNA was extracted from 100 mg of leaf tissue using an RNeasy Plant Mini Kit (Qiagen). RNA was converted to cDNA using a SuperScript VILO cDNA Synthesis Kit (Invitrogen) using 2.1 µg of RNA as a template. PCR was performed on 2 µl of the cDNA product using GoTaq Green Master Mix (Promega). Refer to Supplementary Methods in Scafaro, A. P., Haynes, P. A. & Atwell, B. J. (2010) J. Exp. Bot. 61, 191-202 for the PCR cycle program and the primers used. The product was run on a 1.5% agarose gel stained with Gel Red (Biotium). The bands where cut from the gel using a scalpel and the DNA purified using a DNA Gel Extraction Kit (Qiagen). The PCR products were sequenced in both directions using the same primers as PCR amplification. Sequence preparation was performed using Big Dye Terminator V3.1 sequencing reaction mix as per manufacturer's instructions and samples run on a 3130×1 Genetic Analyzer (Applied Biosystems, Foster City, Calif., USA). Multiple DNA and protein sequences were aligned using the MUSCLE algorithm [Edgar RC (2004) MUSCLE: multiple sequence alignment with high accuracy and high throughput. Nucleic Acids Research 32: 1792-1797] and the open-source software program Unipro UGENE v1.9.0.

Results: RCA and its Expression

The RCA genes of *Oryza sativa* L. ssp. *japonica* cv. Amaroo, the two *O. meridionalis* accessions and *O. aus-* traliensis were sequenced and differences were found between the species. There was no difference in sequence between the two O. meridionalis accessions. There were 50 base changes between O. australiensis and O. sativa including 44 base substitutions and six deletions in the O. australiensis gene. Three of the O. australiensis base substitutions not found in O. sativa were also found in O. meridionalis. Another four base changes were unique to O. meridionalis. When the DNA sequences were translated to amino acid sequence the DNA sequence differences between O. sativa and O. meridionalis did not translate into a difference in protein. There were however 18 residue changes/deletions unique to both RCA isoforms of O. australiensis (see Table 1$^a$). The protein sequence of O. australiensis was then compared with two warm-adapted species, Gossypium hirsutum (cotton) and Larrea tridentata (creosote bush), and the cold adapted species Spinacia oleracea (spinach) and Deschampsia antarctica (Antarctic hairgrass). Four of the residue differences found in O. australiensis was the same as one or both of the corresponding residues found in the warm-adapted species but not in either of the cold-adapted species (see Table 1$^b$).

Example 2: Superior Tolerance to Heat Stress in the Wild Rice Oryza australiensis Due to Thermostable RCA Materials and Methods
Plant Growth—Short-Term Heat Treatment (Reference FIGS. 1-3)

Seeds of Oryza sativa L. ssp. japonica cv. Amaroo (Os-A) and O. sativa L. ssp. indica cv. Doongara (Os-D) were obtained from the Yanco Agricultural Institute (Department of Primary Industries, NSW, Australia). Seeds of Oryza meridionalis Ng. were collected from wild populations located in the Cape York Peninsula of Australia at S15° 42', E145° 03' (henceforth referred to as O. meridionalis CY or Om-CY) and from Keep River north of Western Australia at S15° 58', E129° 03' (henceforth referred to as O. meridionalis KR or Om-KR). Oryza australiensis Domin. were collected from the same location as O. meridionalis KR. For all experiments, plants were grown in controlled growth cabinets (Thermoline Scientific Equipment, Smithfield, NSW, Australia) under a 12-h photoperiod with a photosynthetic photon flux density (PPFD) of 600 to 800 µmol m$^{-2}$ s$^{-1}$. Plants were grown at 28/22° C. (day/night) in a 3:1, soil of fine-textured krasnozem (locally sourced from Robertson, NSW, Australia) and an organic mix, in pots with no drainage holes. For leaf elongation rate experiments, plants were grown in 2-L pots and measurements were taken at the 5th-leaf stage. For all other experiments, plants were measured after growing for 60 days in 10-L pots. Soil was kept wet at all times and allowed to pool at the surface once the plants were over 40-days old. A commercial liquid fertilizer (Aquasol, Yates, Australia) was applied once a week following manufacturer's instructions, beginning 10 days after germination.

Figure 25:
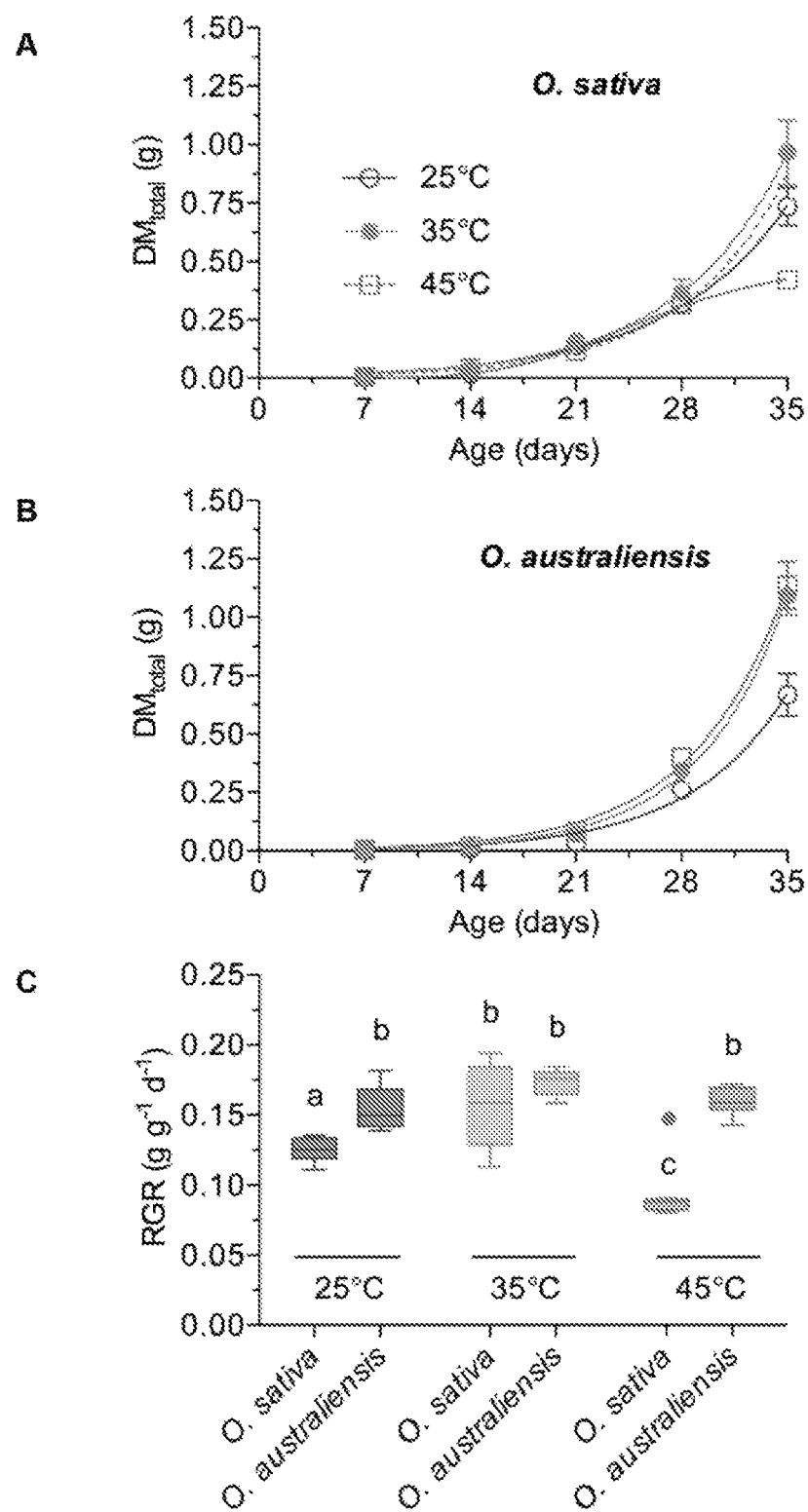
FIG. 25. Shows the dry mass increase during the first 35 days of seedling growth for *O. sativa* and *O. australiensis* at three day temperatures (25° C., 35° C. and 45° C.). Night temperatures were set at 21° C. Dry biomass was then used to calculate relative growth rates (RGR) the 7-35 day interval. RGR for *O. sativa* from 7-28 days at 45° C. is represented by the single dot, while the arrest of growth after 28 days suppressed RGR. Bars indicate standard errors of the mean, while box plots show means with ranges and Tukey numbers to indicate significant differences.
Figure 26:
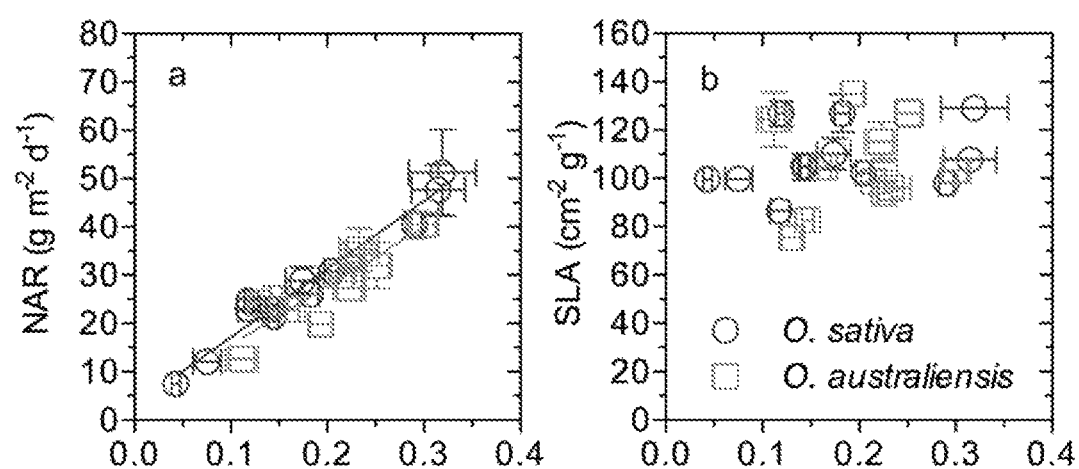
FIG. 26. Shows net assimilation rate (NAR) and specific leaf area (SLA) plotted against relative growth rate on a biomass basis (RGR) using observations from all temperatures (25, 35 and 45° C.) and two species (*O. sativa* and *O.*

Plant Growth—Long-Term Heat Treatment (Reference FIG. 25-26)

Seeds of Oryza sativa L. ssp. japonica cv. Amaroo (Os-A) and Oryza australiensis Domin. were grown as described above and 7 days after germination, seedlings were exposed to three temperatures (25, 35 and 45° C.) during the day (12 h) and 21 degrees at night until plants were 35 days old. Seedlings were harvested weekly by measuring leaf area, and fresh and dry biomass for shoots and roots. Relative growth rates and net assimilation rates were calculated using dry mass and leaf area for the treatment period (7-35 d after germination).

Leaf Elongation Rates

Leaf elongation rates were measured using a HR4000 Linear Variable Displacement Transducer (LVDT). After emergence of the fifth leaf, plants were transferred to a cabinet containing the LVDT unit and randomly assigned to one of the eight measurement stations. The fifth leaf was clipped to the apparatus and growth was measured for a 24-h period. Plants were grown at 22° C. for the initial 12 h of growth in the dark followed by 28° C. for the first 4 h of the light period. The cabinet temperature was then raised to 45° C. for 4 h and returned to 28° C. for the final 4 h of the day period. Leaf length was measured and logged every 6 mins using the software program VuGrowth, version 1.0 (Applied Measurement, Oakleigh, Victoria, Australia). The ambient temperature of the cabinet was logged ever 10 min by a portable data logger (Onset HOBO, Massachusetts, USA) placed next to the plants. Leaf lengths were converted to leaf elongation rate (LER) by subtracting the leaf length at any given time by the leaf length 1 h prior to that measurement. The experiment was repeated on six occasions with nine plants from each genotype measured in total.

Gas-Exchange and Rubisco Activation State Assays

Gas-exchanges were measured using a Licor 6400 (LI-COR, Lincoln, USA). The $CO_2$ in the reference chamber air was set at 380 ppm and a PPFD of 1500 µmol m$^{-2}$ s$^{-1}$ was used for all measurements. Measurements were made in the growth cabinet and the air temperature of the gas exchange cuvette was set to 28 or 45° C. to match the cabinet temperature. Control measurements were made at 28° C. beginning 2 h into the light period. Measurements at 45° C. commenced after 2 h of exposure to 45° C. and continued over a 2 h period by randomly measuring the different genotypes over that 2 h period. All measurements were made on healthy, fully-expanded leaves. Measurements were made on 3-6 leaves from 3 pot replicates. To determine the activation state of Rubisco, two 0.266 cm$^2$ leaf disks were rapidly excised from mature fully-expanded leaves using a leaf punch and immediately frozen in liquid nitrogen. The Rubisco activation state was calculated by measuring total and initial Rubisco activities. Samples were collected throughout the light period to coincide with growth measurements. Samples were collected after 2 h at 28° C. (2 h light), 2 h at 45° C. (4 h light), 4 h at 45° C. (6 h light) and again at 28° C. after 1 h of recovery from the higher temperatures (7 h light). Four replicates were collected from separate pots placed randomly throughout the cabinet.

Immunoblot Analysis

For immunoblot analysis, plant material was harvested at a cabinet temperature of 28° C. or after 2 h at 45° C. as described above for Rubisco activation. Plant material was ground in liquid nitrogen and 100 mg of fine tissue was weighed before extraction by vortexing in 800 µl of SDS extraction buffer containing 30% sucrose, 2% SDS, 0.1 M Tris-HCl, pH 8.0, 5% β-mercaptoethanol. Samples were centrifuged at 10,000 g for 5 min and 10 µl of the supernatant was added to 3 µl of 5×SDS-loading dye (Invitrogen). Samples were electrophoresed in NuPage BIS-TRIS 6-12% gradient SDS-PAGE gels (Invitrogen) together with pre-stained molecular weight markers (Precision Plus All Blue Standard, Bio-Rad, city, country). Polypeptides were transferred to polyvinylidene difluoride (PVDF) membranes for immunological detection of RCA using an anti-tobacco activase primary antibody (Law, D., Crafts-Brandner, S. & Salvucci, M. (2001) Planta 214, 117-125.) in conjunction with an alkaline phosphatase-conjugated goat anti-rabbit secondary antibody (Sigma Aldrich). Immunoblots were stained with NBT/BCIP (Promega). Immunoblot analyses were conducted in triplicate, i.e., using samples prepared from three different plants. RCA primary antibody used in western blot analysis has a greater affinity for RCA-Oa than RCA-Os. Taking into consideration the difference in antibody reactivity through a standard curve generated from purified recombinant RCA of known concentration, the concentration of RCA in the leaf was obtained.

Statistics

All graphs and statistics were created using GraphPad Prism 5.0d software (GraphPad Prism Software Inc., San Diego, USA). For both LER and Rubisco activation state data, a two-way ANOVA was run initially. When appropriate, this test was followed by individual one-way ANOVA and Tukey's multiple comparison tests. Gas-exchange data was analysed with a two-sample t-test between control and heat treatment for each genotype independently.

Results

Temperature-Dependent Growth and Photosynthesis

Figure 1:
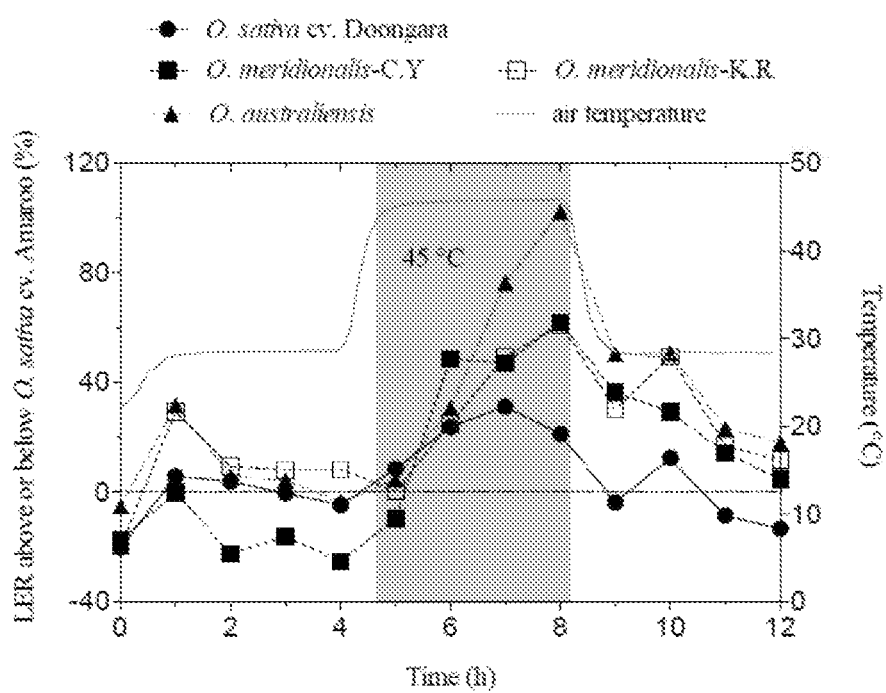
FIG. 1. Effect of high temperature on the leaf elongation rate (LER) of rice genotypes. Elongation rates were measured over a 12-h period for *O. sativa* cv. Doongara (closed circles), *O. meridionalis*-CY (closed squares) and *O. meridionalis*-KR (open squares) and *O. australiensis* (closed triangles). Values are expressed as a percentage of the leaf elongation rate (LER) of *O. sativa* cv. Amaroo, measured over the same period. After 4 h at 28° C., the temperature was increased to 45° C., maintained for 4 h, and then reduced to 28° C., as indicated by the shaded (45° C.) area. Measurements of leaf length commenced 1 h prior to the beginning and ended at the end of the 12-h photoperiod. The solid grey line is the ambient temperature of the cabinet. Values are the mean of six experimental replicates. For clarity error bars have been omitted.

The relative heat sensitivity of four genotypes was determined by comparing their LER to the LER of Os-A (FIG. 1). The comparison showed that the LERs of all genotypes were similar to that of Os-A at 28° C., but at 45° C. the rates were comparatively higher, exhibiting species-specific differences in the response to high temperature. As the temperature was lowered to 28° C., LER was again similar amongst all the genotypes, including Os-A. Rates of leaf elongation were similar for all of the rice genotypes after a 1-h exposure to 45° C. However, by the end of a 4-h heat exposure period, differences in the growth rates between Os-A and the four other genotypes were obvious. O. sativa cv. Doongara (Os-D) was more tolerant than Os-A, but less tolerant than the wild rice genotypes. The two O. meridionalis populations (Om-CY and Om-KR) had a similar response and their heat tolerance was intermediate between Os-D and O. australiensis. Oryza australiensis showed the greatest tolerance to high temperature; after 4-h of exposure to 45° C. its LER was double that of Os-A.

Figure 2:
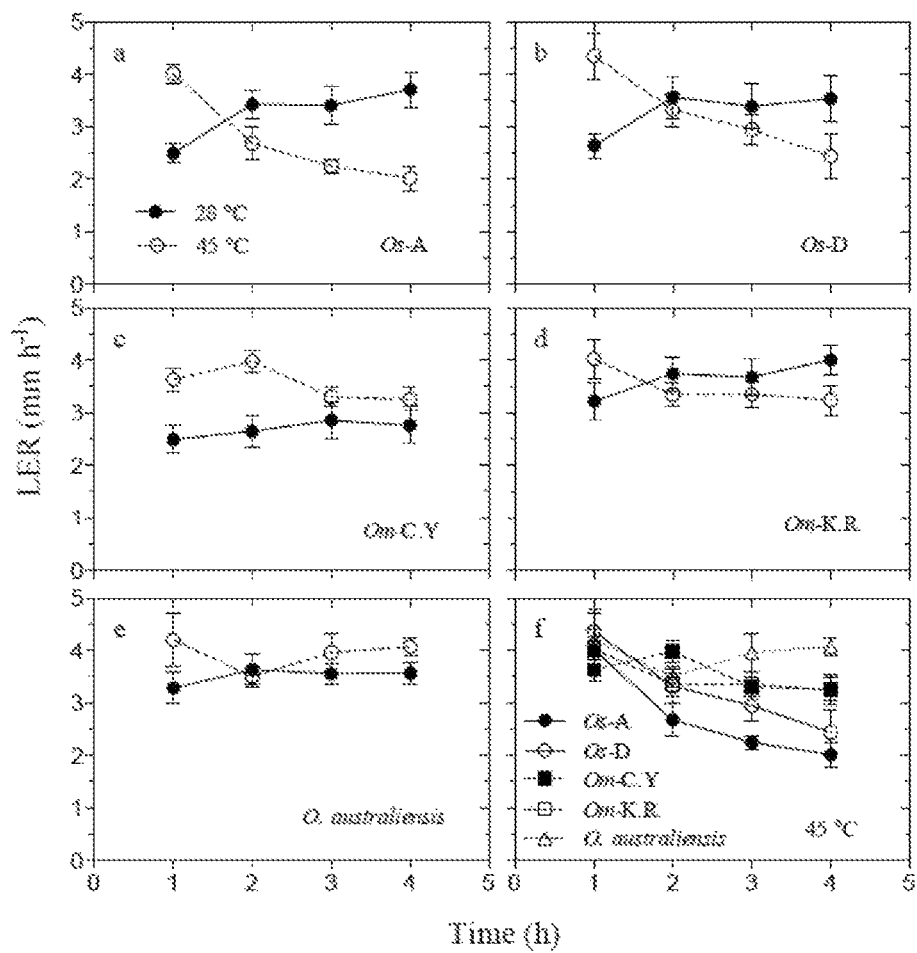
FIG. 2. Leaf elongation rate (LER) of five rice genotypes over 4 h at 28 or 45° C. LER was measured at either 28° C. (filled circles/solid line) or 45° C. (open circles/dashed line) over a 4-h period for *O. sativa* cv. Amaroo (Os-A) (a); *O. sativa* cv. Doongara (b); *O. meridionalis*-CY (Om-CY) (c); *O. meridionalis*-KR (Om-KR) (d); and *O. australiensis* (e). In panel f, the LER at 45° C. of all five genotypes are plotted together. Values are means±SE (n=6).

A significant interaction between the effects of growth temperature and exposure time on LER was observed for all the genotypes, except for O. australiensis (Table 8). This interaction was evident by the relatively stable growth rates at 28° C. compared with reduced rates at 45° C. (FIG. 2). Oryza australiensis was unique among the genotypes in maintaining a similar LER at 28 and 45° C. (FIG. 2, panel (e)). Because of the lack of growth inhibition at 45° C., there were no significant differences in the LER between the two temperatures or over the exposure period for O. australiensis. When comparing the LER over the 4-h exposure period at 45° C., all five genotypes exhibited the highest rates at the lowest exposure time (1-h). For both O. sativa cultivars, the LER continuously and markedly decreased over the 4-h exposure time (FIG. 2, panels (a) and (b)). A more moderate decrease in LER occurred in the two O. meridionalis populations (Figure panels 2(c) and (d)), whereas the LER of O. australiensis was not significantly affected over the 4-h period of exposure to 45° C.

TABLE 8

Results of a two-way ANOVA for the data shown in FIG. 2 with P-values given for comparisons between the two growth temperatures, the exposure time at each temperature and the interaction between the two variables.

| | P-values | | |
| Genotype | Temperature | Exposure time | Interaction |
| --- | --- | --- | --- |
| O. sativa cv. Amaroo | 0.1477 | 0.0197 | <0.001 |
| O. sativa cv. Doongara | 0.9734 | 0.0050 | <0.001 |
| O. meridionalis CY | 0.0382 | 0.0277 | <0.001 |
| O. meridionalis KR | 0.6711 | 0.8775 | <0.001 |
| O. australiensis | 0.2373 | 0.6785 | 0.1331 |

Plants were grown at an ambient temperature of either 28 or 45° C. for an exposure time of 4 h and leaf lengths measured every 6 min using an LVDT (refer to FIG. 1). All statistics were based on six experimental replicates.

Heat applied to plants during daylight hours for four weeks was used to test whether the heat tolerance effects seen for leaf elongation in O. australiensis could be replicated over longer periods (FIG. 25). Two main effects were observed: (1) O. australiensis grew as fast at 45° C. as at 35° C. and (2) growth in O. sativa slowed dramatically after three weeks of heat treatment. Relative growth rates reflected this, with O. australiensis shoots about one-third the biomass of those of O. sativa by the end of the heat treatment. FIG. 26 shows the correlation between relative growth rate and net assimilation rate/specific leaf area, the two determinants of relative growth rate. This illustrates that net assimilation rate is the driving variable for growth across six temperature×genotype combinations. This is turn suggests that metabolism and photosynthesis/respiration are the key drivers of growth, not leaf construction.

Figure 3:
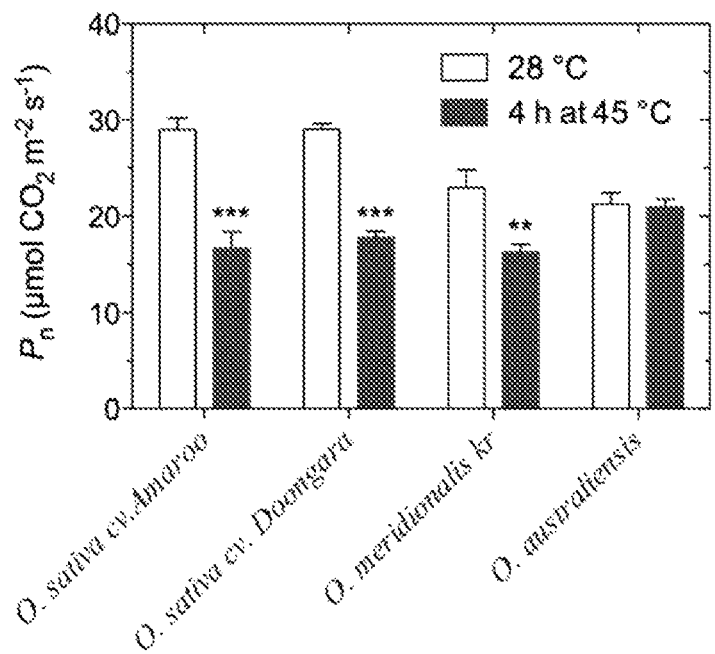
FIG. 3. The effect of elevated temperature on gas-exchange ain five rice genotypes as annotated in FIG. 1. Net photosynthetic rate ($P_n$) was measured at 28° C. (open bars) or at 45° C. (closed bars). Plants were exposed to 45° C. for 2 to 4 h prior to measurement. Temperature-dependent differences in parameters for each genotype were determined using a two-sampled t-test. * indicates significance at P<0.05,  indicates significance at P<0.01 and * indicates significance at P<0.001. Values are means±SE of three pot replicates.

The effect of elevated temperature on net photosynthetic rate ($P_n$) was also species-specific. Net photosynthesis decreased after 2-4 h at 45° C. for all the genotypes, except O. australiensis (FIG. 3). The decrease in $P_n$ was more marked for O. sativa (42% for Os-A and 39% for Os-D), intermediate for O. meridionalis (25% for Om-CY and 29% for Om-KR) and minimal for O. australiensis (1%).

Rubisco Activation State

The response of Rubisco activation state to increased temperature (Table 9) was similar to the response observed for LER and $P_n$ in the five genotypes (FIGS. 2 and 3). Upon exposure to 45° C., Rubisco activation decreased the most in the two O. sativa cultivars, compared with a more moderate decrease in the two O. meridionalis populations and a minimal decrease in O. australiensis. For all five genotypes, there was an initial decrease in the activation state of Rubisco after 2 h at 45° C. Interestingly, the decrease in Rubisco activation that occurred after a 2-h exposure to 45° C. was lowest in the two genotypes from the hottest environment, i.e., Keep River. When the exposure to heat was extended to 4 h, Rubisco activation either remained at the same lower level (Os-A and Om-KR & -CY) or decreased further (Os-D) except in O. australiensis. In O. australiensis, Rubisco activation recovered during the extended exposure to 45° C. and when a 1-h recovery period at 28° C. followed the 4-h heat exposure, achieving an activation state comparable to the initial activation state at 28° C. In contrast, the activation state of Rubisco in the other two species remained inhibited even after a 1-h recovery period at 28° C.

To determine whether there was a significant difference in the response of Rubisco activation state to exposure time at high temperature among the various genotypes, a two-way analysis of variance was performed. The analysis indicated that there was no significant genotype×exposure time interaction (F=0.9516, P=0.5037, df=12). One-way ANOVA revealed significant differences (P=0.0016) between species only after exposure of the plants for 4 h at 45° C., when the activation state of Os-A was lower than O. australiensis and the activation state of Os-D was lower than both Om-KR and O. australiensis (Table 8). There were no significant differences (P>0.05) in activation state between the O. meridionalis and O. australiensis genotypes. Moreover, there was no significant effect (P>0.05) of the elevated temperature on the activation state for these three genotypes. Conversely, both O. sativa cultivars exhibited a significant decrease (P=0.0032 for Os-A and P=0.002 for Os-D) in activation state after a 4-h exposure to 45° C. compared with the activation state at 28° C.

Domesticated rice, O. sativa, was the most susceptible to inhibition by heat, whereas the wild rice O. meridionalis was less susceptible and O. australiensis exhibited tolerance to heat stress. The variation in tolerance among the species was related to the level of photosynthetic inhibition at the elevated temperature, which in turn was related to the degree to which Rubisco deactivated. Heat-tolerant O. australiensis exhibited no reduction in growth, photosynthesis or Rubisco activation when exposed to 45° C. for over 2 h. To account for the differences in thermotolerance, we propose that differences in the structure of activase between O. australiensis and the other two species, coupled with a potentially greater abundance of the protein, ameliorate the thermotolerance of Rubisco activation in O. australiensis with a consequent effect on photosynthesis and growth.

TABLE 9

Rubisco activation state (%) of five rice genotypes in response to changes in ambient temperature.

| Temperature | O. sativa | | O. meridionalis | | | |
|---|---|---|---|---|---|---|
| | cv. Amaroo | cv. Doongara | CY | KR | O. australiensis | P-value |
| 28° C. | 64 ± 1 | 70 ± 8 | 72 ± 2 | 68 ± 5 | 68 ± 7 | 0.8540 |
| 2 h at 45° C. | 44 ± 5 | 47 ± 9 | 47 ± 4 | 55 ± 6 | 54 ± 9 | 0.7453 |
| 4 h at 45° C. | 42 ± 6 | 27 ± 3 | 46 ± 7 | 53 ± 6 | 67 ± 4 | 0.0016 |
| 28° C. recovery | 29 ± 3 | 30 ± 2 | 46 ± 12 | 44 ± 8 | 66 ± 14 | 0.0670 |
| P-value | 0.0032 | 0.0022 | 0.1439 | 0.1761 | 0.6866 | |

A one-way ANOVA was used to determine differences between genotypes at a single growth condition and another one-way ANOVA for differences within a genotype across all growth conditions. Plants were analysed before (28° C.), during the heat treatment (2 h at 45° C. and 4 h at 45° C.) and also after a recovery period of 1 h at 28° C. (28° C. recovery). All values are means ± SE (n = 4).

Figure 4:
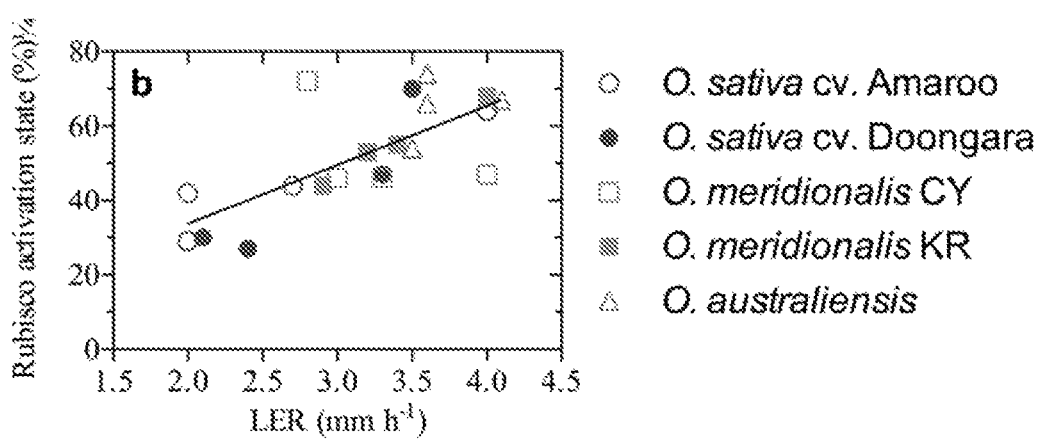
FIG. 4. The relationship between leaf elongation rate (LER) and Rubisco activation state in five rice genotypes (*O. sativa* cvs Amaroo and Doongara; *O. meridionalis* CY and KR; *O. australiensis*) at 28 and 45° C. The mean LER for each genotype at each growth condition was plotted against the corresponding activation state and a linear regression analysis was performed (solid line, y=0.033x+1.45, P=0.0004, $r^2$=0.5106).

The similarity in the temperature response of LER and Rubisco activation state for each genotype led to the determination of a positive relationship between the two variables (FIG. 4). Linear regression analysis indicated that 51% of the change in LER could be explained by changes in Rubisco activation state.

RCA and its Expression

Sequencing of the RCA genes from O. sativa cv. Amaroo, the two O. meridionalis populations and O. australiensis revealed differences in RCA sequence between the three species, but not between the two O. meridionalis populations. There were 50 base differences between O. australiensis and O. sativa including 44 base substitutions and six deletions in the O. australiensis gene. Three of the base substitutions found in O. australiensis when compared to O. sativa were also found in O. meridionalis. In addition, another four base changes were unique to O. meridionalis. When the DNA sequences of the RCA genes were translated to protein sequences, the differences between O. sativa and O. meridionalis at the nucleotide level did not translate into differences at the amino acid level. In contrast, comparison of the amino acid sequences for RCA from the different genotypes revealed three residue deletions and 15 residue substitutions that were unique to O. australiensis, for both the small form and the large form.

For all five rice genotypes, the abundance of RCA protein was not affected by exposure to 45° C. for 2 h, nor was the ratio of the large to small form of RCA. Irrespective of temperature there was a similar total abundance of RCA between all genotypes.

CONCLUSIONS

Three rice species differed in their heat tolerance, as indicated by differences in vegetative growth at 45° C.

Example 3: In Planta Rubisco and RCA Stoichiometry

Rubisco and RCA concentration was determined by Western Blot analysis of extracted total soluble leaf protein calibrated against purified Rubisco and RCA of known concentration.

To determine in vivo concentrations of the two enzymes, standard curves were generated using purified enzyme of known concentration. The concentration of Rubisco was determined using an antibody specific for the 53 kDa large subunit of Rubisco. Because the quaternary structure of the Rubisco complex comprises 8 large and 8 small (16 kDa) subunits, the total Rubisco content could be deduced from these westerns. Table 4 lists the concentrations of Rubisco and RCA for the two species and the ratio between the two functionally complete enzymes. While there was substantial variation between biological and technical replicates using this indirect method, there was no evidence for statistically differences between the species. However, in the absence of a more precise technique that is relatively simple, we believe that these concentrations are credible. Despite some variation, the in vivo enzyme concentrations we report in Table 10 match the concentrations found after protein purification (i.e. concentrations achieved when extracting RCA and Rubisco from leaves). Considering the concentration of Rubisco and RCA were determined from the same tissue samples we can be relatively confident in the comparative ratios of the two proteins across species. However differences in the absolute concentration of Rubisco and RCA between the species may be affected by differences in growing conditions between harvests, particularly nitrogen availability, which is influenced by life-stage.

TABLE 10

Rubisco and RCA in vivo concentrations

| | Rubisco | | RCA | | Rubisco:RCA | |
|---|---|---|---|---|---|---|
| | (mg · g⁻¹) | | (mg · g¹) | | | |
| | FW#) | (uM*) | FW) | (µM) | (g:g) | (M:M) |
| O. sativa | 5.7 ± 1.2 | 10.3 ± 2.2 | 1.3 ± 0.6 | 5.9 ± 2.7 | 4.4:1 | 1.7:1 |
| O. australiensis | 6.8 ± 2.2 | 12.3 ± 4.0 | 1.8 ± 0.5 | 8.2 ± 2.3 | 3.8:1 | 1.5:1 |

Milligrams of protein per gram of leaf fresh weight, based on Western blot analysis.
*The molarity is based on the functional Rubisco enzyme molecular weight being 553,000 Da and the RCA oligomer with most activity having a molecular weight of 220,000 Da based on native gel analysis (presented in Example 4). One gram of fresh weight is assumed to equate to 1 mL of volume. Both *O. sativa* and *O. australiensis* were grown at 28° C.

Example 4: RCA Concentration-Dependent Oligomer Formation (Native Gels)

Native gel analysis has allowed for the concentration-dependent self-oligomerisation of RCA subunits to be observed. To the inventors' knowledge this is the first time native gels have been used to visualise the interaction of RCA subunits. Others have shown similar RCA self-assembly in cotton and tobacco using fluorescence and small angle X-ray scattering techniques (Henderson, J. N., Hazra, S., Dunkle, A. M., Salvucci, M. E. & Wachter, R. M. (2013) Biochimica et Biophysica Acta (BBA)—Proteins and Proteomics 1834, 87-97; Wachter, R. et al. (2013) Photosynthesis Res. 117, 557-566.). Similarly, *O. australiensis* (Oa) and *O. sativa* (Os) RCA form a larger complex through self-association when the enzyme concentration is increased. The inhibition of activation activity at low RCA concentrations is a result of the self-associating complex falling below a certain threshold of about three RCA subunits. Note that due to differences in protein isoelectric points and protein physical shape, native bands may migrate ±15% from what is expected based on molecular weight alone.

Rather than being distinct in size, increasing concentration of RCA led to a range of RCA oligomer sizes, shifting from lower to higher molecular weights as the concentration increased. With increasing concentration, the beta isoform seems to form at least three distinct oligomer molecular weights while the alpha isoform is found as mostly a single oligomer that shifts to higher molecular weights with increased RCA concentration.

Although there was distinct RCA complex and Rubisco complex bands on native gels there was no discernible Rubisco/RCA complex when the two enzymes were mixed.

Figure 21:
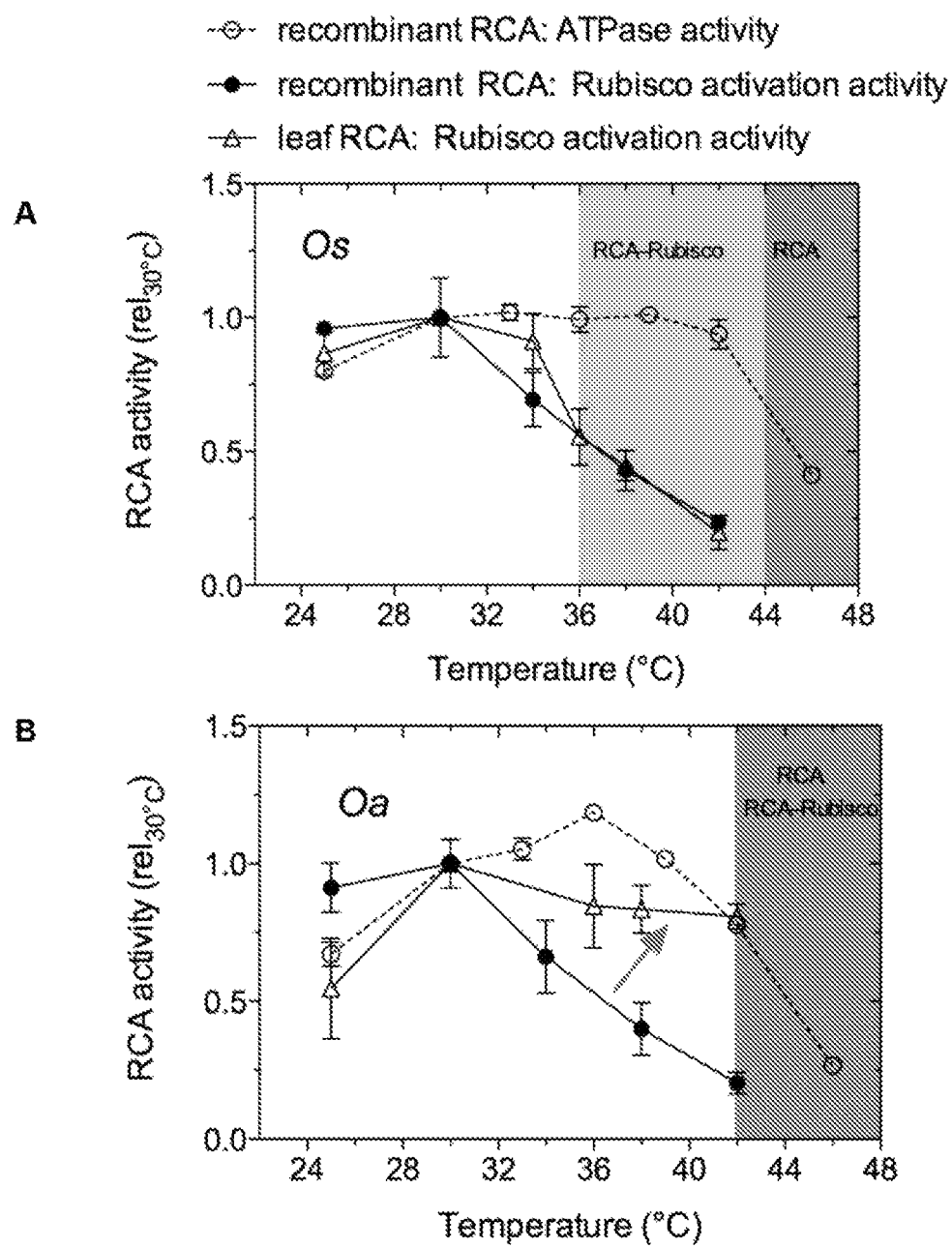
FIG. 21. Temperature-dependent stability of the self-aggregating RCA oligomer (open circles), the recombinant RCA-Rubisco complex (closed circles) and the native RCA-Rubisco complex (open triangles) for *O. sativa* (top panel) and *O. australiensis* (bottom panel). The arrow indicates the dramatic improvement in heat-stability of the *O. australiensis* native RCA-Rubisco complex relative to the recombinant complex. Due to the stability of the native complex, *O. australiensis* RCA is co-limited by both RCA-Rubisco and self-aggregation stability at a much higher temperature than *O. sativa*.

To establish temperature effects on the protein complexes of interest, samples were incubated at 28° C. or 38° C. for 20 minutes before loading on native gels. The higher temperature did not interfere with the individual Rubisco or RCA complexes. This supports the conclusion that while the Rubisco complexes and RCA complexes from Oa and Os exhibit different thermostability characteristics, each is stable at high temperatures and the interaction of the Rubisco with RCA (leaf extracted or recombinant), i.e. the Rubisco-RCA complex, is heat-labile, particularly in *O. sativa* (see FIG. 21).

SDS-PAGE separation of leaf-purified RCA from *O. australiensis* and from wheat. Total leaf protein was initially precipitated in 35% saturated ammonium sulphate followed by anion-exchange chromatography using Q-sepharose media and varying salt concentrations. The beta isoform eluted from anion-exchange at 0.2 M KCl while the alpha isoform eluted at 0.5 M KCl. The 0.2 M fraction containing RCA was used in subsequent assays of RCA interaction with wheat Rubisco.

Bands of interest from the native gels were excised and LC-MS/MS was run on trypsin-digested proteins extracted from those bands. Identified proteins are listed in Table 11. Protein identification was as expected with the clear identification of the two Rubisco subunits and identification of RCA ranging in molecular weight. Two proteins identified in some of the leaf-extracted RCA bands were glutamine synthase and sucrose synthase. It is unlikely that an interaction between RCA and glutamine or sucrose synthase is occurring, rather it is more likely that these proteins form complexes of similar molecular weight to RCA, therefore occupying the same band-space. Note that only the beta isoform of RCA was identified in all bands associated with RCA, however considering that the two isoforms are identical apart for 38 amino-acids at the C-terminus of the alpha isoform, it is likely that both were present but the peptide sequences had a higher probability of matching the identical regions and assigning the peptide to the beta rather than alpha isoform.

TABLE 11

| Spot Number | Protein Identification | Peptide Matches# |
|---|---|---|
| 1 | Rubisco large subunit | 30 |
| | Rubisco small subunit | 5 |
| 2 | Rubisco large subunit | 22 |
| | Rubisco small subunit | 6 |
| 3 | Peroxisomal hydroxyl-acid oxidase | 1 |
| 4 | RCA beta isoform | 21 |
| | Glutamine synthase | 5 |
| 5 | RCA beta isoform | 2 |
| 6 | RCA beta isoform | 6 |
| | Glutamine synthase | 1 |
| 7 | RCA beta isoform | 4 |
| | Sucrose synthase | 2 |

Refers to the total number of peptides that matched the identified protein.

Example 5: Concentration-Dependent Activity of RCA

Figure 5:
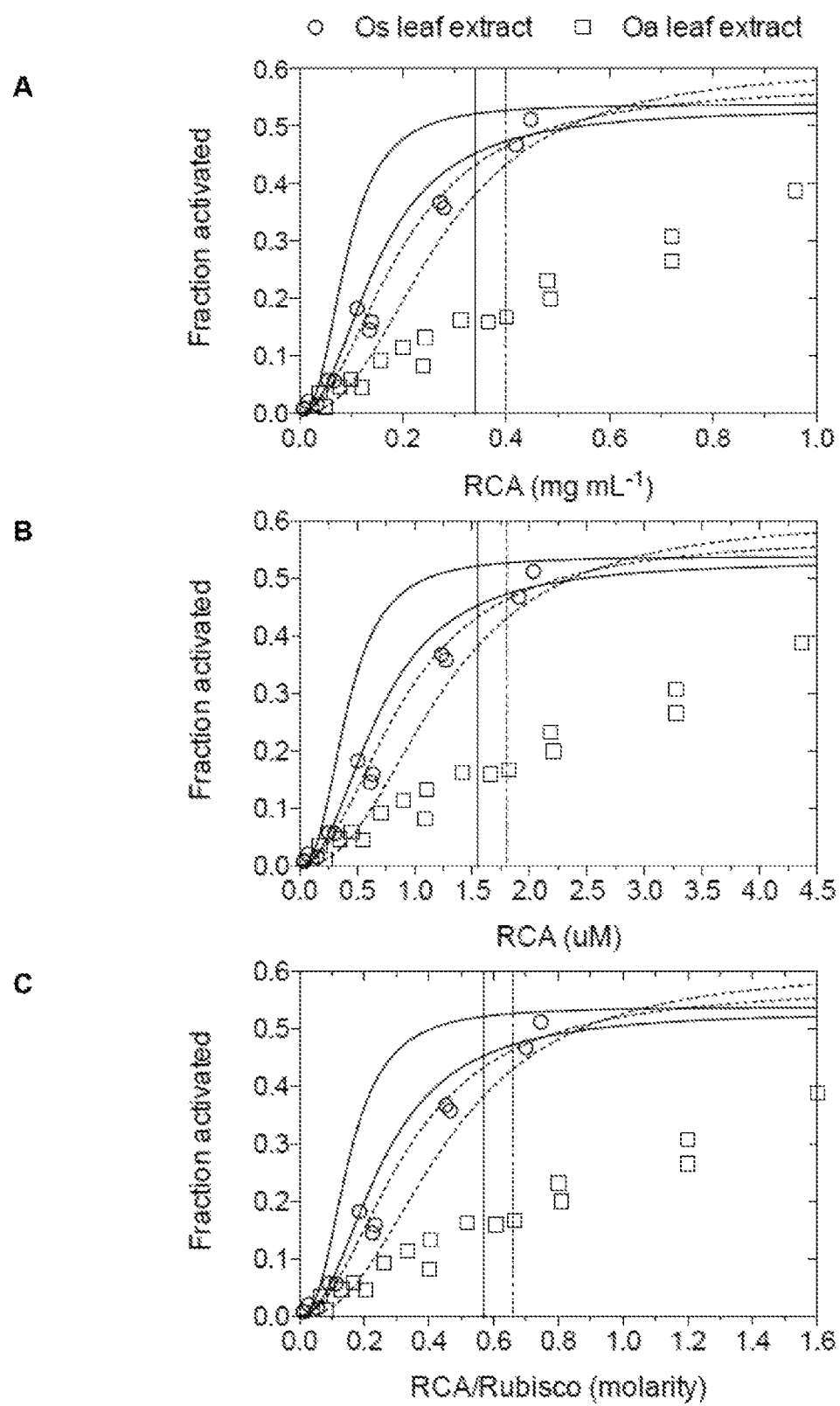
FIG. 5. Concentration-dependent Rubisco activation by leaf-extracted RCA from *Oryza sativa* (Os) (open circles) and *Oryza australiensis* (Oa) (open squares), as well as by recombinant RCA from Os (solid lines) and Oa (dashed lines). The two lines for each species represent the alpha and beta recombinant isoforms, with the beta isoform always more active and therefore the upper line. RCA concentration is given in mass per volume, molarity and the molar ratio of RCA to Rubisco within the assay. For all assays the Rubisco concentration used was 1.5 mg·mL$^{-1}$ (2.7 µM). Molarity was calculated using the molecular weight of the complete Rubisco complex (553 kDa) and active complex of RCA (220 kDa) based on oligomer formation (Keown, J. R., et al., (2013). *J. Biol. Chem.* 288, 20607-20615.). The solid vertical line and the dashed vertical line represent the expected in vivo concentration of RCA from Os and Oa, respectively, given the Rubisco concentration used. All measurements were taken at 30° C.

FIG. 5 shows the concentration-dependent Rubisco activation rate of leaf-extracted RCA from *O. australiensis* and *O. sativa*, as well as Os (solid lines) and Oa (dashed lines) alpha and beta recombinant isoforms. The Rubisco activation assay was performed essentially as described by Barta, C., Carmo-Silva, A. E. & Salvucci, M. E. (2011) Methods Mol. Biol. 684, 375-382, with two modifications: (1) the quenched second-stage assay samples were dried on a heating block before resuspension in scintillation cocktail prior to counting; (2) all reported Rubisco activation assays were of inhibited Rubisco incubated with RCA for 5 min prior to determining Rubisco activity. Recombinant RCA was produced as described in Barta, C., Carmo-Silva, A. E. & Salvucci, M. E. (2011) Methods Mol. Biol. 684, 363-374. The following plasmids were used: pEV61, pGA220, pEV63 and pGA221 encoding O. sativa RCA alpha and beta isoforms and O. australiensis alpha and beta isoforms respectively. As well as giving the absolute RCA concentrations used in assays, the molar ratio of RCA to Rubisco is also given, as the activation reaction is dependent on the concentration of Rubisco as well as RCA. Oa-leaf RCA can reach high rates of activity relative to Os RCA when high concentrations of RCA with a molar ratio of RCA to Rubisco of 1:6 were used. Under these conditions, rates of activation are increased relative to those for the recombinant form of RCA. This molar ratio is well above what is found in the leaf and marked in FIG. 5 by the vertical lines. It is unlikely that the low in vitro specific activity of leaf-extracted RCA from Oa would be reflected in vivo because photosynthetic rates between the two species are similar, which would not be the case if Oa RCA was functioning at only 40% of Os rates. The reduced in vitro specific activity in Oa is therefore likely to be related to in vitro measurements for a reason yet unknown. Interestingly, Os leaf RCA also has a lower specific activity when compared with its recombinant counterpart but the difference is minimal).

Figure 6:
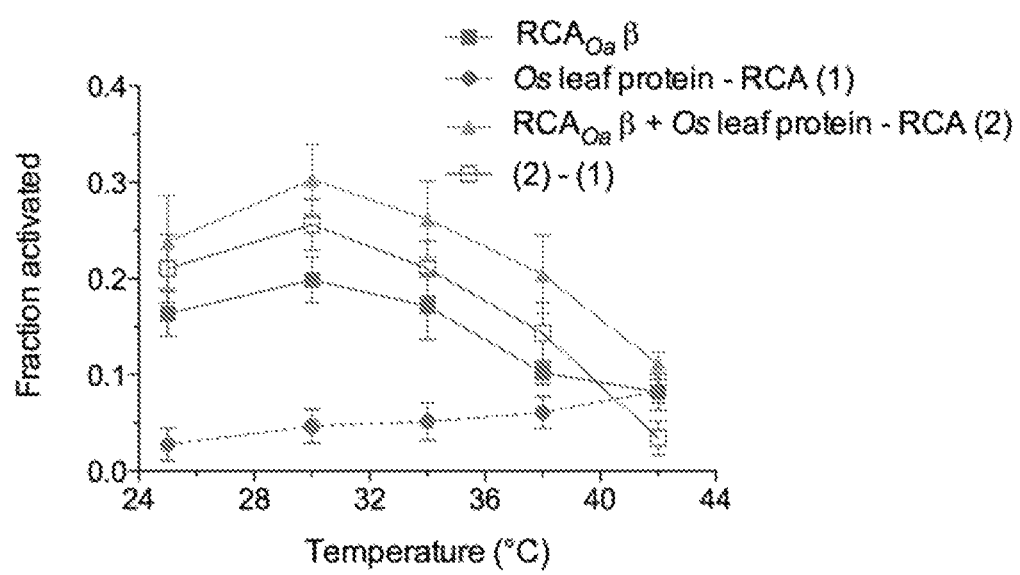
FIG. 6. The influence of leaf-extracted proteins on the thermostability of recombinant Oa beta RCA (activity shown by filled squares). Values are the means±SE of three experimental replicates. The open squares were derived by subtracting the blue-filled circles (leaf protein extract with RCA removed) from the filled triangles (recombinant Oa beta RCA incubated in leaf protein extract with RCA removed).
Figure 7A:
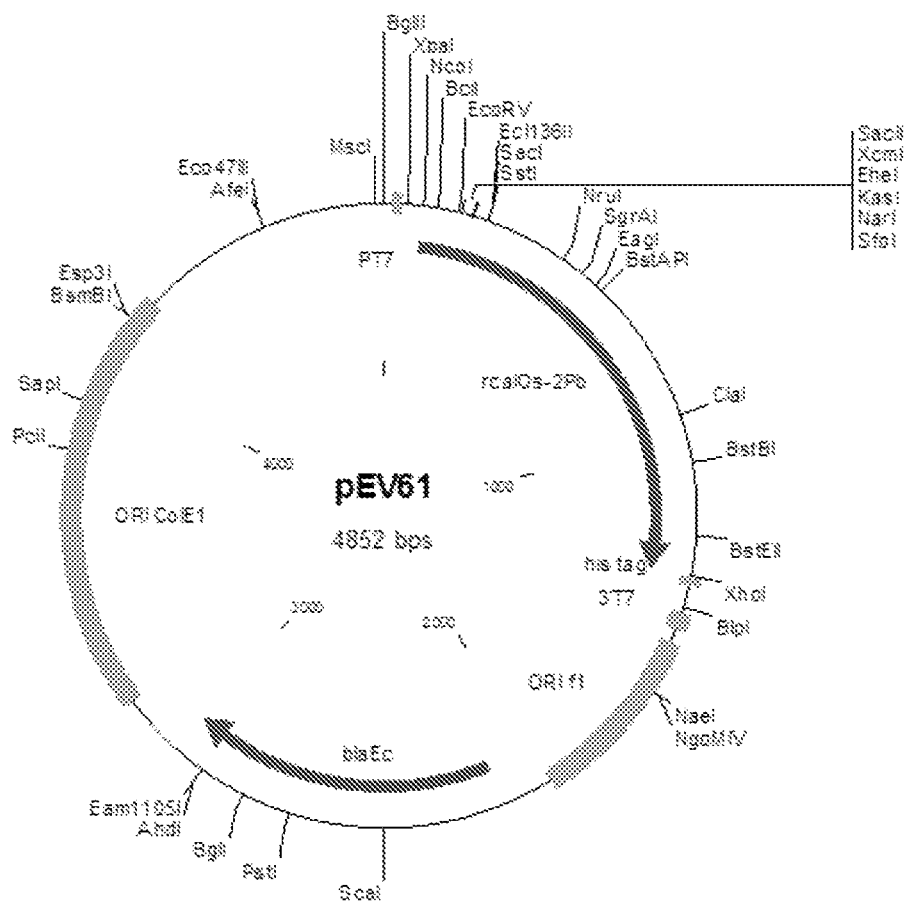
FIGS. 7(A)-(G). Vector maps of plasmids containing RCA genes, adapted to *E. coli* codon usage, for expression in *E. coli* and the nucleotide sequence of the respective RCA genes. All RCA genes were cloned into pET-23d+.
Figure 7B:
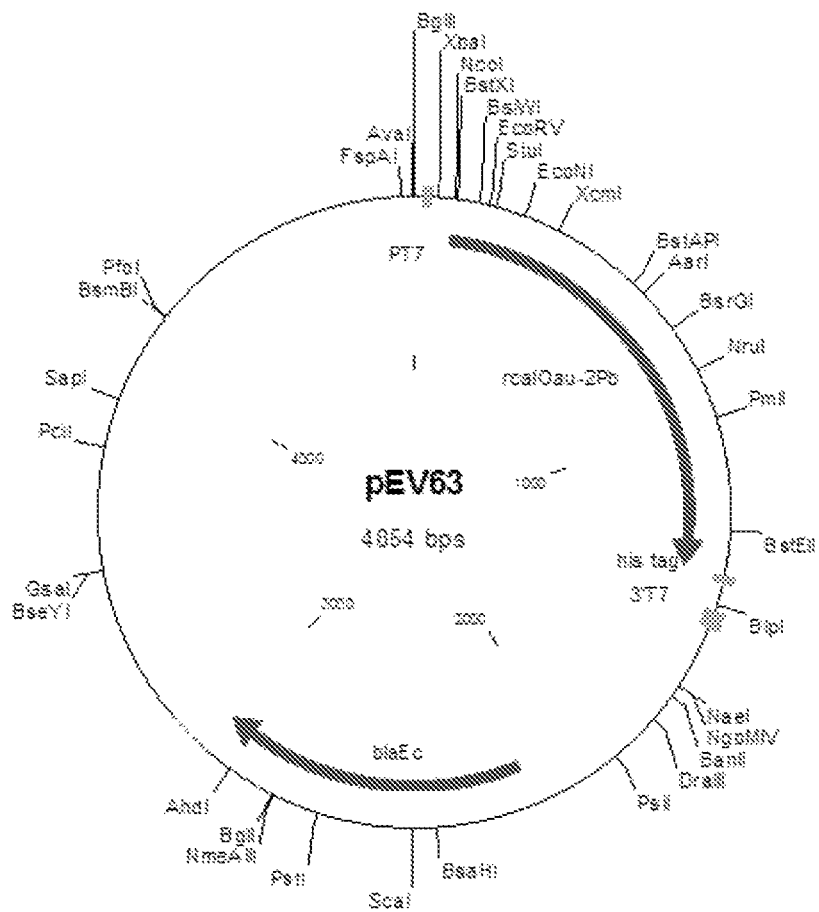
Figure 7C:
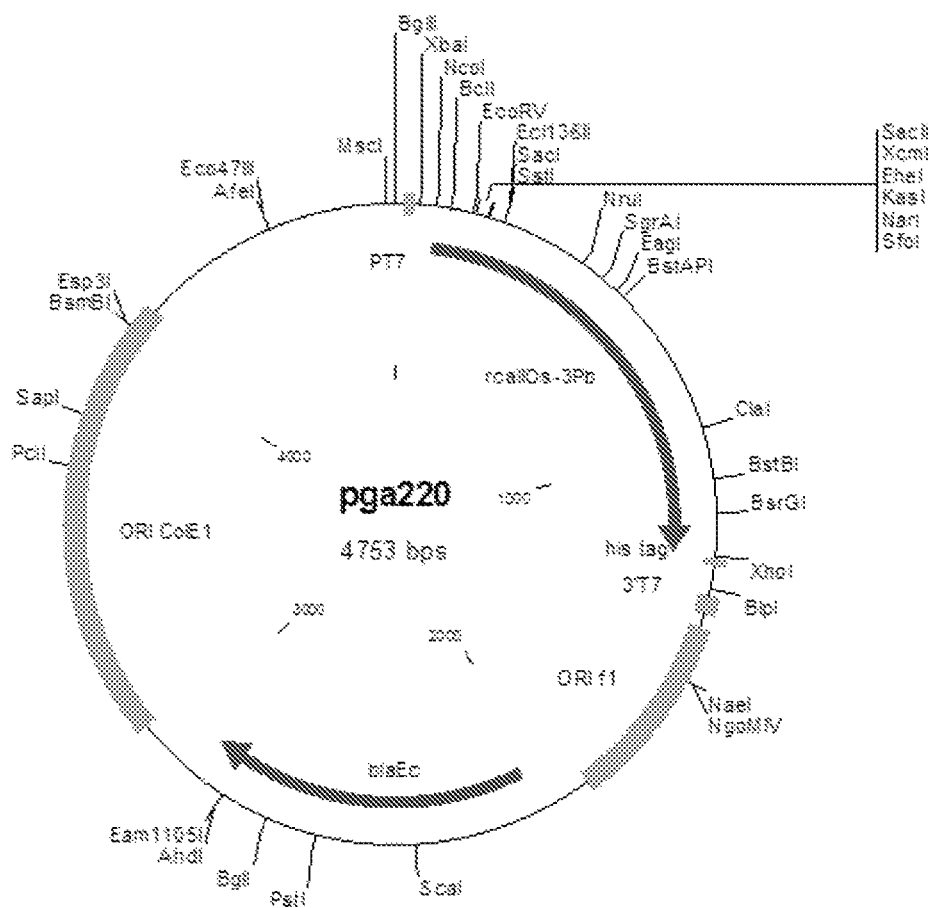
Figure 7D:
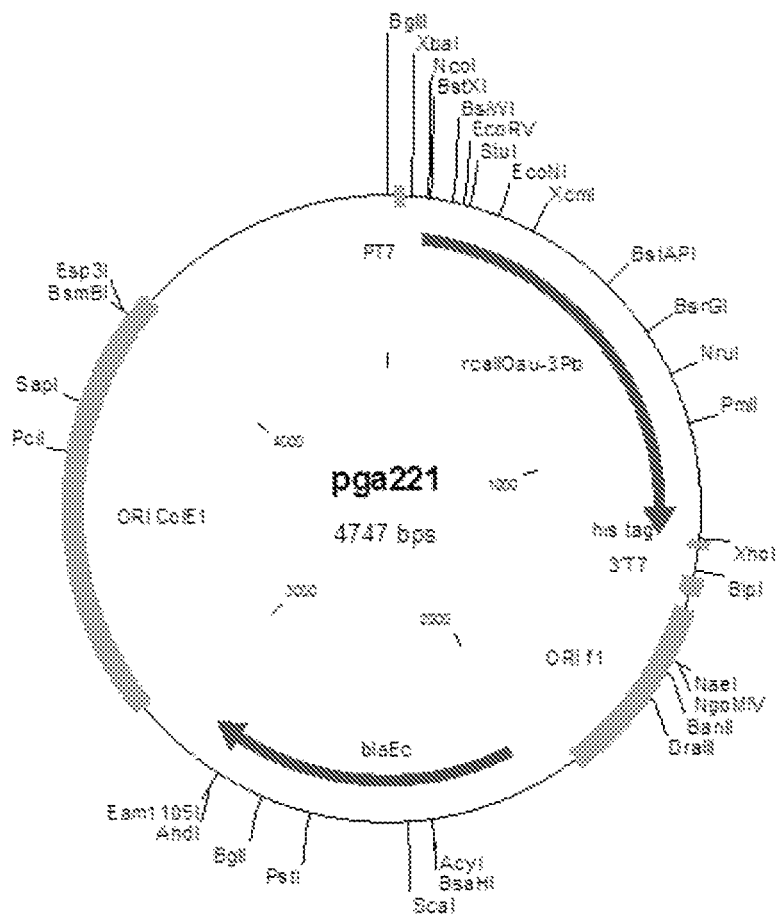
Figure 7E:
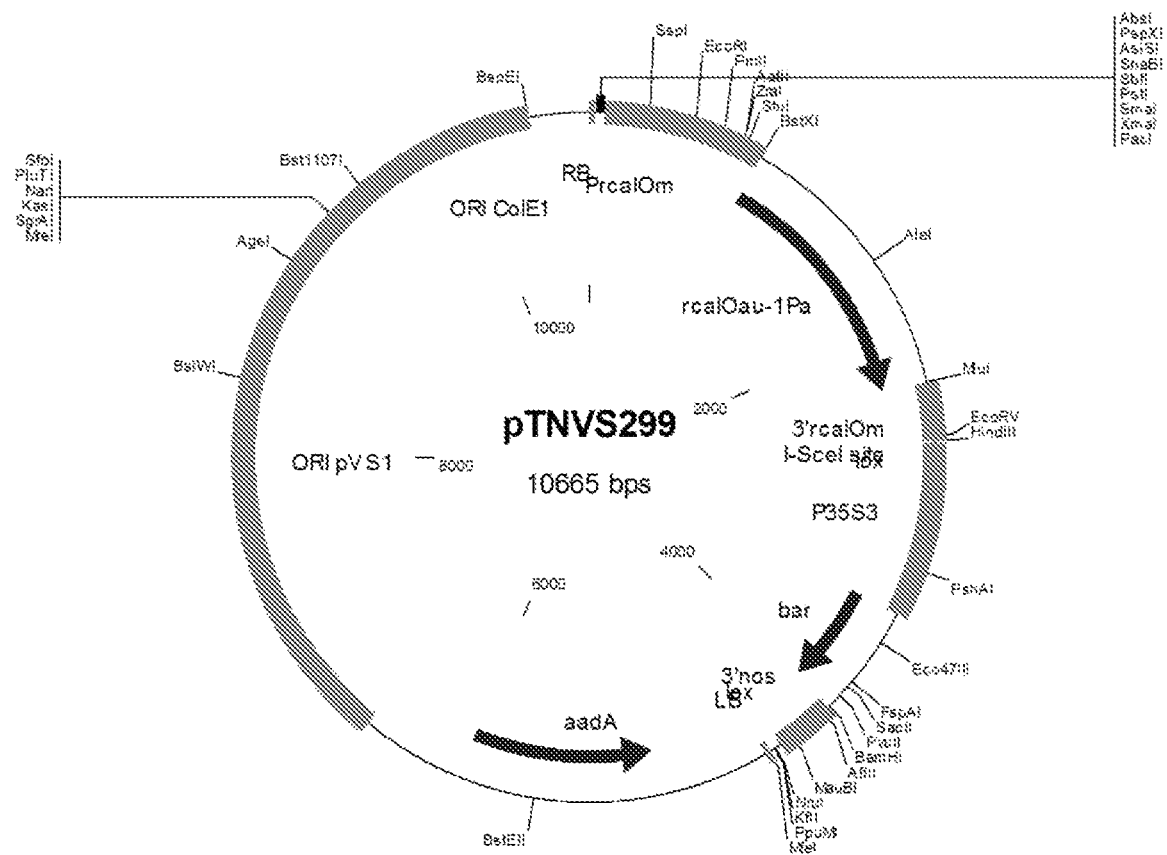
Figure 7F:
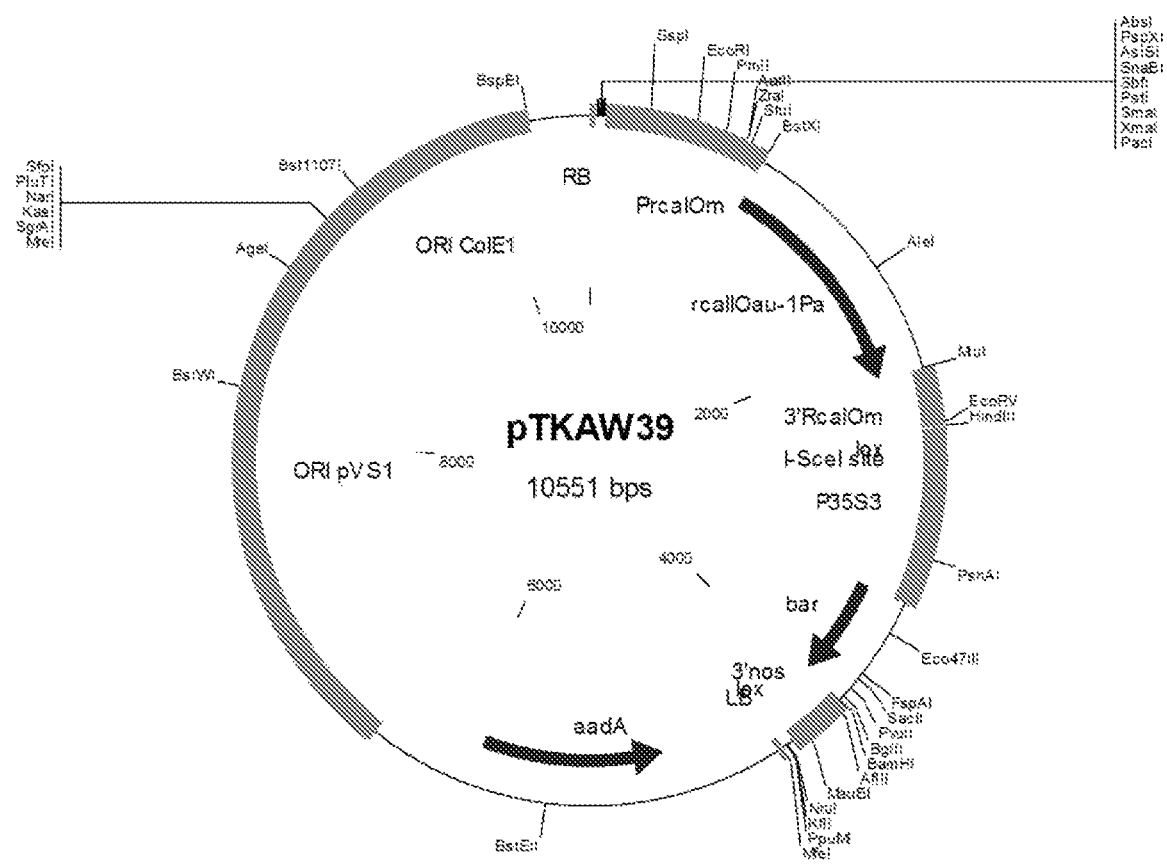
Figure 7G:
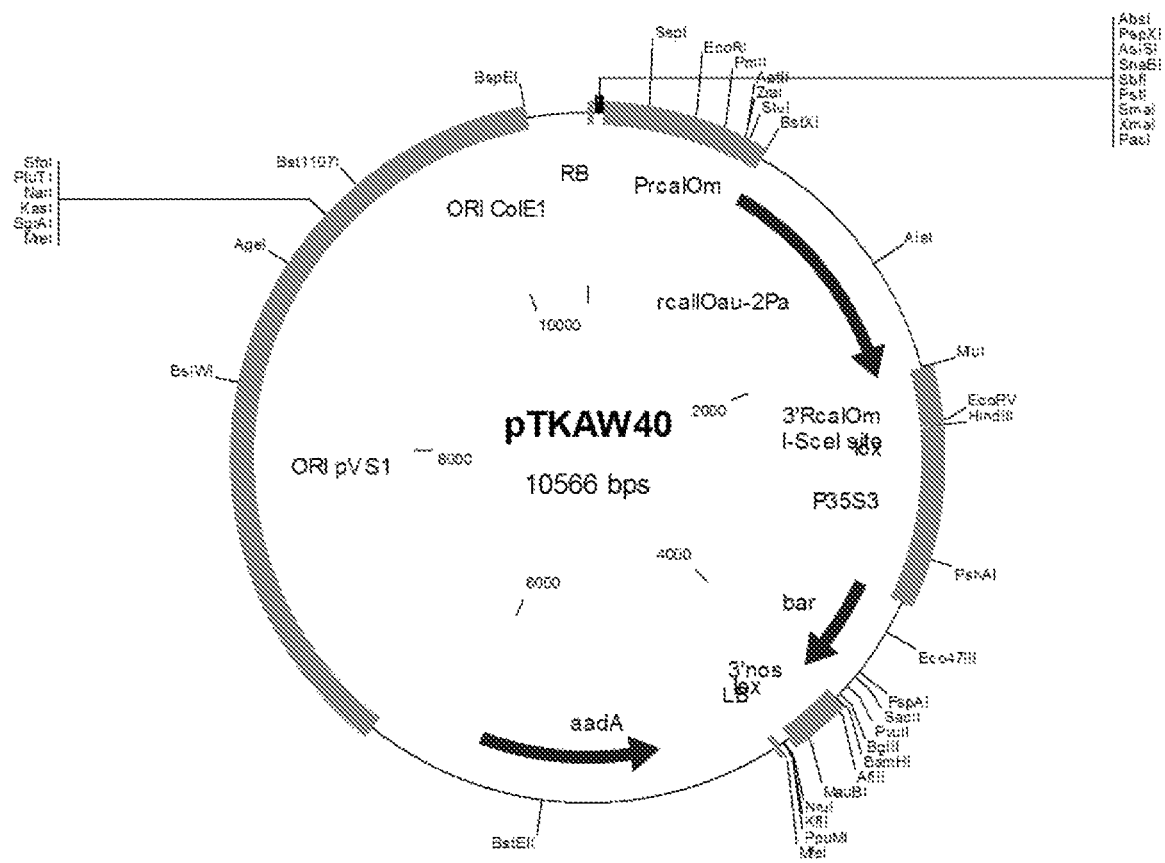

If the lower specific activity seen in RCA extracted from Oa leaf were to be caused by a non-specific inhibitory substance, it would be expected that such a substance would also inhibit recombinant RCA. To test this we ran a mixing experiment where Os leaf extract, from which RCA had been removed, was added to recombinant Oa beta RCA and RCA activity measured (FIG. 6). No inhibition of the recombinant protein was observed when leaf extract, depleted in RCA, was added to it.

Example 6: RCA Heat-Stability

To determine the heat-stability of RCA three techniques were used. Two techniques, the NADH coupled assay and the phosphate assay measure the hydrolysis of ATP by RCA, which is a function the enzyme performs irrespective of the presence of Rubisco but is specifically necessary for Rubisco activation. The third technique, the Rubisco activation assay, directly measures the ability of RCA to activate Rubisco by assessing $CO_2$ binding. All three techniques require RCA to be purified, at least partially. For Rubisco activation assays, Rubisco as well as RCA must be purified prior to experimentation. Experiments used either partially purified RCA from leaf extracts or complete purification of recombinant protein expressed in E. coli.

Example 7: RCA Recombinant Gene Expression and Protein Purification

The transformed E. coli containing the vectors pEV61 (containing the rcaIOs-2Pb gene (encoding the O. sativa long isoform RCA)), pEV63 (containing the rcaIOau-2Pb gene (encoding the O. australiensis long isoform RCA)), pGA220 (containing the rcaIIOs-3Pb gene (encoding the O. sativa short isoform RCA)) and pGA221 (containing the rcaIIOau-3Pb gene (encoding the O. australiensis short isoform RCA)) for expression of the O. sativa and O. australiensis and isoforms of RCA. The plasmid maps of these vectors are given in FIG. 7(A)-7(G). The expression and purification of RCA allowed for analysis of the heat-stability of the enzyme. As the expression vector allowed for relatively high concentrations of the protein to be produced, the protein could be highly purified. Contrastingly, lower concentrations of RCA extracted from leaves did not allow for leaf-extracted RCA to be purified to the same extent as dilution during gel filtration chromatography led to the loss of the RCA complex and subsequently an inability to purify the protein to a high degree.

All of the vectors except pGA221 expressed RCA and for every 100 ml of cell culture approximately 2.5 mg of protein was purified. The purification of recombinant RCA involved precipitation of the RCA by adding saturated ammonium sulphate to the homogenised E. coli cell extract. Precipitated RCA was then suspended in buffer and loaded onto a gel-filtration column and the relevant peak collected. A second chromatographic step of passing the RCA through a strong anion-exchange column provided the final purified RCA. Running the purified protein on a gel showed the extent of the purification, with almost no other proteins visible.

Example 8: RCA from Leaf Extracts and Partial Purification

Unlike purification of the recombinant protein, leaf-extracted RCA was more challenging to work with, which is why rice RCA has never been successfully analysed in vitro. A couple of attempts to purify leaf extracted RCA in a similar manner to purification of the recombinant protein failed. The challenge with leaf-extracted RCA is the limited amount of RCA available per unit of leaf and the presence of proteases which quickly degrade the protein. Partial purification of RCA from leaf extract was possible, which involved precipitating out RCA with saturated ammonium sulphate, followed by desalting. While RCA was by no means the only protein left in the sample, it was the most abundant and gels indicated that there was little degradation by proteases. As RCA is the only protein responsible for activation of Rubisco, the presence of other proteins in the sample has little effect on the $^{14}$C-Rubisco activation assays. Activation assays performed on leaf-extracted RCA samples are useful as the impact of post-translational modifications and protein-protein interactions on the activity of RCA are at least partly accommodated. In other words, this assay is more representative of what can be expected in vivo in transgenic plants.

SDS-PAGE Gel image analysis of the partially purified leaf extracts show O. australiensis had a lower content of RCA, which was factored into some Rubisco activation results. However, the concentration of RCA in relation to partially purified protein extracted from the leaf was similar between O. sativa and O. australiensis, being about 25% of the partially purified protein for both species. Similar concentrations of RCA between the species observed in leaf extracts is highly relevant to gene expression and protein abundance.

Gels showed O. sativa to have a greater abundance of the isoform relative to O. australiensis, with O. sativa having about equal quantities of the two isoforms while O. australiensis has much more β than a isoform. The ratio of the two isoforms seems to change with growth temperature. In particular, O. sativa grown for 72 hours at a raised day temperature of 40° C. had almost no visible β form but substantially more α form relative to plants grown at a day temperature of 30° C.

Example 9: Rubisco Purification

For the Rubisco activation assay purified Rubisco, the substrate in the assay, is also required. One gram of leaf fresh weight yielded approximately one milligram of Rubisco. Purification of Rubisco involves extraction from leaves followed by precipitation of the protein with saturated ammonium sulphate. Following ammonium sulphate precipitation the sample was passed through a sucrose gradient using high-speed centrifugation with the large Rubisco complex migrating to higher concentrations of sucrose. Following sucrose gradient separation the sample was separated by anion-exchange chromatography resulting in a highly pure extract of Rubisco.

Example 10: ATPase Assays

Figure 8:
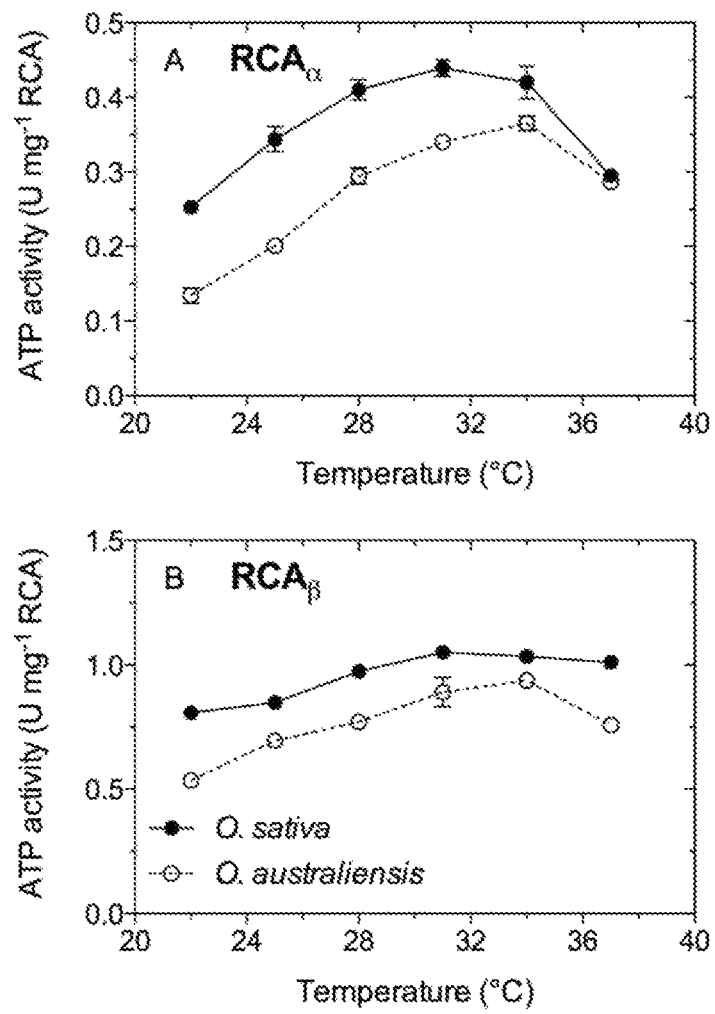
FIG. 8. ATP hydrolysis activity of the α (panel A) and β (panel B) recombinant RCA isoforms from *O. sativa* (filled circles/solid line) and *O. australiensis* (open circles/dashed line) calculated using the NADH coupled assay.
Figure 9:
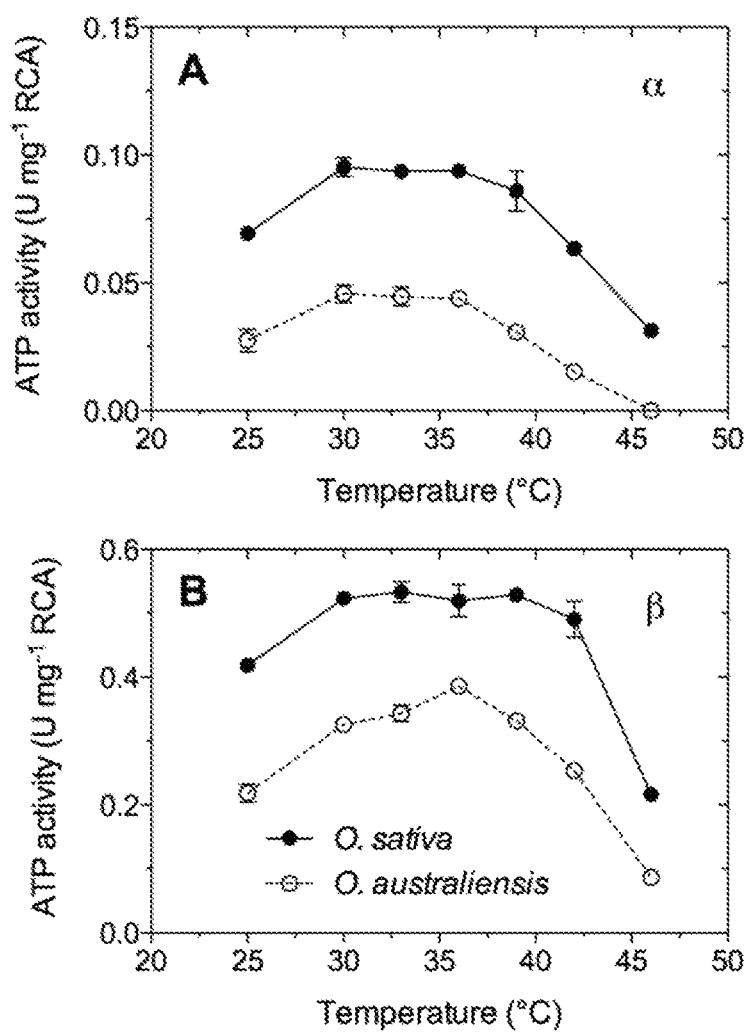
FIG. 9. (panel A) ATP hydrolysis activity of the α recombinant RCA isoforms from *O. sativa* (filled circles/solid line) and *O. australiensis* (open circles/dashed line) calculated using the phosphate release assay. (panel B) ATP hydrolysis activity of the β recombinant RCA isoforms from *O. sativa* (filled circles/solid line) and *O. australiensis* (open circles/dashed line) calculated using the phosphate release assay.

RCA requires ATP to activate Rubisco. The ATPase activity of RCA is not directly related to the Rubisco activation activity, as Rubisco is not required for ATP hydrolysis to occur. The ATPase activity of RCA from both species (Oa and Os) was measured over a range of temperatures. Two alternative methods were used to determine ATPase activity. Firstly, a coupled reaction involving the conversion of NADH to $NAD^+$ and the subsequent change in absorbance at 340 nm was measured (FIG. 8). Alternatively the production of phosphate when ATP is converted to $ADP+P_i$ was measured (FIG. 9). A similar temperature response was observed between the two methods.

Results from both ATPase activity based assays show that, irrespective of species, the β isoform has a substantially higher specific activity than the α isoform.

Figure 10:
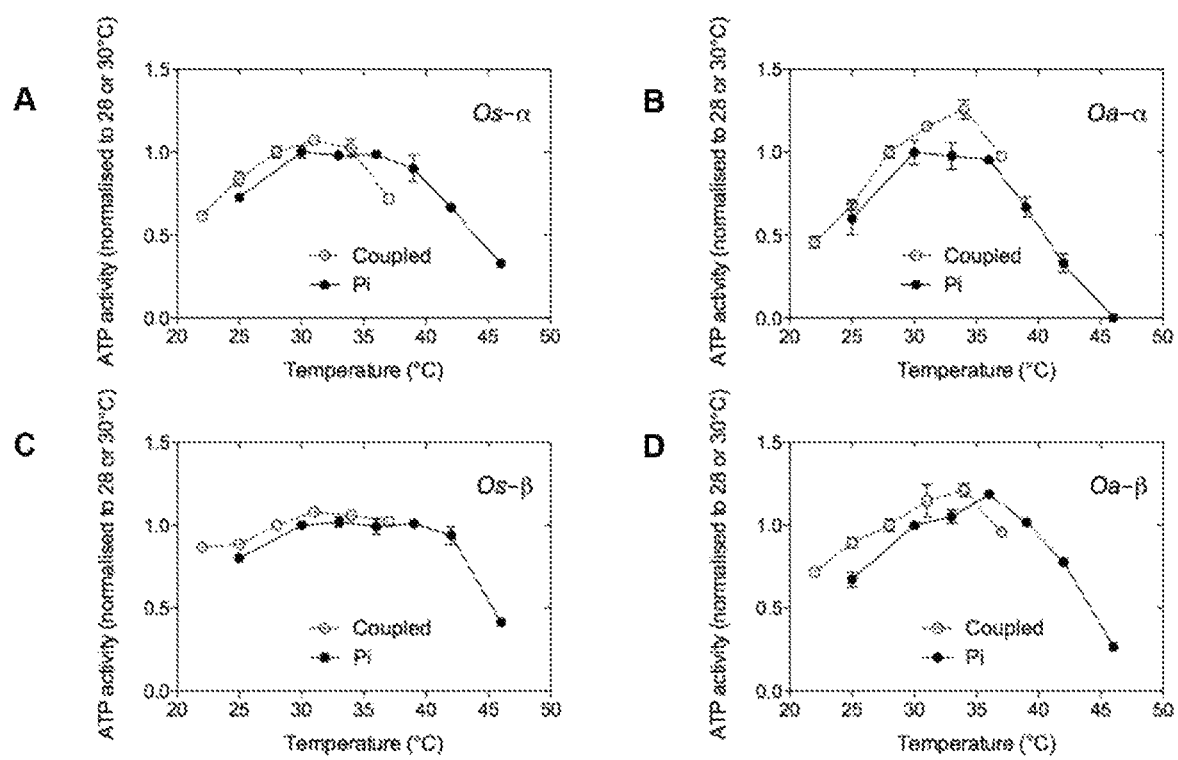
FIG. 10. ATP hydrolysis activity of *O. sativa* (Os) or *O. australiensis* (Oa) recombinant RCA determined by the NADH coupled assay (open circles) or the phosphate release assay (closed circles) normalised to 28° C. and 30° C., respectively. Note that both methods give a similar temperature response of ATP hydrolysis except for a displacement to higher temperatures when phosphate release is assayed.

To compare the temperature response between the two methods used to determine ATP hydrolysis (the phosphate and NADH coupled reaction), normalised values attained from both methods were plotted together (FIG. 10).

Example 11: $^{14}C$ Rubisco Activation Assays

A two-stage assay in which RCA is initially incubated with inactivated Rubisco for a set period of time, followed by measurements of Rubisco specific activity, allows for determination of the efficiency of RCA activation of Rubisco. For all of the experiments, inactivated Rubisco was incubated with RCA for a period of five minutes at given temperatures. The total activity of Rubisco, independent of RCA, was determined by removing Rubisco from the incubation mix allowing for all Rubisco sites to become active. Of note, at temperatures as high as 42° C. the total activity did not fall but increased slightly. The absence of a reduction in total Rubisco activity with increasing temperature supports the consensus view that RCA is heat labile while Rubisco is relatively insensitive to high temperature (Salvucci, M. E. & Crafts-Brandner, S. J. (2004) Plant Physiol. 134, 1460-1470; Crafts-Brandner, S. J. & Salvucci, M. E. (2000) Proc. Natl. Acad. Sci. U.S.A 97, 13430-13435.).

Figure 11:
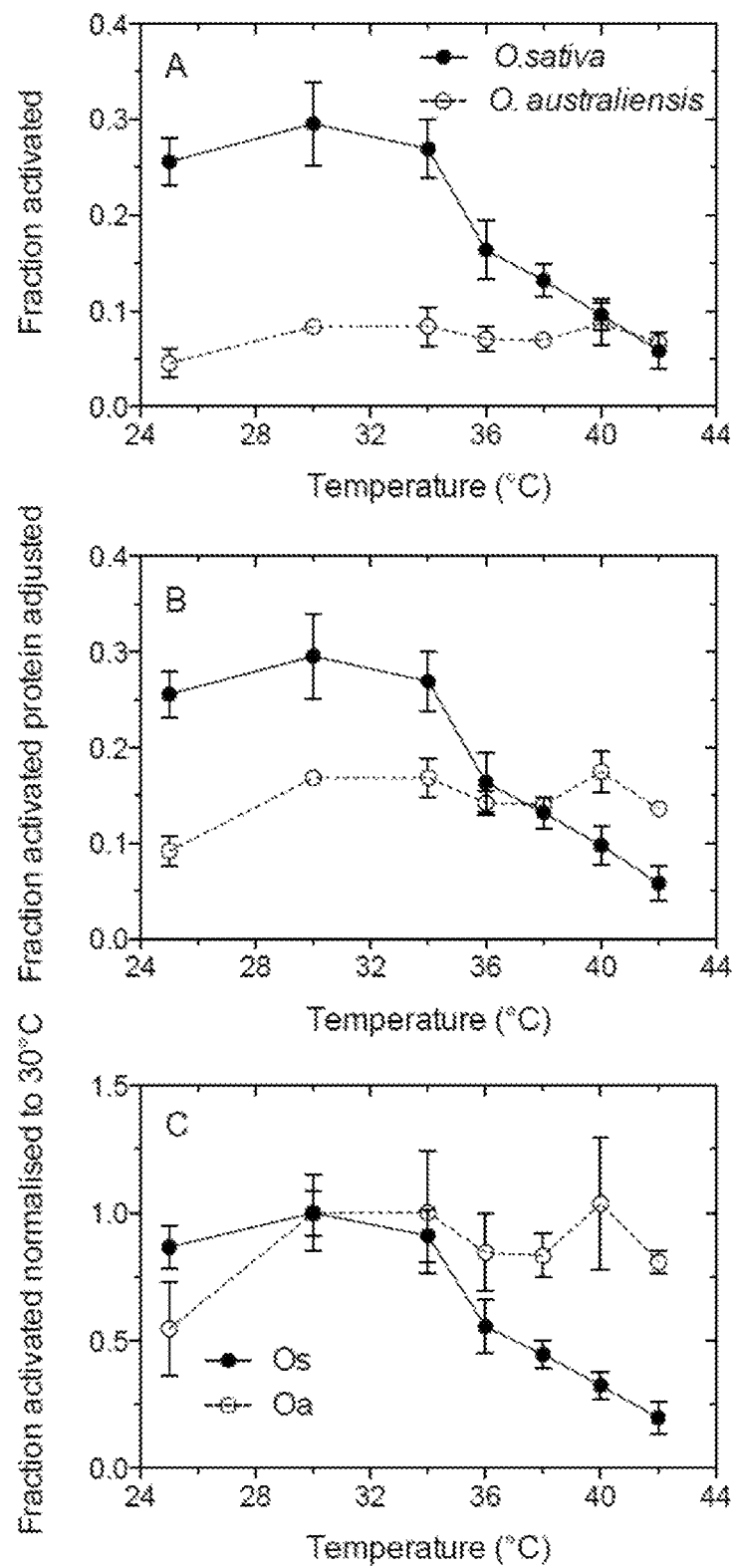
FIG. 11. Temperature-dependent Rubisco activation activity, determined using the same assay as in FIG. 13, for leaf-extracted RCA$_{Os}$ (filled circles/solid lines) and leaf-extracted RCA$_{Oa}$ (open circles/dashed lines). Activation rates are given as individual measurements of the three biological replicates over the temperature range with quadratic equations fitted (panel A), after differences in RCA protein concentration between the species were accounted for (panel B) and when protein adjusted values were normalised to values measured at 30° C. (panel C).

Two independent sets of experiments measuring the activity of leaf-extracted RCA were undertaken. FIG. 11 relates to RCA extracted from leaf material. RCA was extracted from leaf material of three occasions and results are based on three biological replicates and up to eight technical replicates. Measurements were made at 25, 30, 34, 36, 38, 40 and 42° C. The activation values have not been adjusted for differences in RCA concentration between the two species, as the amount of purified protein extract added to each assay was unknown. The change in activation with temperature is therefore more informative than the absolute values given (FIG. 11 panel (a)).

The values were subsequently adjusted for RCA concentration differences between the two species (FIG. 11 panel (b)).

Rubisco activation shows $RCA_{Os}$ to be more active at a temperature of 30° C. but the activity of $RCA_{Os}$ declines sharply at temperatures of 36° C. and above. Contrastingly, $RCA_{Oa}$ is less active at moderate temperatures but the enzyme maintains close to a constant rate up to temperatures of 42° C. Analysis of individually plotted curves give a peak in RCA activation performance of 29.9±0.5° C. for *O. sativa* and 33.0±0.3° C. for *O. australiensis*.

After differences in RCA protein concentration between the species are accounted for, activation at 36° C. is not significantly different between the species (as indicated in FIG. 11 panel (b)). Furthermore, at higher temperatures of 38 and 42° C. $RCA_{Oa}$ activity is greater. When protein adjusted values are normalised to 30° C. the tolerance of $RCA_{Oa}$ activity at temperatures above 38° C. is even more apparent (see FIG. 11 panel (c)).

Figure 12:
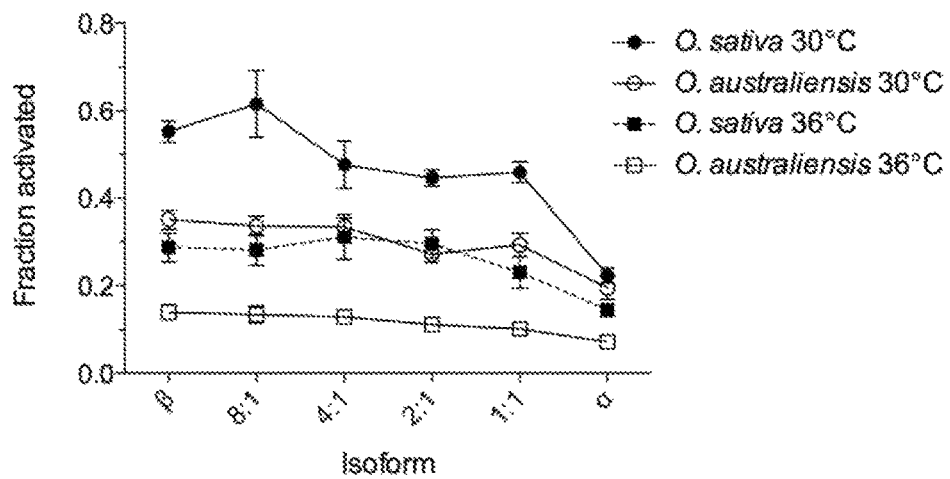
FIG. 12. Rubisco activation activity of recombinant RCA measured at either 30° C. or 36° C. The two isoforms of RCA were measured in isolation or mixed in α to β ratio of 8:1, 4:1, 2:1, 1:1. Values are means SE of three experimental replicates.

Analysis of Rubisco activation by the recombinant purified protein was also undertaken (FIG. 12). The recombinant protein was measured at 30 and 36° C. Interpretations from previous work have led to an expectation that a higher ratio of α to β isoform would improve heat stability of the enzyme. However, with an increasing ratio of α isoform the activity of the RCA complex falls. The fall in activity with increased α isoform is more pronounced for *O. sativa* and more so at 30° C. than at 36° C., however the pattern seems to exist for both species and temperatures. Interestingly, although the β isoform of $RCA_{Os}$ has higher activity than $RCA_{Oa}$ there is little difference in activity of the α isoform between the species.

Figure 13:
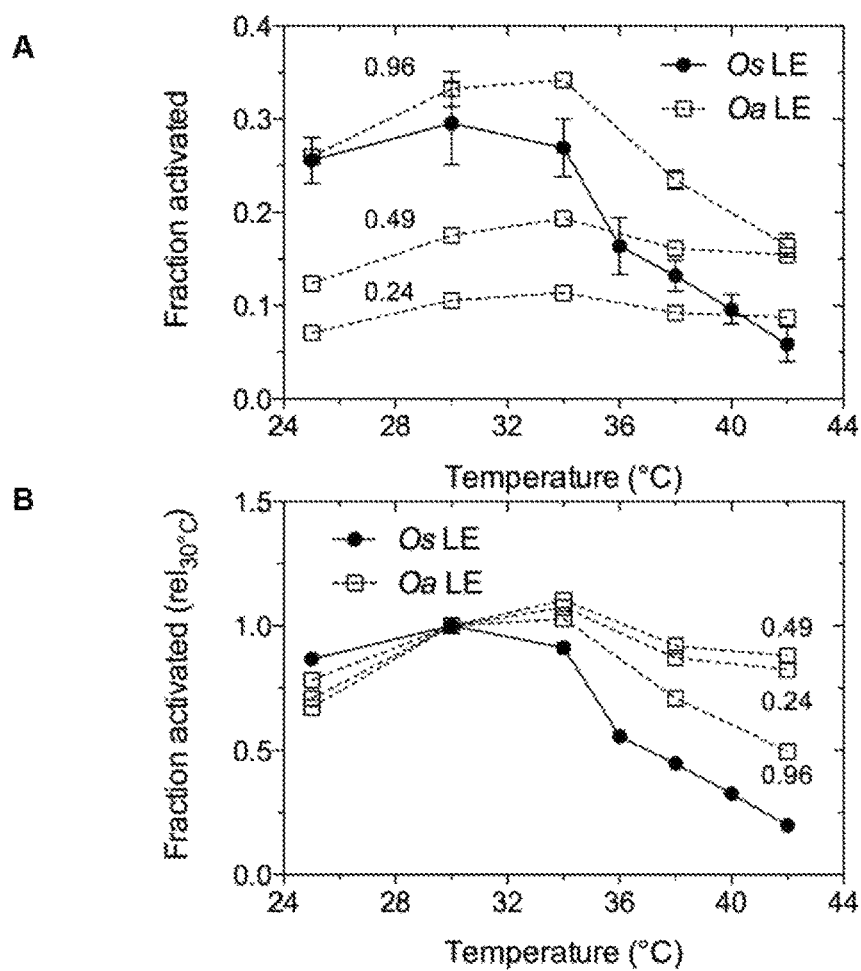
FIG. 13. Temperature-dependent activation of Rubisco by RCA extracted from Os and Oa leaf extracts (LE) and measured at a concentration of 0.2 mg·mL$^{-1}$ for Os and varying concentrations of 0.24, 0.49 or 0.96 mg·mL$^{-1}$ for Oa (indicated by values next to corresponding curves). A constant 1.5 mg·mL$^{-1}$ Os Rubisco concentration was used in all assays. The top panel is absolute values and the bottom is values relativized to 30° C.

Until now Oa-leaf RCA heat-stability has only been measured at a fraction activated level of ≤0.1 Oa-leaf RCA and has now been measured as fraction activated rates >0.3 by increasing the concentration of extracted leaf protein and consequently RCA concentration. To evaluate whether the heat-stability of Oa-leaf RCA is maintained even when the activity matches that of Os, a temperature response curve of Rubisco activation was performed with varying concentrations of Oa leaf-extracted RCA (FIG. 13).

When Rubisco activation in Oa extracts was enhanced by using enzyme concentrations comparable to those in Os extracts, RCA from the leaf of Oa exhibited superior heat-stability relative to that from Os. The highest concentration of Oa RCA measured had the same absolute rate as Os RCA at 25° C. Above 25° C. the activity of Oa RCA outperformed Os RCA and at 42° C. Oa had an absolute rate of activity four-times that of Os. It seems from the current results that heat-stability is slightly reduced when the concentration is as high as 0.96 mg·$mL^{-1}$, with close to a 50% drop in activity at 42° C. relative to 30° C., compared with less than a 20% fall at concentrations of 0.24 and 0.49 mg·$mL^{-1}$. It may reflect a stoichiometric relationship between RCA and Rubisco. However even at this 'high' concentration, the fraction activated is still well above the 80% reduction by Os RCA at comparable temperatures.

Example 12: Thermostability of the Rice RCA Oligomer

Figure 14:
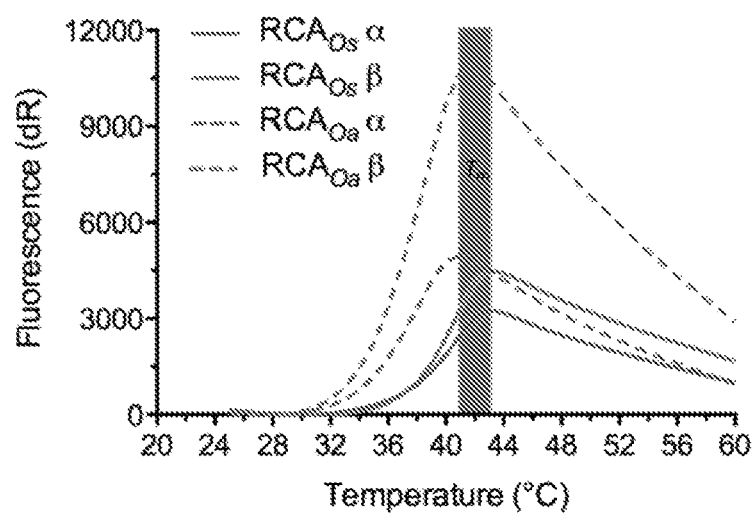
FIG. 14. Differential Scanning Fluorimetry (DSF) of the alpha and beta isoforms of recombinant *O. sativa* (solid lines) and *O. australiensis* (dashed lines) RCA. The first derivative of detected fluorescence (dR) is plotted against temperature and the maximum in dR corresponds to the melting temperature of the protein (T$_m$). One mg·mL$^{-1}$ of protein was used for all samples. Each curve is the mean of three sample replicates. The shaded area represents the range of T$_m$ across the four variants of RCA, extending from 41 to 43° C.

Differential Scanning Fluorimetry (DSF) is a relatively new and simple way of determining the thermal stability of proteins. It relies on the signal of a dye that preferentially fluoresces in a non-polar (unfolding protein) rather than polar environment (folded or aggregated protein). DSF was performed on recombinant $RCA_{Os}$ and $RCA_{Oa}$ using SYPRO Orange dye and a temperature ramping of 1° C. per minute from 25° C. to 90° C. (FIG. 14). First derivative (dR) values of fluorescence were plotted against temperature, with the protein melting temperature ($T_m$) being the temperature at which the first derivative was at a maximum. $T_m$ is the temperature at which there are equal concentrations of folded and unfolded protein. FIG. 14 shows that all four RCA variants have a $T_m$ ranging from 41 to 43° C. This supports the main conclusions of the ATPase activity results. Specifically, that the RCA oligomer is heat-stable at temperatures up to 40° C. and that there is little difference in the heat-stability of the RCA oligomer between the two species.

Example 13: Heat-Dependent Regulation of RCA Isoforms

Protein abundance of the alpha and beta isoforms of RCA from heat-treated rice plants was examined and the same samples were subjected to anion-exchange chromatography and run on SDS-PAGE gels. The benefit of the anion-exchange sample preparation step is that the two isoforms of RCA can be seen more clearly. Interestingly, there is much less alpha isoform present in Oa than what looked to be present in the original ammonium sulphate precipitated samples. Possibly there was an overlapping protein that made it seem like the previous samples of Oa had a greater abundance of the alpha isoform.

Figure 15:
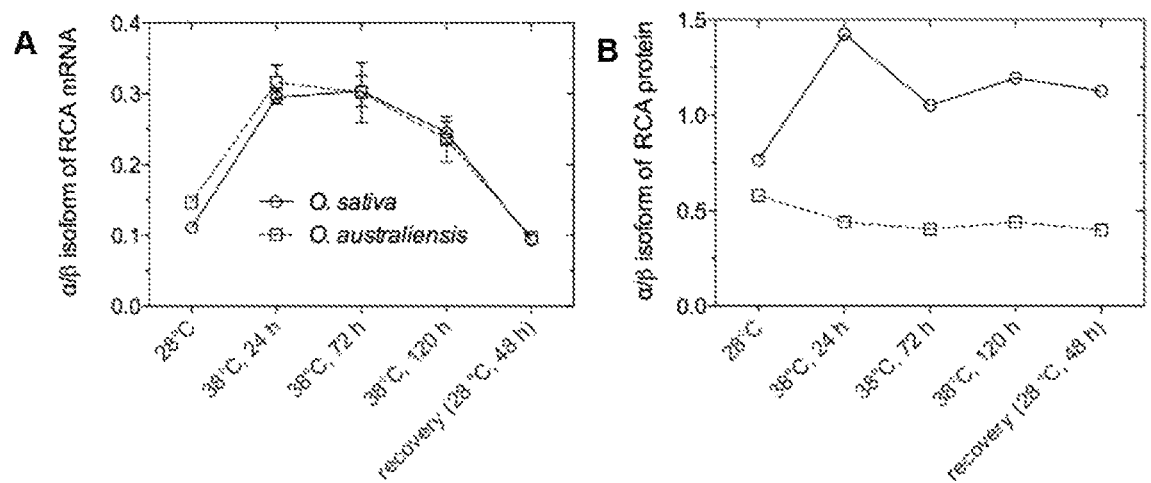
FIG. 15. Heat-dependent response of gene expression for the alpha and beta isoforms of RCA (left) and heat-dependent protein abundance of the alpha and beta isoform of RCA generated from image analysis of anion-exchange purified leaf samples. The ratio of the alpha to beta isoform is presented as alpha divided by beta mRNA or alpha divided by beta protein.

Image analysis SDS-PAGE gel alongside RCA isoform gene expression shows a broadly similar pattern of response to higher growth temperatures between gene expression and protein abundance of the two Os isoforms (FIG. 15). The RCA isoform gene expression analysis was performed as described by Scafaro, A. P., Haynes, P. A. & Atwell, B. J. (2010) J. Exp. Bot. 61, 191-202. With increased temperature, both gene expression and protein abundance of the Os alpha isoform increase within 24 h but level off and fall thereafter. Despite the similar response of the Os RCA isoform to increased temperature, there is a marked quantitative divergence between gene expression and protein abundance, as the alpha isoform only constitutes 30% of beta RCA mRNA but there was 50% more alpha than beta RCA protein after 24 h at 38° C. In contrast to Os, heat increased expression of the alpha isoform of Oa but did not enhance the alpha isoform of the protein product.

Example 14: Concentration-Dependent ATPase Specific Activity (Recombinant Protein)

Figure 16:
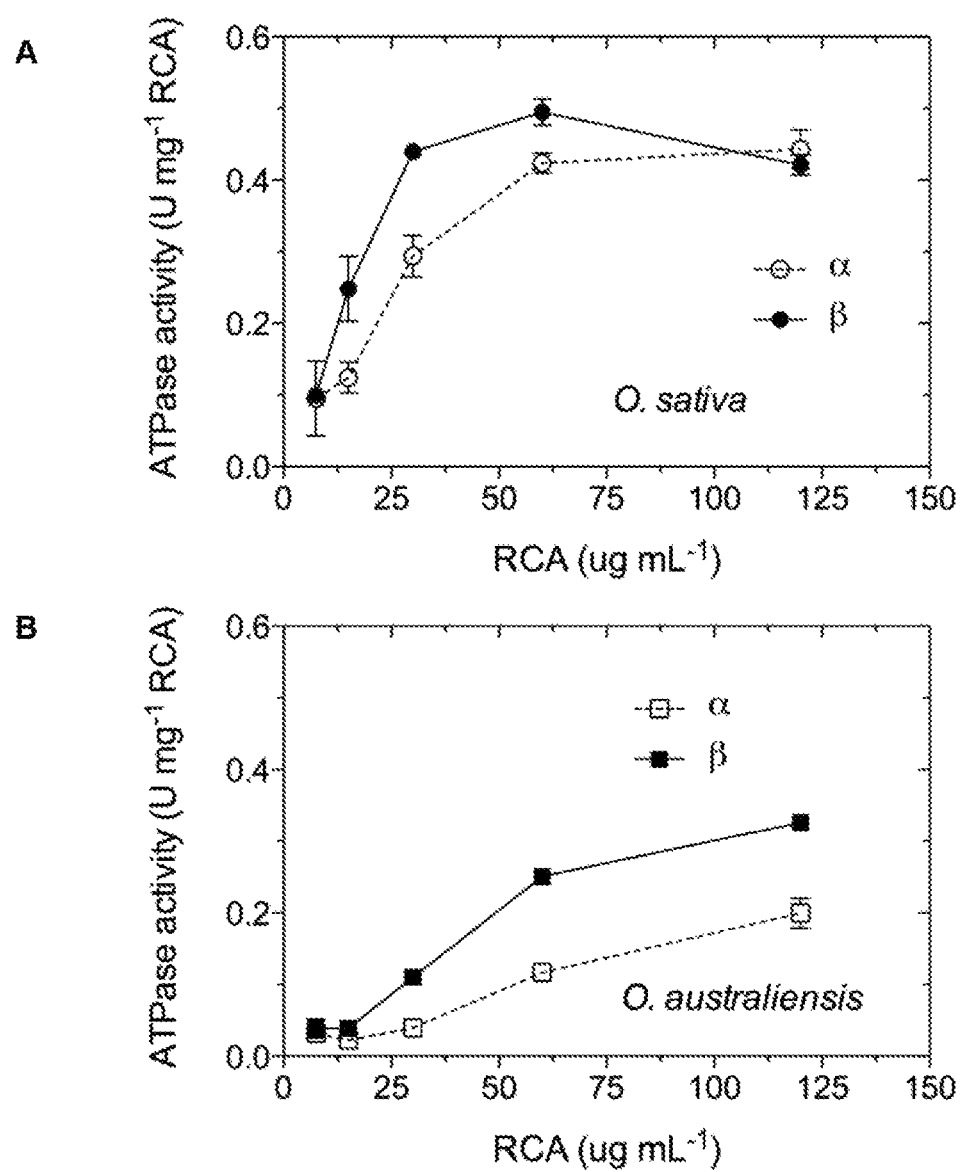
FIG. 16. Effect of recombinant RCA concentration on activity of the alpha and beta forms of RCA as measured by ATPase activity for *O. sativa* (upper panel) and *O. australiensis* (lower panel). Values are means±SE of three experimental replicates.

Inhibition of Rubisco activation at low RCA concentration may be attributed to either a failure of the protein to self-assemble into a functioning oligomer or to a positive allosteric interaction between RCA and Rubisco. To establish which phenomenon accounts for the loss of function at low RCA concentration, the specific activity of ATP hydrolysis by RCA was determined over a range of RCA concentrations (FIG. 16). The ATPase activity of RCA is independent of Rubisco and conditional on formation of a self-aggregating oligomer. It is therefore reasonable to suggest that ATP hydrolysis by RCA is the most direct indicator of the functioning of the self-interacting enzyme oligomer. The results given in FIG. 16 support the conclusion that low RCA concentrations limit oligomer formation, leading to a loss of RCA activity. This is evident in that specific activity of ATP hydrolysis falls at low RCA concentrations. If the RCA oligomer was not inhibited by low RCA concentration the specific activity would be constant, as enzymatic concentration is implicit in the specific activity calculation. Previous studies of spinach also show that ATPase activity was inhibited by low RCA concentrations, attributed to concentration effects on the self-aggregating oligomer (Wang, Z. Y., Ramage, R. T. & Portis Jr, A. R. (1993) Biochimica et Biophysica Acta (BBA)—Protein Structure and Molecular Enzymology 1202, 47-55.). Of note, the inhibition of ATPase activity at low concentration is greater for $RCA_{Oa}$ than $RCA_{Os}$ and more so for the alpha than beta isoform, matching the Rubisco activation concentration-dependent limitations.

Example 15: Temperature Response of Recombinant RCA

The temperature response of partially purified leaf-extracted RCA from the *Oryza* species shows Rubisco activation activity by RCA from *O. sativa* to be susceptible to temperatures of 36° C. and above (FIG. 11). Contrastingly, Rubisco activation activity by RCA from *O. australiensis* extracted from leaves is stable at all measured temperatures up to 42° C.

Figure 17:
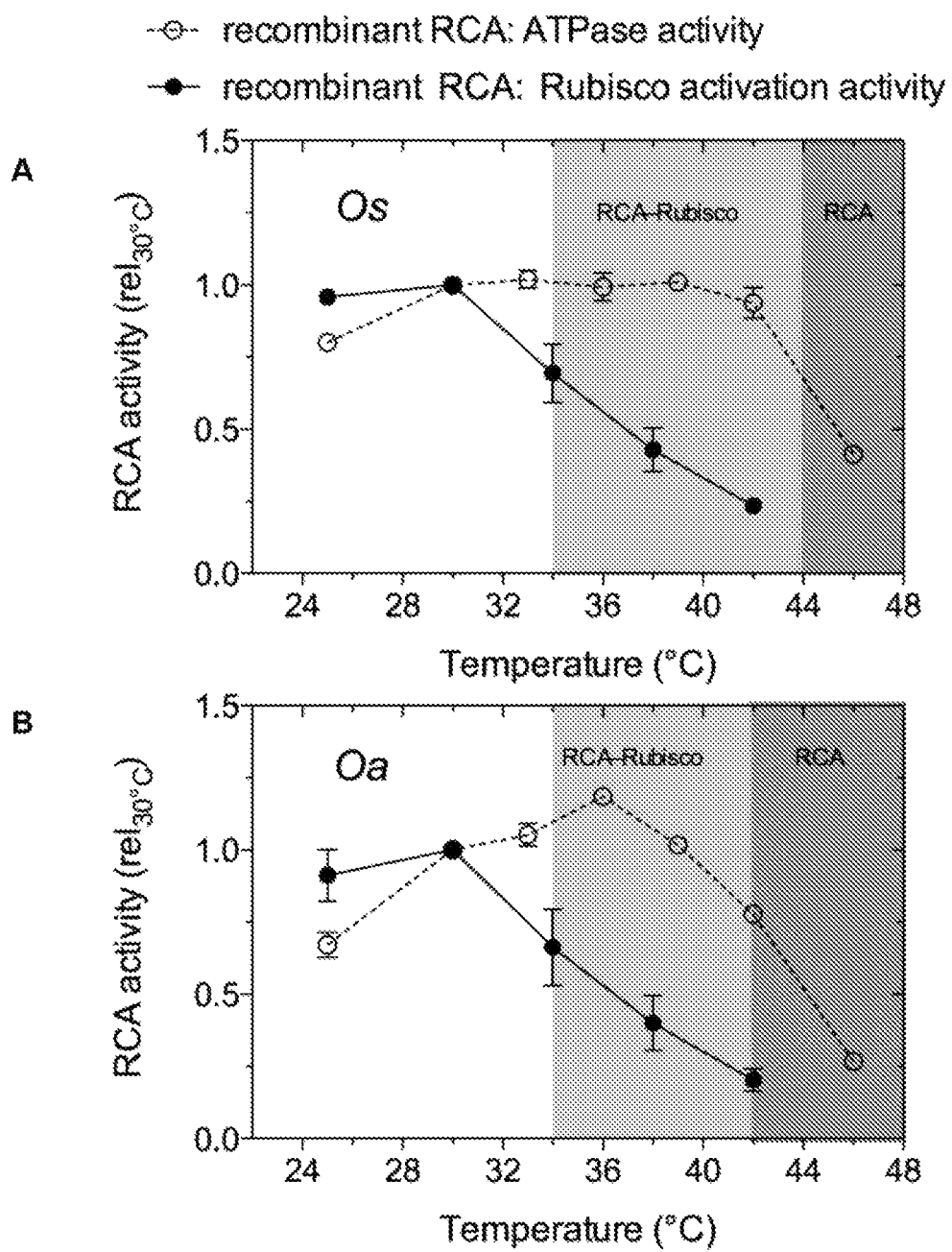
FIG. 17. Temperature-dependent stability of the self-aggregating recombinant RCA oligomer and RCA-Rubisco complex for *O. sativa* (top panel) and *O. australiensis* (bottom panel). Stability is defined as no substantial decline in activity relative to that at 30° C. Stability of the RCA oligomer is purported to equate to stability of ATP hydrolysis activity. Stability of the RCA-Rubisco complex is purported to represent stability of recombinant RCA-mediated Rubisco activation. Temperatures at which the RCA-Rubisco complex is heat-labile is light-grey shaded, whereas the heat-labile range for both the RCA-Rubisco complex and RCA oligomer are dark-grey shaded.

ATP hydrolysis activity was assayed as described by Barta, C., Carmo-Silva, A. E. & Salvucci, M. E. (2011) Methods Mol. Biol. 684, 375-382. Recombinant $RCA_{Oa}$ has lower ATP hydrolysis activity than $RCA_{Os}$ at comparable concentrations (FIG. 9). FIG. 17 plots RCA oligomer heat stability, as determined by ATPase activity, against the RCA-Rubisco complex heat stability, as determined by RCA-mediated Rubisco activation. The temperature stability of ATP hydrolysis of recombinant $RCA_{Oa}$ matches that of $RCA_{Os}$, both being heat stable, not losing activity until 40° C. (FIG. 9), well above the inhibition of Rubisco activation activity by recombinant RCA (FIG. 17). The interaction of RCA with Rubisco is therefore an important factor in heat stability of RCA activation activity, more so than the susceptibility of RCA to temperature in isolation.

Example 16: Oligomeric RCA Heat Stability Versus RCA-Rubisco Heat Stability

The heat-labile nature of both *O. sativa* and *O. australiensis* recombinant RCA-Rubisco complexes as presented by the solid lines in FIG. 17 raises an interesting consideration. As the self-aggregating recombinant RCA oligomer (*O. sativa* and *O. australiensis*) is heat-stable (determined by the heat stability of ATP hydrolysis, indicative of a functional protein) yet the RCA-Rubisco complex is heat-labile (determined by the Rubisco activation activity of RCA, which is reliant on RCA and Rubisco interactions), the susceptibility of the RCA to heat in rice must therefore be due to protein-protein interactions of RCA with Rubisco rather than RCA interaction with itself. FIG. 17 plots RCA oligomer heat stability, as determined by ATPase activity, against the RCA-Rubisco complex heat stability, as determined by RCA-mediated Rubisco activation. The results support RCA-Rubisco complex heat susceptibility as the limitation to Rubisco activation for both species.

Example 17: Interaction of RCA with *O. australiensis* Rubisco

Until now all Rubisco activation experiments have used Rubisco extracted and purified from *O. sativa*. Examining the interaction of $RCA_{Os}$ and $RCA_{Oa}$ with *O. australiensis*

Figure 18:
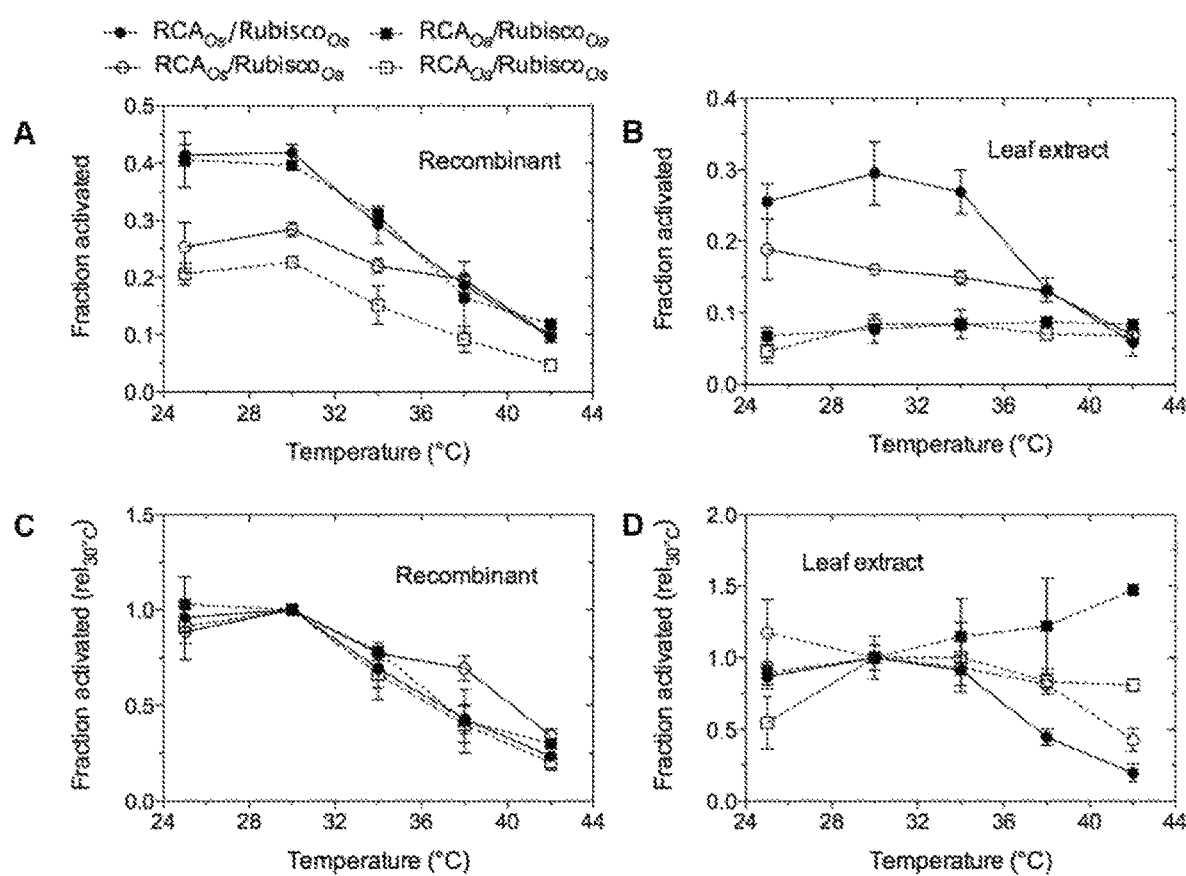
FIG. 18. Temperature-dependent stability of Rubisco activation by recombinant and leaf extracted RCA$_{Os}$ and RCA$_{Oa}$ in combination with *O. sativa* (Rubisco$_{Os}$) and *O. australiensis* (Rubisco$_{Oa}$) Rubisco. Leaf-extracted RCA$_{Os}$ and RCA$_{Oa}$ in combination with Rubisco$_{Oa}$ and recombinant RCA$_{Os}$ and RCA$_{Oa}$ in combination with Rubisco$_{Oa}$ is in duplicate.

Rubisco is important considering the RCA-Rubisco interaction is critical to the temperature limitation in RCA activity. FIG. 18 compares the temperature-dependent response of both recombinant and leaf-extracted RCA against Rubisco extracted and purified from the two species. Key findings are:

Irrespective of the Rubisco used, recombinant RCA is heat labile.

The heat-stability of leaf-extracted RCAs is improved when interacting with O. australiensis Rubisco rather than O. sativa Rubisco.

The results show that the primary structure of Rubisco from O. australiensis is different from that of O. sativa and Rubisco can influence the stability of the RCA-Rubisco complex. From interactions between Os and Oa leaf extracted RCA and Os and Oa Rubisco (FIG. 18) it seems that a reduced Rubisco activation activity of leaf extracted RCA at ambient temperature, as compared to recombinant RCA, is associated with increased heat-stability of Rubisco activation activity of the leaf extracted RCA at higher temperature.

Figure 19:
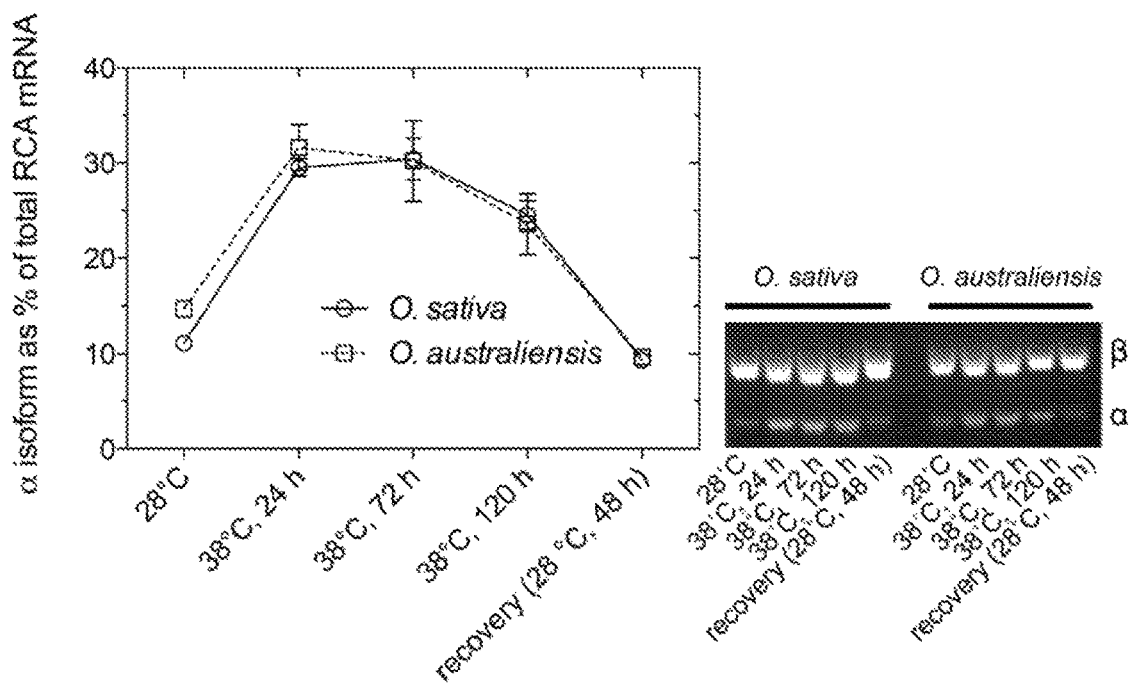
FIG. 19. Heat-dependent gene response of the alpha and beta isoform of RCA. Image analysis of cDNA from three biological replicates, with one set given on the right, allowed for the ratio of alpha to beta isoform to be determined. The ratio of alpha to beta isoform is presented as the % of total RCA mRNA that is comprised of the alpha isoform.

Example 18: Regulation of the Alpha and Beta Isoform of RCA—Heat-Dependent Up-Regulation of the Alpha Isoform With increased growth temperature from 28 to 38° C. there is an increase in mRNA expression of the alpha isoform of RCA. The beta isoform expression stays relatively constant, with high growth temperatures increasing the ratio of alpha to beta RCA isoforms (FIG. 19). The increase in ratio of alpha to beta isoform with heat is the same for both O. sativa and O. australiensis, suggesting a common pattern of regulation of the genes in both species. The increase in expression of the alpha isoform peaks within 72 h of heat exposure before beginning to drop slightly by 120 h of heat. After 48 hours of reducing the growth temperature back to 28° C., the level of alpha to beta isoform mRNA returns to pre heat-treatment levels.

Protein abundance of the alpha and beta isoforms of RCA is proportional to mRNA levels. Visualisation of partially purified RCA extracts run on SDS-PAGE indicate greater alpha RCA protein abundance from 72 h of heat exposure onwards. Unlike RNA expression, there is no discernible increase in alpha isoform protein abundance before 72 h but a greater abundance at 28° C. after recovery from heat exposure. The results suggest protein abundance has a 48-h lag-time behind changes in gene expression.

Figure 20:
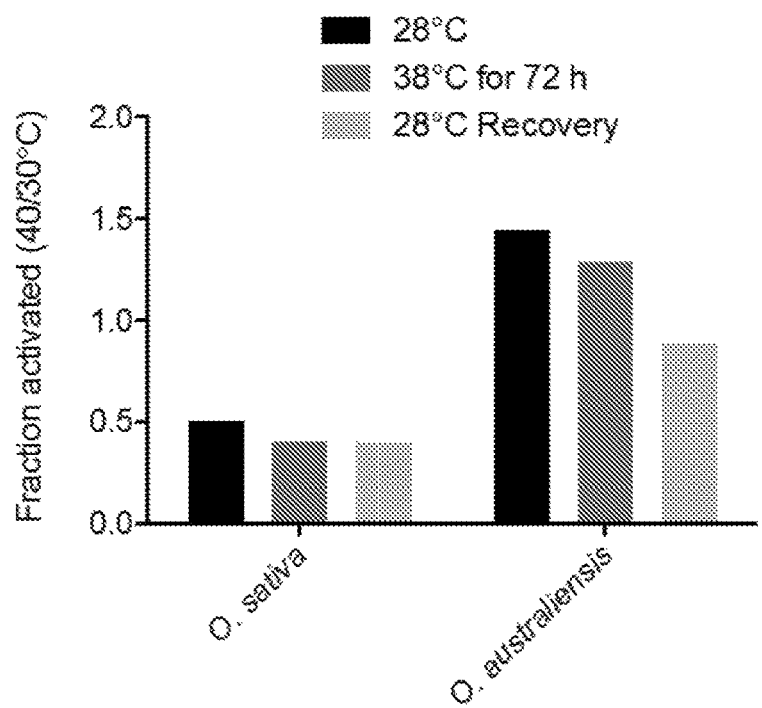
FIG. 20. Treatment effect on RCA extracted from control, heat-treated and post-heat treatment leaves, as determined by comparisons of fraction-activated values at 38° C. compared to 28° C.

To test whether changes in isoform composition of the RCA complex influence the heat-stability of RCA enzymatic function, the temperature effects on Rubisco activation by RCA extracted from plants over the time-course of heat treatment were measured at 28 and 38° C. and are shown in FIG. 20. The heat-stability of RCA is not improved by increasing the ratio of alpha to beta isoform. In fact, RCA heat-stability falls slightly in both species when there is a greater presence of the alpha isoform.

Example 19: The Ability of RCA from Rice to Activate Wheat Rubisco

To determine the activation activity of rice RCA and wheat RCA on Rubisco from wheat ($Rubisco_{wheat}$), RCA was partially purified from leaves. The alpha and beta isoforms were separated using anion-exchange chromatography and the beta isoform was used to determine the Rubisco activation activity. The beta isoform was used as it had a higher purity of RCA and less Rubisco than the alpha isoform fraction. Although by no means pure (approx. 60-70% of total protein) the samples were of higher purity than the ammonium sulphate precipitate samples previously used (see FIGS. 5, 11 and 13) for leaf extracted RCA experiments (approx. 30-40%).

When comparing Rubisco from the two rice species and wheat, there was a similar response to temperature (FIG. 22, panel A)). For all three species the specific activity of fully carbamylated Rubisco ranged from 0.5 to 0.8 $U·mg^{-1}$ across the measured temperature range and all had a slight increase in activity with increasing temperature. Inhibited Rubisco without the addition of RCA also had a slight increase in specific activity with increased temperature and all three species had a similar rate, never exceeding 0.2 $U·mg^{-1}$.

Figure 22:
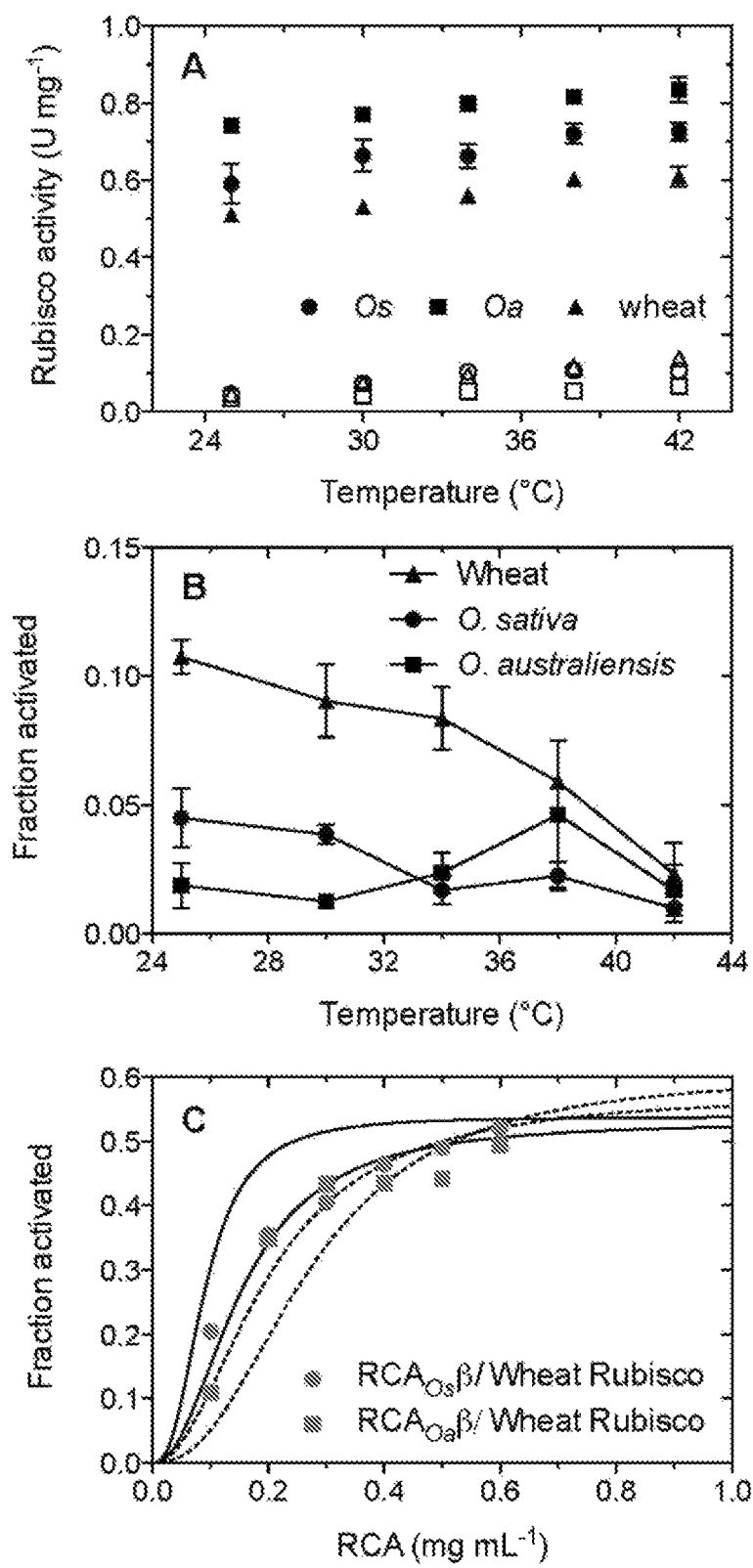
FIG. 22. Activation of wheat and rice Rubisco by RCA from rice. The specific activity of Rubisco from *O. sativa* (Rubisco$_{Os}$), Rubisco from *O. australiensis* (Rubisco$_{Oa}$) and Rubisco from wheat (Rubisco$_{wheat}$)(Panel A) and RCA interaction with Rubisco$_{wheat}$ (Panels B to C). Panel A shows the specific activity of fully carbamylated wheat, *O. sativa* (Os) or *O. australiensis* (Oa) Rubisco (closed symbols) and the spontaneous activity of inhibited Rubisco without addition of RCA (open symbols). Panel B shows the temperature-dependent activation of wheat Rubisco by the beta isoform of RCA extracted from wheat, Os or Oa leaves. The RCA was partially purified from leaf tissue using ammonium sulphate precipitation followed by an extra anion-exchange purification step as described in Example 19. Briefly, desalted RCA leaf extract was passed through a strong anion-exchange column (Q-Sepharose) followed by elution with 0.2 M KCl, which allowed for separation and collection of the beta isoform of RCA. 0.4 mg mL$^{-1}$ of RCA extract was used per assay. Panel C is the concentration-dependent activation of wheat Rubisco by recombinant RCA$_{Os}$ (blue circles) and RCA$_{Oa}$ (red squares). The solid and dashed curves are the RCA$_{Os}$ and RCA$_{Oa}$ recombinant RCA concentration-dependent activation of Rubisco$_{Os}$, respectively. For Panel A and B the means and SE of three experimental replicates are given, while in Panel C the individual observations are plotted.

When $Rubisco_{wheat}$ was activated by leaf-extracted beta isoform, at moderate temperature of less than 34° C., wheat RCA was at least twice as active as the rice RCA isoforms (FIG. 22, panel B). There were smaller differences above 34° C., as a results of the stronger inhibition of $Rubisco_{wheat}$ at higher temperatures. The temperature-response curve of wheat RCA acting on $Rubisco_{wheat}$ was similar to leaf-extracted RCA from rice acting on $Rubisco_{Os}$ (FIG. 11), with a slight decline from 25 to 34° C. but a more pronounced decline when temperature reached 38 and 42° C.

(FIG. 22, panel C) shows recombinant forms of $RCA_{Os}$ and $RCA_{Oa}$ were able to activate $Rubisco_{wheat}$ to the same extent as activating Rubisco from rice ($Rubisco_{rice}$). Unlike the results from leaf extracted RCA, the results from recombinant RCA suggest that RCA from both rice species is capable of activating $Rubisco_{wheat}$ to the same extent as $Rubisco_{rice}$ and are therefore completely compatible with $Rubisco_{wheat}$.

Example 20: Growth Chamber Experiment with Transgenic Rice Lines Under High Day Temperature at 45° C.

Plant Expression Vectors and Transformation

The coding sequences for the short RCA (rcaII) and long RCA (rcaI) coding region from O. australiensis were obtained by chemical DNA synthesis and were adapted to rice codon usage. Different vectors were made (FIG. 7) using the synthetic genes with the complete sequence of rcaIIOa (SEQ ID NO 52) and with a 5AA truncated sequence of rcaIIOa (SEQ ID NO 51), as well as the with the complete sequence of rcaIOa (SEQ ID NO 50). In all vectors, the gene was driven by the promoter of rcaI from O. meridionalis (SEQ ID NO 53). The intermediate cloning vector (e.g. pTKAW39, pTKA40, pTNVS299) was constructed in Escherichia coli. It was transferred to the acceptor Agrobacterium tumefaciens strain via a heat shock. Agrobacterium-mediated gene transfer of the intermediate cloning vector(s) resulted in transfer of the DNA fragment between the T-DNA border repeats to the plant genome.

As target tissue for transformation, immature embryo or embryo-derived callus derived from japonica and indica rice cultivars which were cut into small pieces, essentially using the technique described in PCT patent publication WO 92/09696. Agrobacterium was cocultivated with the rice tissues for some days, and then removed by suitable antibiotics. Transformed rice cells were selected by addition of glufosinate ammonium (with phosphinothricin 5 mg/L) to the rice tissue culture medium.

Calli growing on media with glufosinate ammonium were transferred to regeneration medium. When plantlets with roots and shoots had developed, they were transferred to soil, and placed in the greenhouse.

Genotypes

Five transgenic lines—numbered 475 to 479, were tested. Information on the plants tested are set out in Table 12.

TABLE 12

List of transgenic rice events used in the high day temperature experiment.

| Designation | Description | Clone Information |
|---|---|---|
| 475 | pTNVS299 | Single copy line |
| 476 | pTNVS299 | Single copy line |
| 477 | pTKA40 | Single copy line |
| 478 | pTKAW40 | Single copy line |
| 479 | pTKAW39 | Single copy line |
| 480 | azygous control | NA |

Experimental Design

Transgenic rice (T3 homozygous rcaIIOa single copy lines) and pooled azygous lines were sown in 66-wells sowing trays after seeds had been soaked in water for 1.5 days. The seedlings were transplanted to 9 cm pots after 20 days and 14 individuals of similar size/height (visual score) were chosen for the experiment. A randomized block design with border plants was used. The growth chamber normal/control conditions were 12 h light (ca. 300 µmol m$^{-2}$ s$^{-1}$ PAR), 22° C. during the night and 28-29° C. during the day. The maximum temperature was imposed for 12 h during the light period while plants were held at 22° C. overnight. Temperature was increased stepwise from 28/29° C. to 45° C. over a 48 hour period 10 days after transplanting (30 days after sowing). See FIG. 23 for the temperature settings once 45° C. was achieved (high day temperature). Relative humidity was kept between 60 and 70% throughout the experiment.

Leaf Elongation Rates (LVDT)

Leaf elongation was measured on plants every day for five consecutive days, once in the 'morning period' (about 9 am until about 1 pm), and again in the 'afternoon period', which commenced by 2 pm when plants were attached to the machine. Measurements for the 'afternoon' plants were therefore terminated the following morning. One plant of each genotype (five viable transgenic lines and one azygous control) was attached to the pulley system and readings commenced, with leaf length logged 10 times hourly. Nutrient solution was liberally supplied throughout. Plants were chosen successively from 14 blocks, with a new young emerging leaf being required for each of the ten measurements made over five days. Rates of elongation were analysed in the normal way, using logs in Excel spreadsheets to calculate rates (mm h$^{-1}$) over the period of steady-state elongation in the hottest period. Rates did not differ significantly between genotypes during the night.

Leaf Gas Exchange

After 2 weeks of high day temperature treatment, leaf gas exchange measurements were carried out during the peak temperature in the afternoon. The following parameters were recorded with an open infrared gas analyser system LI-6400XT (LI-COR Inc., Lincoln, Nebr., USA):

a) Net photosynthesis rates ($A_n$) under saturating light of 1500 PAR (integrated light source of the LI-6400XT leaf chamber) and at 400 ppm $CO_2$ and 45° C. (block temperature setting), b) maximum carboxylation rates of Rubisco ($V_{c,max}$), derived from the slope of $A_n$ vs. $C_i$ (internal sub-stomatal $CO_2$ concentration) curves that were recorded by stepwise changing $CO_2$ concentration around the leaf inside the leaf chamber, c) the rate of $A_n$ induction during dark-light transitions, subjecting plants to low light (ca. 50 PAR) for about 30 min, then illuminating the measured leaf at 1500 PAR while following the rise of $A_n$ over time (ca. 15 min).

The initial slope was taken as surrogate for induction kinetics of photosynthesis and hence of Rubisco activation (Carmo-Silva and Salvucci, 2013 Plant Physiol. 161, 1645-1655; Yamori et al., 2012 Plant J. Cell Mol. Biol. 71, 871-880).

Statistical analysis (ANOVA test) was carried out with in-house developed R-package.

Flowering Time/Biomass/Seed Weight

The days to flowering are recorded for every plant. After first plant starts to flower temperature will be reduced to 28-29° C. (control conditions) in order to avoid pollen sterility. All plants are harvested at full maturity and number of tillers, panicles and seeds as well as vigor (visual score 1 to 6), seed set (%), fresh and dry weight (g) per plant are taken. Seed weight is recorded after drying seeds.

Results

Rubisco Activation and Photosynthesis

The transgenic rice plants 479 with the pTKAW39 vector showed higher values of $A_n$ and Vc,max than their azygous controls after 2 weeks of heat treatment (FIG. 24), while the other four lines had similar $A_n$ and a tendency towards increased Vc,max. The rate of induction of Rubisco activity (slope $A_n$ min$^{-1}$) was significantly higher in the transgenic plants 479 with the pTKAW39 vector (22%) and higher in 477 (pTKAW40) than in the azygous counterparts, indicating a beneficial effect of the short RCA variants of O. australiensis (rcaIIOa) on the activation of Rubisco. Thus, expression of rcaIIOa apparently contributed to a better photosynthetic performance under heat stress.

Leaf Elongation Rate (LER)

Six plant lines, numbered 472 to 479, and an azygous control, 480 were tested for leaf elongation rate (LER) and the results are set out in Table 13 and Table 14. These rates are means calculated across the heat period as defined in FIG. 23. LERs declined by about 50% over the period of heating, reflecting increasing an inhibitory effect as heat had its effect on metabolism, but recovered to between 6 and 8 mm h$^{-1}$ by the following morning. Lines 475 and 479 elongated fastest, with Line 475 being the only genotype to be significantly faster than the other seven genotypes, although Line 479 did not elongate significantly slower than Line 475.

TABLE 13

LERs for seven RCA rice transformants and an azygous control (Line 480)

| Genotype designation | Leaf elongation rate (mm h$^{-1}$) during heat period |
|---|---|
| 472 | 3.92 b |
| 473 | 3.62 b |
| 474 | 3.87 b |
| 475 | 4.80 a |
| 476 | 3.91 b |
| 478 | 3.70 b |
| 479 | 4.26 a,b |
| 480 | 3.88 b |

Tiller Development

Tiller numbers were counted for plants in each block after a week of heat treatment (six-week-old plants) as a measure of shoot development (Table 14). Tiller numbers were re-counted after seven weeks of heat treatment and are reported in FIG. 30. Line 479 always had significantly more tillers (7 per plant) than the others lines, including the control (Line 480).

Figure 23:
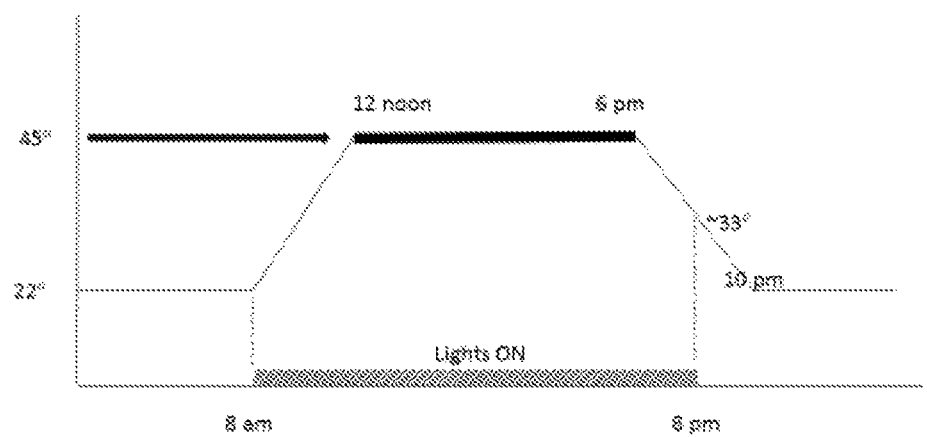
FIG. 23. Shows temperature and light settings of the growth chamber for the experiment with transgenic rice lines.

FIG. 31 shows results of tillers per plant for eight lines counted in six-week-old plants that had been exposed to one week at 45° C. day temperatures as described in FIG. 23. Lines 1-8 are listed in the order, 474, 472, 478, 476, 473, 475, 480 (control) and 479, respectively.

TABLE 14

Numbers of tillers in six-week-old plants

| Genotype Block | 479 | 475 | 480 (C) | 476 | 478 |
|---|---|---|---|---|---|
| 1 | 7 | 5 | 5 | 6 | 5 |
| 2 | 8 | 5 | 5 | 5 | 5 |
| 3 | 8 | 5 | 7 | 5 | 6 |
| 4 | 7 | 5 | 7 | 8 | 4 |
| 5 | 7 | 8 | 4 | 4 | 5 |
| 6 | 7 | 5 | 8 | 5 | 5 |
| 7 | 6 | 6 | 7 | 5 | 7 |
| 8 | 7 | 8 | 6 | 4 | 6 |
| 9 | 8 | 7 | 5 | 5 | 4 |
| 10 | 7 | 8 | 7 | 6 | 4 |
| 11 | 6 | 6 | 6 | 7 | 9 |
| 12 | 9 | 5 | 8 | 5 | 5 |
| 13 | 4 | 5 | 4 | 6 | 3 |
| 14 | 7 | 7 | 6 | 5 | 4 |
| Average | 7.0 | 6.1 | 6.1 | 5.4 | 5.1 |
| S.E.M. | 0.29 | 0.32 | 0.33 | 0.27 | 0.38 |

It will be appreciated by persons skilled in the art that numerous variations and/or modifications may be made to the invention as shown in the specific embodiments without departing from the spirit or scope of technology as broadly described. The present embodiments are, therefore, to be considered in all respects as illustrative and not restrictive,

---

The invention claimed is:

1. An isolated nucleic acid encoding a Rubisco activase from *Oryza australiensis* operably linked to a heterologous promoter, wherein the *Oryza australiensis* Rubisco activase comprises SEQ ID NO: 39 or 40, wherein when expressed in a plant other than *Oryza australiensis* the Rubisco activase forms a complex with a Rubisco from the plant to confer thermostability to the complex at 35° C. to 45° C., and wherein the complex further comprises greater enzymatic activity at 35° C. to 45° C. than the enzymatic activity of complexes comprising *Oryza sativa* Rubisco activase under the same conditions.

2. A chimeric gene or vector comprising the nucleic acid of claim 1.

3. The isolated nucleic acid of claim 1 wherein the promoter is a plant expressible promoter.

4. The isolated nucleic acid of claim 3 wherein the promoter is a heat-inducible promoter, green-tissue promoter or a chemical-inducible promoter.

5. A host cell comprising the isolated nucleic acid of claim 1.

6. The host cell of claim 5, wherein the host cell is a plant cell.

7. A plant or plant cell comprising the isolated nucleic acid of claim 1, wherein the plant or plant cell is other than *Oryza australiensis*.

8. The plant according to claim 7, wherein the plant is selected from the group consisting of barley, maize, tomato, potato, rice, soybean, cotton, sunflower, alfalfa, lettuce, canola (oilseed rape), sorghum, and wheat.

9. The plant according to claim 8 being rice or wheat.

10. A method of enhancing heat tolerance in a plant comprising introducing the isolated nucleic acid of claim 1 into a plant other than *Oryza australiensis* and expressing the Rubisco activase, wherein expression of the Rubisco activase in the plant enhances heat tolerance of the plant at 35° C. to 45° C. as compared to a control plant lacking said isolated nucleic acid.

11. The method of claim 10 comprising introducing the isolated nucleic acid of claim 3 into the plant.

12. The method of claim 10 further comprising forming a complex between the expressed Rubisco activase and Rubisco from the plant, thereby conferring thermostability to the complex at 35° C. to 45° C. and allowing the plant to fix carbon dioxide in heat stress conditions.

13. The method of claim 10 further comprising forming a complex between the expressed Rubisco activase and Rubisco from the plant, thereby conferring thermostability to the complex at 35° C. to 45° C. and allowing the plant to increase the rate of photosynthesis under heat stress conditions.

14. The method of claim 10 further comprising providing the plant with the chimeric gene or vector of claim 2.

15. A host cell comprising the chimeric gene or vector of claim 2.

16. An isolated nucleic acid comprising SEQ ID NO: 41, 42, 50, 51, or 52 operably linked to a heterologous promoter, wherein the isolated nucleic acid encodes a Rubisco activase comprising SEQ ID NO: 39 or 40.

17. A chimeric gene or vector comprising the nucleic acid of claim 16.

18. The isolated nucleic acid of claim 16, wherein the promoter is a plant expressible promoter.

19. The isolated nucleic acid of claim 18, wherein the promoter is a heat-inducible promoter, green-tissue promoter, or a chemical-inducible promoter.

20. A host cell comprising the isolated nucleic acid of claim 16.

21. The host cell of claim 20, wherein the host cell is a plant cell.

22. A plant or plant cell comprising the isolated nucleic acid of claim 16, wherein the plant or plant cell is other than *Oryza australiensis*.

23. The plant according to claim 22, wherein the plant is selected from the group consisting of barley, maize, tomato, potato, rice, soybean, cotton, sunflower, alfalfa, lettuce, canola (oilseed rape), sorghum, and wheat.

24. The plant according to claim 23 being rice or wheat.

25. A method of enhancing heat tolerance in a plant comprising introducing the isolated nucleic acid of claim 16 into a plant other than *Oryza australiensis* and expressing the Rubisco activase, wherein expression of the Rubisco activase in the plant enhances heat tolerance of the plant at 35° C. to 45° C. as compared to a control plant lacking said isolated nucleic acid.

26. The method of claim 25 comprising introducing the chimeric gene or vector of claim 17 into the plant.

27. The method of claim 25 further comprising forming a complex between the expressed Rubisco activase and Rubisco from the plant, thereby conferring thermostability to the complex at 35° C. to 45° C. and allowing the plant to fix carbon dioxide in heat stress conditions.

28. The method of claim 25 further comprising forming a complex between the expressed Rubisco activase and Rubisco from the plant, thereby conferring thermostability to the complex at 35° C. to 45° C. and allowing the plant to increase the rate of photosynthesis under heat stress conditions.

29. A host cell comprising the chimeric gene or vector of claim 17.

* * * * *